US012611128B2

(12) United States Patent
Vallejo et al.

(10) Patent No.: US 12,611,128 B2
(45) Date of Patent: Apr. 28, 2026

(54) METRICS FOR IMPAIRMENT DETECTING DEVICE

(71) Applicant: Battelle Memorial Institute, Columbus, OH (US)

(72) Inventors: Celeste Vallejo, Durham, NC (US); David A. Friedenberg, Worthington, OH (US); Aaron J. Frank, Dublin, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 929 days.

(21) Appl. No.: 17/351,532

(22) Filed: Jun. 18, 2021

(65) Prior Publication Data

US 2021/0393180 A1 Dec. 23, 2021

Related U.S. Application Data

(60) Provisional application No. 63/041,170, filed on Jun. 19, 2020.

(51) Int. Cl.
| | |
|---|---|
| *A61B 5/16* | (2006.01) |
| *A61B 3/11* | (2006.01) |
| *A61B 5/00* | (2006.01) |
| *G02B 27/00* | (2006.01) |
| *G02B 27/01* | (2006.01) |

(Continued)

(52) U.S. Cl.
CPC .............. *A61B 5/163* (2017.08); *A61B 3/112* (2013.01); *A61B 5/4863* (2013.01); *G02B 27/0093* (2013.01); *G02B 27/017* (2013.01); *G06F 3/013* (2013.01); *G06T 19/006* (2013.01)

(58) Field of Classification Search
CPC ....... A61B 5/163; A61B 3/112; A61B 5/4863; A61B 5/4845; A61B 5/6803; A61B 5/742; A61B 3/113; A61B 3/111; A61B 2505/09; A61B 5/165; A61B 5/162; A61B 5/161; A61B 5/16; A61B 5/6802; A61B 5/4848; A61B 3/11; G02B 27/0093; G02B 27/017; G06F 3/013; G06T 19/006
See application file for complete search history.

(56) References Cited

U.S. PATENT DOCUMENTS

| | | | |
|---|---|---|---|
| 5,187,506 A * | 2/1993 | Carter | .................... A61B 3/112 351/205 |
| 7,614,745 B2 | 11/2009 | Waldorf | |

(Continued)

FOREIGN PATENT DOCUMENTS

WO    WO 2016/168724 A1    10/2016

OTHER PUBLICATIONS

International Search Report for PCT Application No. PCT/US2021/038049 Dated Sep. 24, 2021.

(Continued)

*Primary Examiner* — Jason M Sims
*Assistant Examiner* — Matthew Eric Ogles
(74) *Attorney, Agent, or Firm* — Lippes Mathias LLP

(57) ABSTRACT

The present disclosure relates generally to metrics used to detect or indicate a state of impairment in a test subject due to use of drugs or alcohol, and more particularly to metrics used in connection with a virtual-reality ("VR") environment that implements drug and alcohol impairment tests, where the metrics are used to detect or indicate impairment.

20 Claims, 64 Drawing Sheets
(42 of 64 Drawing Sheet(s) Filed in Color)

(51) Int. Cl.
  *G06F 3/01*          (2006.01)
  *G06T 19/00*         (2011.01)

(56)              References Cited

U.S. PATENT DOCUMENTS

| | | | | |
|---|---|---|---|---|
| 8,585,609 | B2 | 11/2013 | Kiderman et al. | |
| 8,668,337 | B2 | 3/2014 | Waldorf et al. | |
| 8,899,748 | B1 * | 12/2014 | Migdal | A61B 5/004 |
| | | | | 351/210 |
| 9,101,312 | B2 | 8/2015 | Waldorf | |
| 9,730,583 | B2 | 8/2017 | Kiderman et al. | |
| 10,231,614 | B2 | 3/2019 | Krueger | |
| 10,575,726 | B2 | 3/2020 | Wetzel et al. | |
| 2006/0270945 | A1 * | 11/2006 | Ghajar | A61B 5/377 |
| | | | | 600/558 |
| 2008/0309616 | A1 | 12/2008 | Massengill | |
| 2012/0108909 | A1 | 5/2012 | Slobounov et al. | |
| 2014/0320820 | A1 * | 10/2014 | Kumarasamy | A61B 3/112 |
| | | | | 351/221 |
| 2015/0257681 | A1 | 9/2015 | Shuster | |
| 2016/0167672 | A1 | 6/2016 | Krueger | |
| 2016/0262608 | A1 | 9/2016 | Krueger | |
| 2016/0302713 | A1 * | 10/2016 | Maruta | A61B 3/0025 |
| 2018/0333092 | A1 * | 11/2018 | Roshan | A61B 3/0091 |
| 2019/0180178 | A1 * | 6/2019 | Umeda | G06V 20/41 |
| 2019/0290197 | A1 * | 9/2019 | Nothacker | A61B 5/6833 |
| 2020/0121195 | A1 | 4/2020 | Bresler et al. | |
| 2020/0121235 | A1 | 4/2020 | Gibbons et al. | |
| 2022/0207726 | A1 * | 6/2022 | Ren | G06V 10/267 |

OTHER PUBLICATIONS

Viviane Clay, Eye Tracking in Virtual Reality, Journal of Eye Movement Research, Apr. 2019, pp. 1-18.

* cited by examiner

LOC: Cannabis

LOC: Cannabis

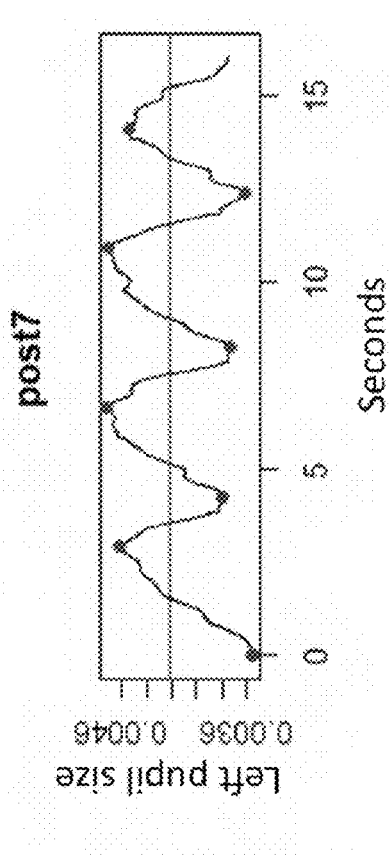
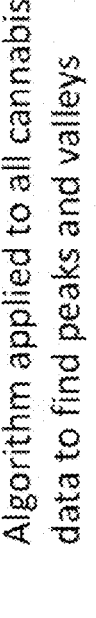
Algorithm applied to all cannabis data to find peaks and valleys
FIG. 36B
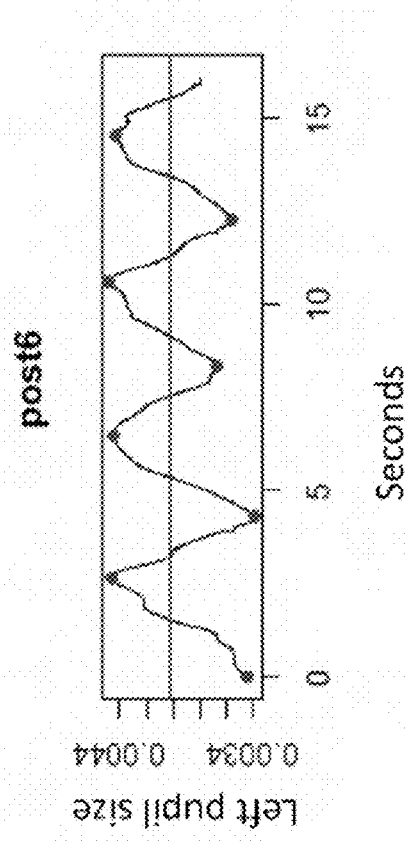

METRICS FOR IMPAIRMENT DETECTING DEVICE

CROSS-REFERENCE TO RELATED APPLICATIONS

This application claims the benefit of U.S. Provisional Application Ser. No. 63/041,170 filed Jun. 19, 2020 and titled METRICS FOR IMPAIRMENT DETECTING DEVICE. U.S. Provisional U.S. Provisional Application Ser. No. 63/041,170 filed Jun. 19, 2020 and titled METRICS FOR IMPAIRMENT DETECTING DEVICE is incorporated herein by reference in its entirety.

BACKGROUND

The present disclosure relates generally to impairment assessment devices and methods for detecting drug impairment, alcohol impairment, impairment due to fatigue, and/or the like, and to metrics used to detect or indicate a state of impairment in a test subject due to use of drugs or alcohol, and more particularly to metrics used in connection with a virtual-reality ("VR") environment that implements drug and alcohol impairment tests, where the metrics are used to detect or indicate impairment.

Impairment can be brought about by or as the result of ingesting or otherwise introducing an intoxicating substance, such as alcohol or a drug. Excessive fatigue due to lack of sleep, or certain illnesses, can also cause impairment. Law enforcement officers commonly engage in the detection of a person's impairment, such as during traffic stops or other situations that may arise during the officers' line of duty.

Law enforcement officers currently have access to devices, such as a breathalyzer, which can detect or indicate impairment due to alcohol. However, there is no accepted or ubiquitous device such as the breathalyzer for marijuana and other non-alcoholic drugs. Accordingly, since law enforcement officers do not currently have access to roadside or otherwise portable impairment detectors, decisions regarding impairment typically rely on the subjective judgement of individual officers.

In addition, often a certified Drug Recognition Expert ("DRE") is required to make a decision on a person's impairment. However, the training, certification, and recertification, required by DREs, can be time consuming and costly.

Thus, there is a need for an easy to use impairment assessment device that employs objective, and highly repeatable metrics to assist law enforcement officers in gathering drug impairment indicators. As a result, officers and other officials or test administrators will be empowered to make on-site decisions without needing a certified DRE. Moreover, training and recertification costs will be reduced, allowing time and resources to be redirected to other areas of need.

BRIEF DESCRIPTION

Disclosed herein are impairment detection systems and methods that employ various metrics. The systems and methods suitably create a virtual-reality ("VR") environment that implements tests from Standard Field Sobriety Tests ("SFSTs") and other drug and alcohol impairment tests used by police officers in the field. The exemplary metrics are configured to permit such impairment tests to be implemented as closely as possible to guidelines established by police officers and other agents such as drug recognition experts ("DREs").

More specifically, the impairment tests implemented by the exemplary metrics for evaluation include, but are not limited to, one or a combination of: (a) Horizontal Gaze Nystagmus Test—assesses the ability of a test subject to smoothly track a horizontally moving object and checks for eye stability during the test; (b) Vertical Gaze Nystagmus Test—checks for eye stability as the test subject tracks a vertically moving object; (c) Lack of Convergence Test—checks the ability of the test subject to cross his or her eyes when an object is brought towards the bridge of the subject's nose; (d) Pupil size and response test—measures the subject's pupil size in normal lightning conditions, as well as abnormally dark and bright conditions; and, (e) Modified Romberg Balance Test—tests the subject's ability to follow directions, measure time, and balance.

The exemplary metrics are implemented with these impairment tests in a virtual world through use of a VR headset configured to include eye tracking hardware and software. As each test is conducted, the exemplary eye tracking hardware and software is capable of accurately measuring pupil size, pupil position, and eye gaze direction independently for each eye at a high sample rate.

In order to make determinations of the test subject's level of impairment, the presently disclosed metrics are used to determine various useful values from the eye tracking data collected during each time step of the VR simulation. The eye tracking data being informed with such metrics is then output as useful information from which determinations of impairment can made objectively, repeatedly, reliably, and accurately, while eliminating or substantially reducing the subjective nature inherent in previous manual impairment tests performed in the field.

These and other non-limiting characteristics of the disclosure are more particularly disclosed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

DETAILED DESCRIPTION

Figure 1:
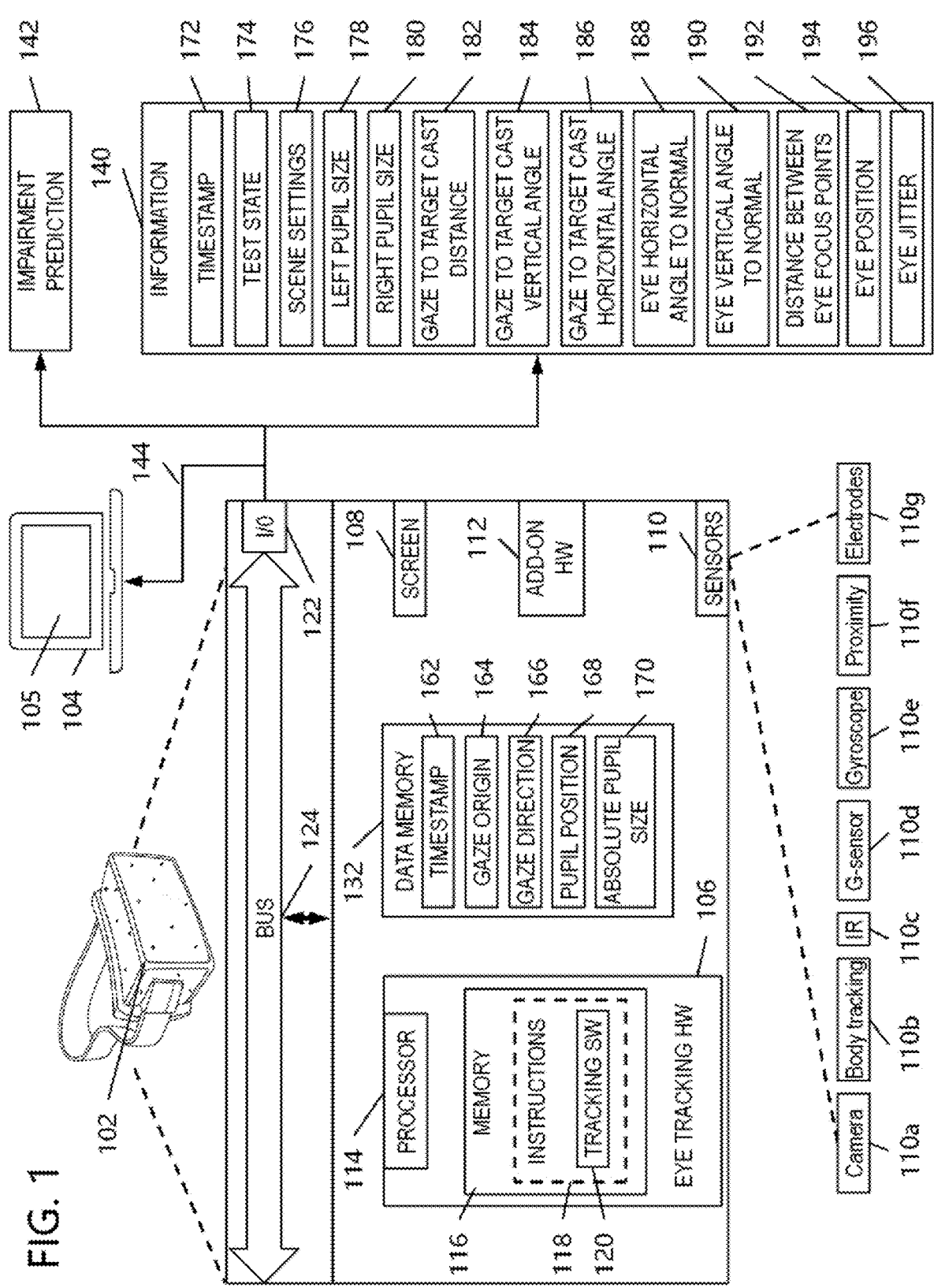
FIG. 1 is a block diagram illustrating a system for performing an impairment test which includes a virtual-reality ("VR") headset and an associated host computer in accordance with one embodiment of the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the terms "comprise(s)," "include(s)," "having," "has," "can," "contain(s)," and variants thereof, as used herein, are intended to be open-ended transitional phrases, terms, or words that require the presence of the named components/ingredients/ steps and permit the presence of other components/ingredients/steps. However, such description should be construed as also describing systems or devices or compositions or processes as "consisting of" and "consisting essentially of" the enumerated components/ingredients/steps, which allows the presence of only the named components/ingredients/ steps, along with any unavoidable impurities that might result therefrom, and excludes other components/ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

A value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number.

The following examples are provided to illustrate the methods, processes, systems, apparatuses, and properties of the present disclosure. The examples are merely illustrative and are not intended to limit the disclosure to the materials, conditions, or process parameters set forth therein.

With reference to FIG. 1, a block diagram is illustrated showing a system 100 for performing an impairment test according to an embodiment of the present disclosure. The system 100 generally includes a virtual-reality ("VR") headset unit 102 and an associated host computer 104 with display 105. Some suitable embodiments of the hardware of the VR headset 102 include various commercially available VR headsets (optionally modified to include add-on hardware components referred to below) such as those available from Oculus VR, LLC (a subsidiary of Facebook Inc.), HTC Vive VR headsets available from HTC Corporation, Valve VR headsets available from Valve Corporation, or so forth; alternatively, a custom VR headset may be provided for the disclosed impairment assessment system.

As used herein, the VR headset 102 encompasses both virtual reality headsets that provide an immersive experience in which the physical surroundings are not visible when wearing the VR headset 102 and the entire viewed content is the generated artificial visual content (i.e., virtual scene), as well as augmented reality headsets in which the VR headset 102 has transparency allowing for the wearer to see the physical surroundings with the generated virtual scene being superimposed on the physical surroundings.

As shown in FIG. 1, the VR headset 102 includes various hardware components, including but not limited to eye tracking hardware 106, a display device such as screen 108, one or more sensors 110, optionally one or more add-on hardware components 112. The eye tracker 106 typically includes a light source such as LEDs, e.g. infrared LEDs, illuminating the left and right eyes and cameras or sensors (e.g., infrared-sensitive cameras or sensors) that image the eyes. The eye tracker 106 tracks eye position and optionally also pupil size, for example using bright-pupil or dark-pupil eye tracking. In another embodiment, the eye tracker 106 employs passive light, for example using visible light generated by the screen 108. Other known eye tracking technologies are also contemplated for use as the eye tracker 106. The eye tracking hardware 106 can be provided as a single chip, such as an application-specific integrated circuit ("ASIC"), which includes an electronic processor 114, nontransitory local memory 116, and instructions 118 for processing the data generated from the tracking hardware. The instructions 118 may include one or more software components, here illustrated as eye tracking component software 120.

More particularly, eye tracking component software 120 includes computer program code configured to locate, measure, analyze, and extract data from a change in one or more features of a test subject's eyes. The change in one or more features of the test subject's eyes is generally induced by a moving object to be tracked by the test subject's eyes in a virtual scene displayed on the screen 108 of the VR headset 102.

Other changes in the one or more features of the test subject's eyes can be induced, for example, by changing one or more virtual environmental conditions of the virtual scene displayed on the screen 108 of the VR headset 102 (e.g., the brightness of the virtual scene). The local memory 116 stores the instructions 118 to implement the eye tracking software 120, and the instructions 118 are configured to perform at least part of the method illustrated in FIG. 12 (discussed in further detail below). The processor 114, being in communication with the memory 116, executes the instructions 118 to perform the aforementioned part of the method illustrated in FIG. 12.

The data generated during processing by the eye tracking hardware 106 and software 120 can be stored in non-transitory data memory 132, which is separate or integral with local memory 116. In addition, or alternatively, data generated by the eye tracking hardware 106 and software 120 can be output to the host computer 104 for further processing, via input/output (I/O) device 122.

As illustrated in FIG. 1, the raw data stored in data memory 132 includes, for example, timestamp 162, eye gaze origin 164, eye gaze direction 166, pupil position 168, and absolute pupil size 170 datasets. Data related to the screen 108, the one or more sensors 110, and the optional one or more add-on hardware components 112 can be similarly stored in data memory 132 and/or output to host computer 104. Hardware components 106, 108, 110, 112, 114, 116, 122, 132 of the VR headset 102 can be communicatively connected by a data/control bus 124.

In some embodiments, the one or more additional sensor components 110 of the VR headset 102 include but are not limited to cameras 110a (which may be the infrared-sensitive sensors of eye tracking hardware 106 or may be additional cameras), body tracking sensors 110b, infrared ("IR") sensors 110c, G-sensors 110d, gyroscopes 110e, proximity sensors 110f, and electrodes 110g for obtaining electroencephalogram (EEG) data. The cameras 110a further optionally include a video recording device which records eye movement during testing.

The host computer 104 typically includes a variety of additional hardware components not shown in FIG. 1, such as an electronic processor, non-transitory main and data memories, software instructions, input/output (I/O) devices, data/control buses etc., and the like. All such hardware components of host computer 104 are typically communicatively connected by the data/control bus. Moreover, the electronic processor of the host computer 104 is in communication with the non-transitory main memory and executes instructions stored therein. The instructions generally include several software components which may operate in conjunction with the one or more software components from instructions 118 of the VR headset 102.

The various non-transitory memories, e.g. the local memory 116, the data memory 134, and the main and data memories of the host computer 104, may be variously embodied, for example as an electronic memory (e.g. flash memory or solid state drive, i.e. SSD), a magnetic memory (e.g., a magnetic hard drive), an optical memory (e.g. an optical disk), various combinations thereof, and/or so forth. Moreover, it will be appreciated that the various software may be variously stored in one or any combination of the various memories, and that the disclosed impairment assessment processing may be performed by one or more of the on-board processor 114 of the VR headset 102 and/or the processor of the host computer 104.

The processor and software components of host computer 104 are generally configured to analyze, extract, calculate, and/or correlate information from the raw data generated by the eye tracking hardware 106 and stored in data memory 132 of the VR headset 102. The data memory of the host computer 104 can be separate or integral with the main memory and stores data produced during execution of the instructions by the processor. The data stored in the main and data memories of the host computer 104 can be output (via one or more I/O devices) as impairment indicator information 140. An impairment prediction 142 (i.e., degree and/or probability of impairment), based on the impairment indicator information 140, may also be output via the one or more I/O devices of the host computer 104.

The VR headset 102 is generally communicatively connected with the host computer 104 by a wired or wireless link 144. The wired or wireless link 144 is generally configured to interface with the one or more I/O devices of the host computer 104 and may include the Internet, Bluetooth, USB, HDMI, and/or DisplayPort, for example. Thus, all the data stored in memory 116 which has been generated by the eye tracking hardware 106 of the VR headset 102 can be communicated via wired or wireless link 144 and received by the one or more I/O devices of the host computer 104.

In addition, the VR headset 102 can optionally be configured to run the software components of the host computer 104 mentioned above and described in further detail below. Such a configuration for the VR headset 102 may be desirable if the headset needs to operate in a stand-alone manner without host computer 104, e.g. during a traffic stop, while deployed away from the host computer 104 in the field (i.e., concert, sporting event, political event, or other type of venue or event), and the like.

The software components of the VR headset 102 or host computer 104 may include code, which when executed by the processor 114 (or host computer 104 processor) causes the corresponding processor to communicate with a user or test administrator via the screen 108 or display device 105 of the host computer 104. For example, once instructed by a user or test administrator, a user interface of the host computer 104 can cause screen 108 of the VR headset 102 (or host display device 105) to display any number of virtual scenes. Each virtual scene generally includes one or more dynamic component(s) configured to generate a change in one or more features of a subject's eye(s). As discussed above, the eye tracking component 106 of the VR headset 102 is configured to locate, measure, analyze, and extract data from the change in one or more eye features which has/have been induced by the virtual scene displayed on the screen 108 by the user interface. In addition, when the host computer 104 includes a separate display device 105, real-time test data can be shown on the display device and include, for example, graphical representations of eye position, graphs, charts, etc.

The software components of the VR headset 102 or host computer 104 may further include a testing component having code, which when executed by the electronic processor 114 (or host computer 104 electronic processor) causes the corresponding processor to store and retrieve information from memory which is necessary to perform various impairment tests, including but not limited to one or more of: lack of convergence ("LOC"), horizontal and vertical gaze nystagmus ("HGN" and "VGN", respectively), pupil dilation, color sensitivity, and targeting. The type of information typically retrieved with the testing program includes, but is not limited to: predetermined testing parameters/equations for each impairment test; and, the raw data generated by the eye tracking component 106 which can be stored in data memory 132 of the VR headset 102 or in the memory of host computer 104.

Another software component which the VR headset 102 or host computer 104 can optionally include is an impairment testing component having code, which when executed by the processor 114 (or host computer 104 processor)

causes the corresponding processor to retrieve user data on the subject undergoing the test. User data can be input through one or more peripheral devices communicatively connected to the VR headset 102 and/or host computer 104. Once the information is retrieved, the testing component inputs the information into the testing parameters/questions to determine output parameter values for each impairment test performed. The parameter values output from the testing component will subsequently be used to determine a test subject's level of impairment and can optionally be stored in data memory 132 of the VR headset 102 or in the memory of host computer 104.

The software components of the VR headset 102 or host computer 104 may further include a processing/comparison software component having code, which when executed by the processor 114 (or host computer 104 processor) causes the corresponding processor to correlate the retrieved testing parameters and associated output values from the testing component with a corresponding baseline standard of impairment/non-impairment and its associated parameter values. More particularly, each of the testing parameters utilized by the testing component are compared with local data containing predetermined or premeasured baseline standards and corresponding parameter values of impairment/non-impairment. If a match is found between the testing parameters and the baseline standards, the associated baseline parameter values, or a representation thereof, is/are extracted. The local data of baseline standards and the correlations made by the processing/comparison component can optionally be stored in data memory 132 of the VR headset 102 or in the memory of host computer 104.

In some configurations, after the processing/comparison component has made correlations, an optional decision software component of the VR headset 102 or host computer 104 is utilized. The decision software component includes code, which when executed by the processor 114 (or host computer 104 processor) causes the corresponding processor to predict a level of impairment (that is, predict a probability and degree of impairment of a test subject), based on the correlated parameter values determined by the processing/comparison component. That is, for any testing parameter and baseline standard being correlated by the processing/comparison component, if the testing parameter output value(s) exceeds one or more thresholds (e.g., value(s) over a period of time, too many high and/or low values, total value too high/too low, etc.) set for the corresponding baseline output value(s), the decision component may output a prediction 142 that the test subject is impaired at an estimated degree.

The impairment prediction 142 of the decision component can optionally be stored in data memory 132 of the VR headset 102 or in the memory of host computer 104. In addition, or alternatively, the impairment prediction 142, or a representation thereof, can be output to the test subject or test administrator via the output component. The output component can output the impairment prediction 142 alone or together with the correlated baseline standards, associated baseline parameter values, testing parameters, and associated testing parameter values.

In other configurations, the decision software component is not utilized such that neither the VR headset 102 nor host computer 104 will make an impairment prediction. In such embodiments, a user or administrator of the VR headset 102 and/or host computer 104 may prefer to make his/her own impairment prediction based on a review of the impairment indication information 140.

In any event, the output component of the VR headset 102 or host computer 104 includes code, which when executed by the processor 114 (or host computer 104 processor) causes the corresponding processor to output one or both impairment indication information 140 and impairment prediction 142, or a representation thereof. More particularly, information 140 and prediction 142 are output to the user interface, such that the screen 108 of the VR headset 102 and/or display device 105 of the host computer 104 can display the information to the test subject or test administrator. Moreover, the eye data saved for each test subject in information 140 is saved in at least one of the memory components of the VR headset 102 or host computer 104.

Generally, the information 140 is saved in an appropriate format which enables the loading and replaying of test data files for any test subject. If desired, the entire test for a test subject can be replayed using the animated eyes 149 shown on the display device 105 of the host computer 104 as described above. In some particular examples, the information 140 can be saved to memory in the XML file format. In other examples, the information 140 can be saved to memory as a report file written in markdown, such as an R Markdown file. Markdown files like R Markdown are written in plain text format containing chunks of embedded R code configured to output dynamic or interactive documents. The R Markdown file can be knit, a process where each chunk of R code in the file is run and the results of the code are appended to a document next to the code chunk. R Markdown files can also be converted into a new file format, such as HTML, PDF, or Microsoft Word, which preserves the text, code results, and formatting contained in the original R Markdown file.

The processing/comparison component described above can further include computer program code configured to direct the processor 114 (or processor of the host computer 104) to compare the output values and/or baseline standards with one or more confidence metrics stored in the local data-store. For example, one confidence metric includes historical data of each individual impairment test result which is accessed by the processing/comparison component to assess the confidence of an indication of impairment. Such historical data could further include drug class identification results with probability or percent matches associated with one or more drug classes. Each of the testing parameters utilized by the testing component are compared with these confidence metrics in the local data-store, and if a match is found between the testing parameters/baseline standards and the confidence metrics, the associated confidence metric, or a representation thereof, is/are extracted and are optionally stored in data memory 132 of the VR headset 102 or in the memory of host computer 104.

Figure 2A:
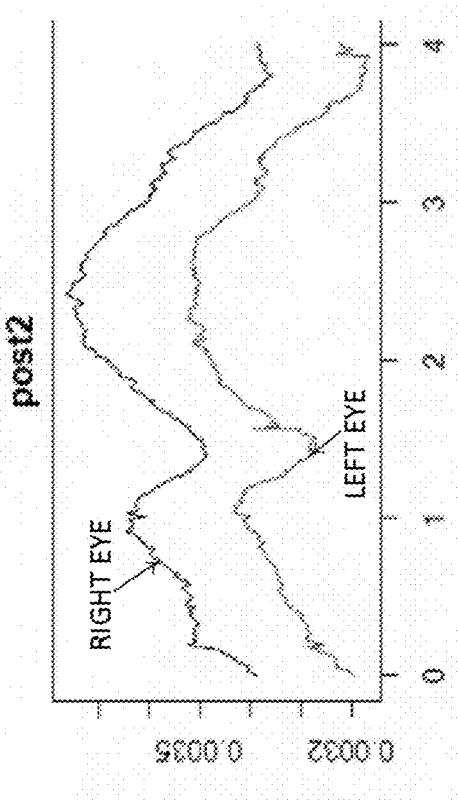
FIGS. 2A-5 are illustrations of various charts and plots showing the data obtained from an equal pupil test and the results thereof.
Figure 2A:
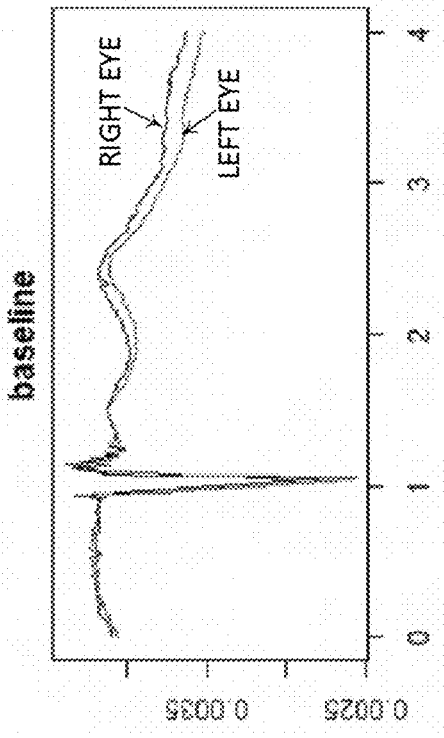
Figure 2A:
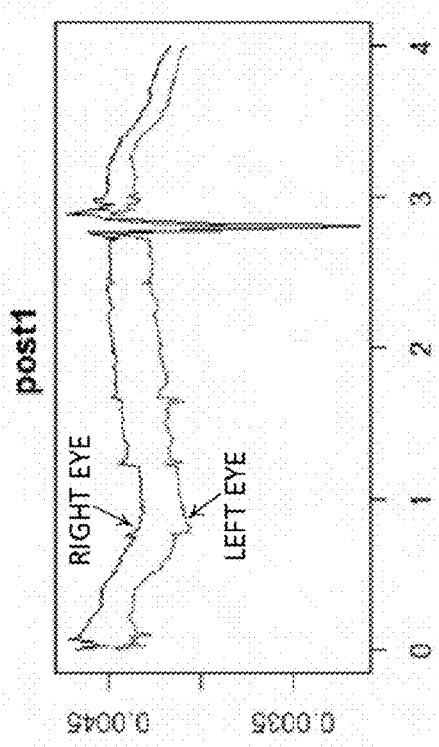
Figure 2B:
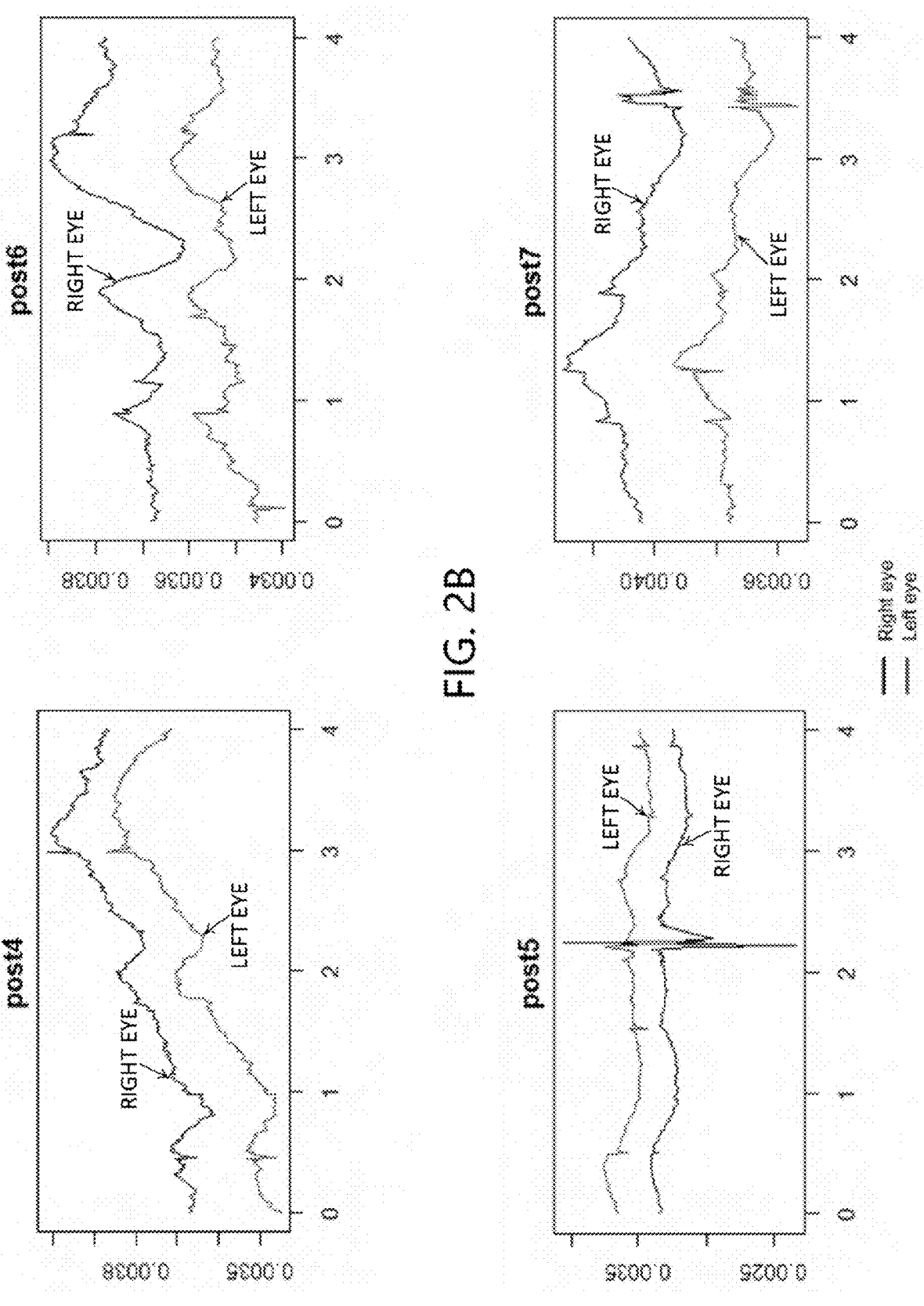

In addition, or alternatively, the baseline standards, associated baseline parameter values, and associated confidence metrics from the local data-store that have been matched with the testing parameters and associated values output from the testing component are output as part of impairment indication information 140. As illustrated in FIGS. 2A-2B, the baseline parameters and testing parameters, as well as the values associated therewith, can be related to one or more of a timestamp 172, test state 174, scene settings 176, left pupil size 178, right pupil size 180, eye gaze to target cast distance 182, eye gaze to target cast vertical angle 184, eye gaze to target cast horizontal angle 186, eye horizontal angle to normal 188, eye vertical angle to normal 190, distance between eye focus points 192, eye position 194, and eye jitter 196. These testing parameters are discussed in greater detail below.

Some of the aforementioned testing parameters are directed to the state or status of the system 100 itself. For example, the timestamp 172 testing parameter refers to the time that each set of data originates from, measured in seconds, minutes, hours, etc. The test state 174 refers to an integer representing what part of the test is running at the time the sample is taken. For example, the integer "1" may be a test state integer indicating that a first part of the lack of convergence test ("LOC") was running at a timestamp of 30 seconds into the test.

Other testing parameters are directed toward information and data that may be useful for the aforementioned pupil size and response test, along with the color sensitivity test. For example, the scene settings 176 refers to various characteristics of the scene displayed on the screen 108 of the VR headset 102, including but not limited to scene brightness and scene colors. The brightness in the scene settings 176 is changed for the pupil response test, and specific colors in the scene settings are changed for the color sensitivity test. For example, in the color sensitivity test, VR headset 102 is configured to observe whether the test subject responds to yellow and/or blue colors. In this regard, yellow/blue color vision loss is rare and thus serves as an indicator of impairment. Left pupil size 178 refers to the size of the test subject's left pupil, measured in millimeters by the eye tracking hardware 106 and software 120. Right pupil size 180 refers to the size of the test subject's right pupil, measured in millimeters the eye tracking hardware 106 and software 120.

Some of the other testing parameters are directed toward information and data that may be useful for the aforementioned horizontal and vertical gaze nystagmus tests, as well as the lack of convergence test. For example, the eye gaze to target cast distance 182 refers to the distance between the point where the test subject is looking and the object the test subject is supposed to be looking at, measured in meters by the eye tracking hardware 106 and software 120. The eye gaze to target cast distance 182 is calculated separately for each eye, and the estimated overall point of focus with both eyes is calculated with the eye tracking software 120. The eye gaze to target cast vertical angle 184 refers to the angle between the test subject's gaze and a direct line from their eyes to the tracking object, measured in degrees on the vertical plane by the eye tracking hardware 106 and software 120. The eye gaze to target cast vertical angle 184 is also calculated for each eye and the total gaze. The eye gaze to target cast horizontal angle 186 refers to the angle between the test subject's gaze and a direct line from their eyes to the tracking object, measured in degrees on the horizontal plane by the by the eye tracking hardware 106 and software 120. The eye gaze to target cast horizontal angle 186 is also calculated for each eye and the total gaze. The eye horizontal angle to normal 188 refers to the angle of each eye's gaze relative to the forward direction of the test subject's head, measured in degrees on the horizontal plane by the eye tracking hardware 106 and software 120. The eye vertical angle to normal 190 refers to the angle of each eye's gaze relative to the forward direction of test subject's head, measured in degrees on the vertical plane by the eye tracking hardware 106 and software 120.

The remaining testing parameters mentioned above are related to eye movement in general, which may be useful for all the aforementioned impairment tests. The eye position 194 refers to the X and Y coordinate position of each of the test subject's pupils within the eye socket, measured by the eye tracking hardware 106 and software 120. The eye jitter 196 refers to the angle between each test subject's eye's direction and the direction of each eye at the last sample, measured in degrees by the eye tracking hardware 106 and software 120. Eye position 194 and eye jitter 196 information may be particularly useful for a targeting test which measures the ability to detect the presence of an object that appears in a test subject's field of view and the test subject's ability to focus their gaze on that object. The test subject is instructed to focus their gaze on the target object when detected, and the appropriate eye data is measured and recorded upon detection.

EXAMPLES

Various impairment tests were performed using a VR headset 102 according to the embodiments described above. That is, a VR headset 102 configured for detecting impairment of a test subject, as discussed above, was used at an alcohol and cannabis "wet lab", where controlled doses of alcohol and cannabis were administered to one or more volunteer test subjects. During the lab, the test subjects were asked to wear a VR headset 102 configured to act as an impairment sensor. Data was then gathered when the test subjects were sober and subsequently impaired due to alcohol and then cannabis.

One test subject was used to provide representative results for alcohol impairment (hereinafter referred to as "test subject A"), and a different test subject was used to provide representative results for cannabis impairment (hereinafter referred to as "test subject B"). Thus, the test subjects were able to provide sober baseline measurements before consuming alcohol and before consuming cannabis. The various impairments tests were then administered to test subject A at varying blood alcohol content (BAC) levels, such that measurements of alcohol impairment could be obtained. More particularly, the impairment tests were administered at a BAC of 0 (baseline), a BAC of about 0.116, and a BAC of about 0.146.

The impairment tests were next administered to test subject B at various times after smoking cannabis, such that measurements of cannabis impairment could be obtained. More particularly, the impairment tests were administered at post-cannabis smoking times in accordance with Table 1 below:

TABLE 1

| Parameters for Cannabis Impairment Test | |
| --- | --- |
| Category | Post-Smoking Times (min) |
| Base | Before smoking |
| Post 1 | 10 |
| Post 2 | 30 |
| Post 3 | 60 |
| Post 4 | 90 |
| Post 5 | 120 |
| Post 6 | 180 |
| Post 7 | 240 |

All the relevant eye and testing data was recorded by sensor software of the VR headset 102 during each test.

Nine (9) tests were administered to the test subjects using the VR headset 102. These nine tests included: (1) an equal pupil test; (2) an HGN test; (3) a pupil rebound test; (4) an HGN45 test; (5) an LOC test; (6) a Modified Romberg test; (7) a pupil size during HGN test; (8) an HGN during HGN45 test; and, (9) a targeting test. During each test, the VR headset 102 tracked both the test subject's eyes and gaze relative to an object. The results of these impairment tests from the two individual test subjects are discussed in greater detail below and are shown by the charts and plots illustrated in FIGS. 2A-60.

Equal Pupil Test

The equal pupil test was administered to both test subjects A and B to determine differences in pupil size which may be indicative of impairment. The VR headset 102 induced changes in pupil size by exposing both test subjects to a bright light and measuring the change in pupil size. The results of the equal pupil test are shown in FIGS. 2A-5. The respective right and left pupils of both test subjects A and B were used to obtain the results shown in the charts of FIGS. 2A-2B and 4 and the boxplots of FIGS. 3 and 5.

Figure 4:
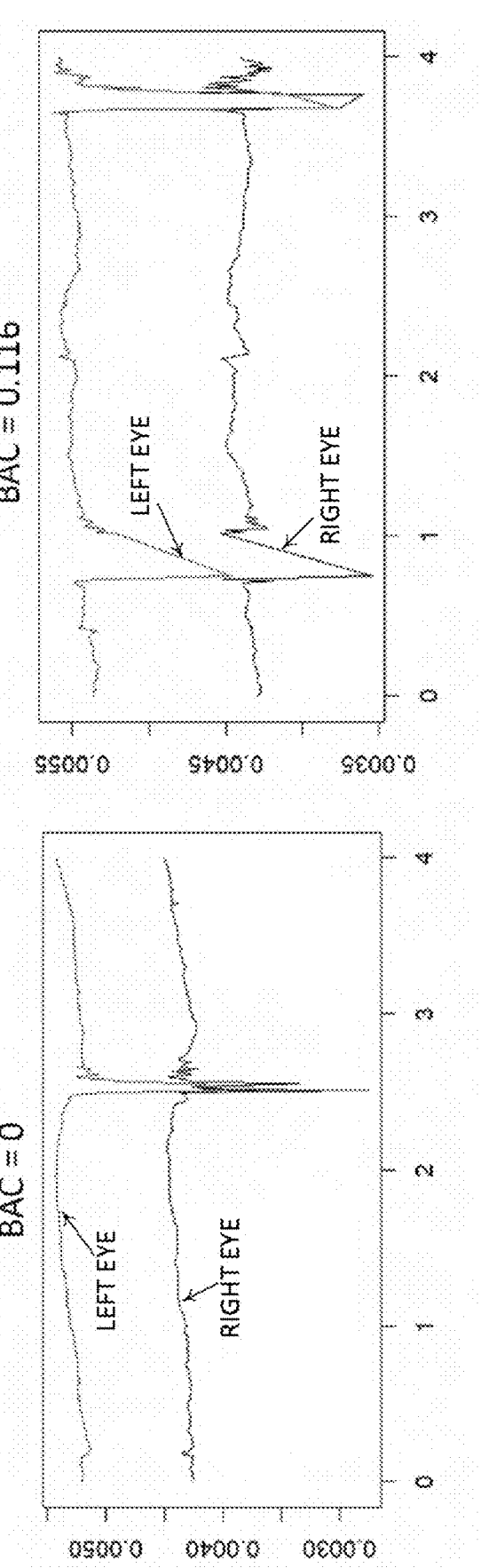
Figure 4:
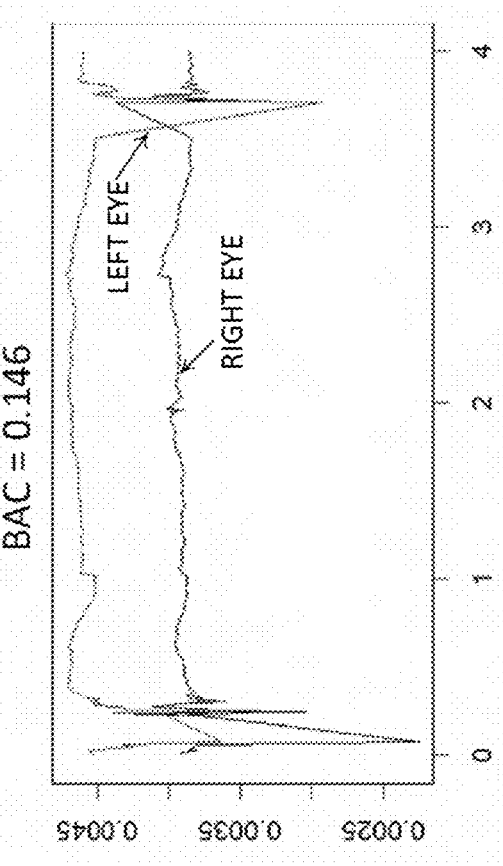

The differences between right and left eye pupil sizes were determined by subtracting left pupil size from right pupil size at each second interval shown on the X-axes of FIGS. 2A-2B and 4. Then, the absolute value was taken so that all values are positive.

Figure 3:
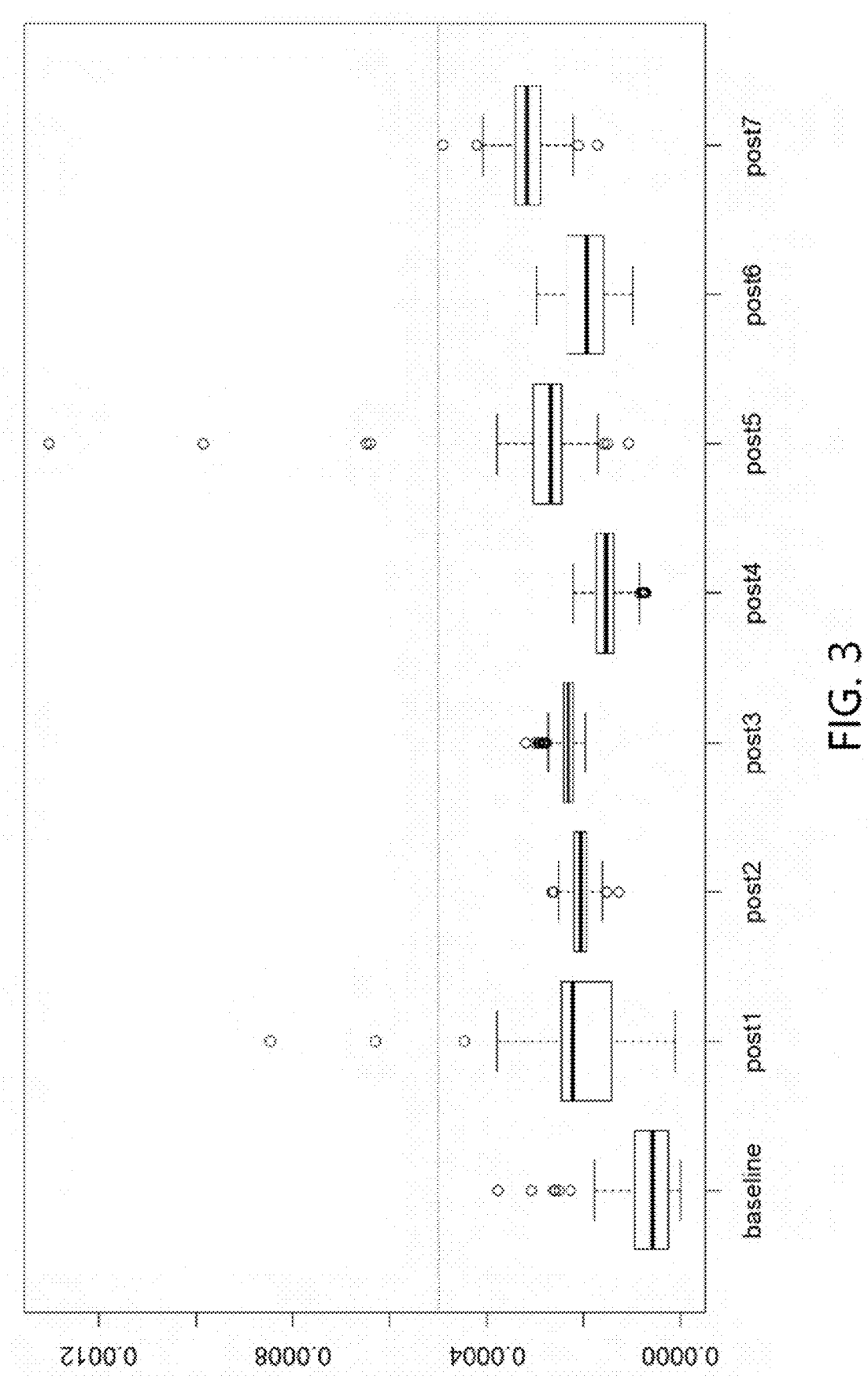
Figure 5:
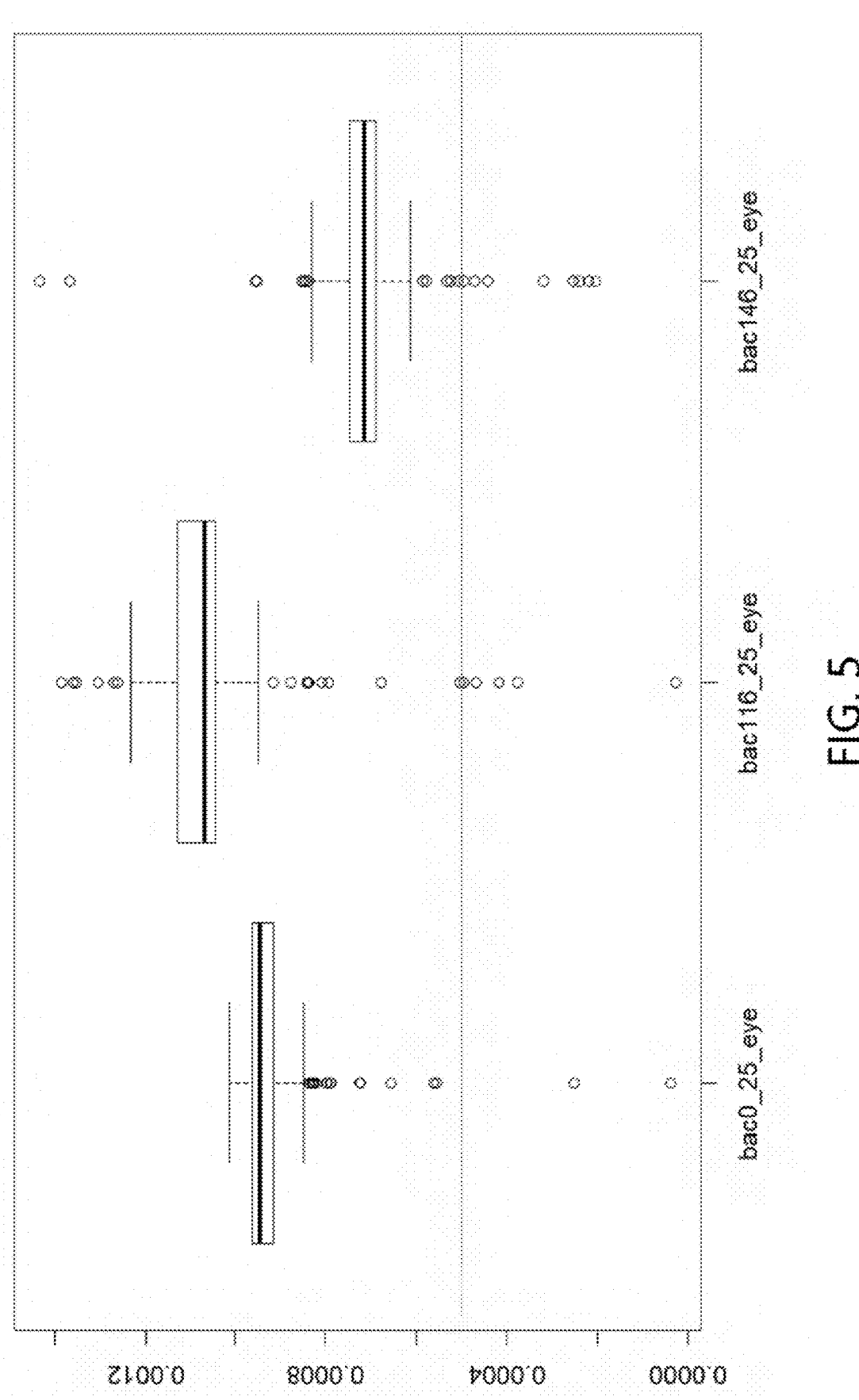

The boxplots of FIGS. 3 and 5 show the distribution for the absolute value of the difference in pupil size over time. In FIG. 3, for each post from baseline to post7, and in FIG. 5, for each BAC level of 0, 0.116 and 0.146, thick lines represent median pupil size, boxes represent 25-75% of the pupil size data (i.e., the interquartile range), and open circles represent outliers. Moreover, the red dotted line in each plot is a known value taken from the literature for a normal pupil size difference (i.e., 0.0005 m).

The results of the equal pupil test shown in the charts and plots of FIGS. 2A-5 are representative of the type of information output as part of the impairment indication information 140 described above.

Equal Pupil Test Results

With reference to the boxplot of FIG. 3, no median pupil size difference was found which was larger than what is considered normal for test subject B. Since none of the median pupil size differences were larger than normal, it was determined that these results may be specific to test subject B.

In the boxplot of FIG. 5, a median pupil size difference was found for each BAC level which was larger than what is considered normal for test subject A. However, since the larger pupil size difference occurred in the baseline 0 BAC level as well as the 0.116 and 0.146 BAC levels, it was determined that these results may be specific to test subject A.

HGN Tracking Test

Figure 10:
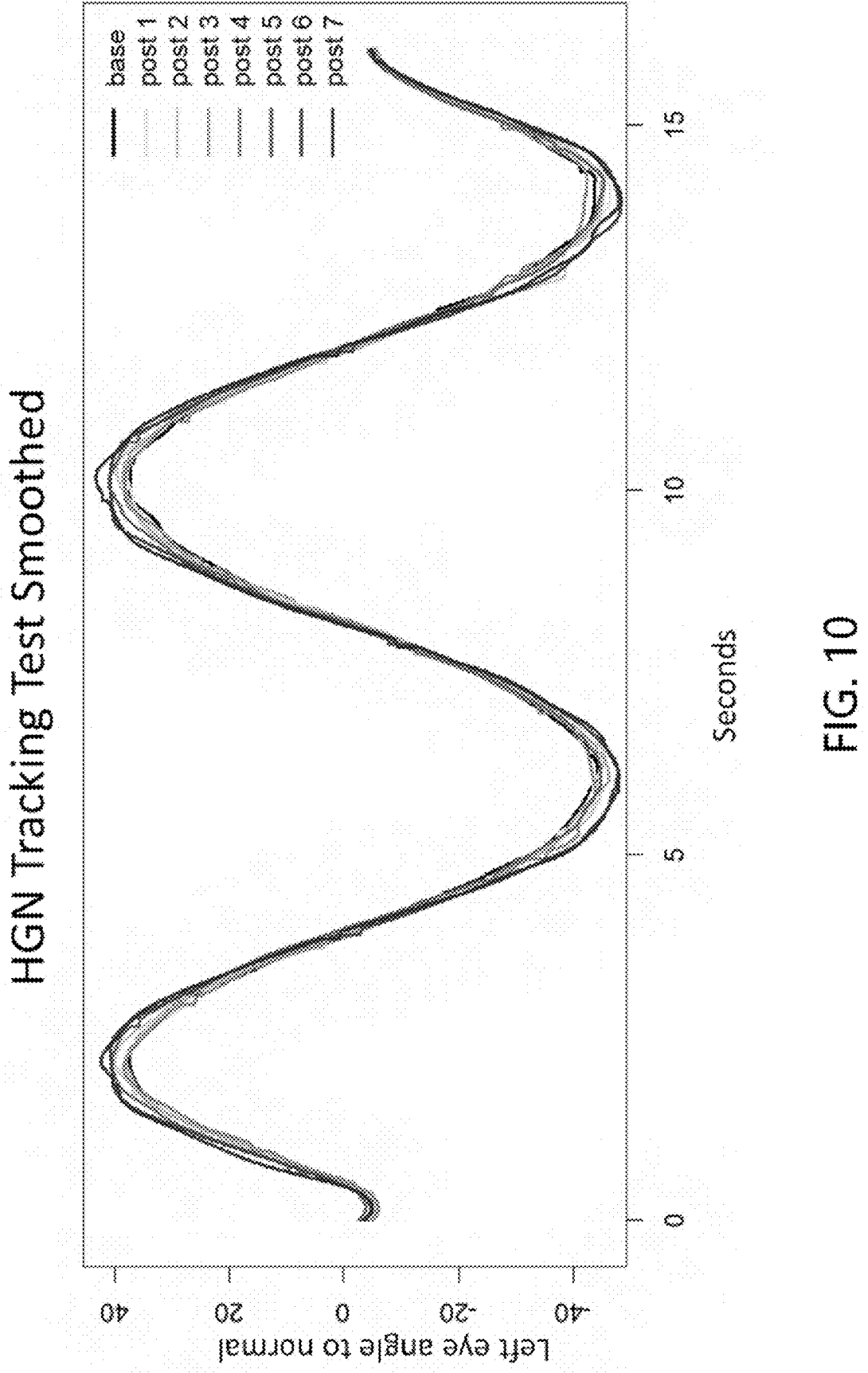
Figure 11:
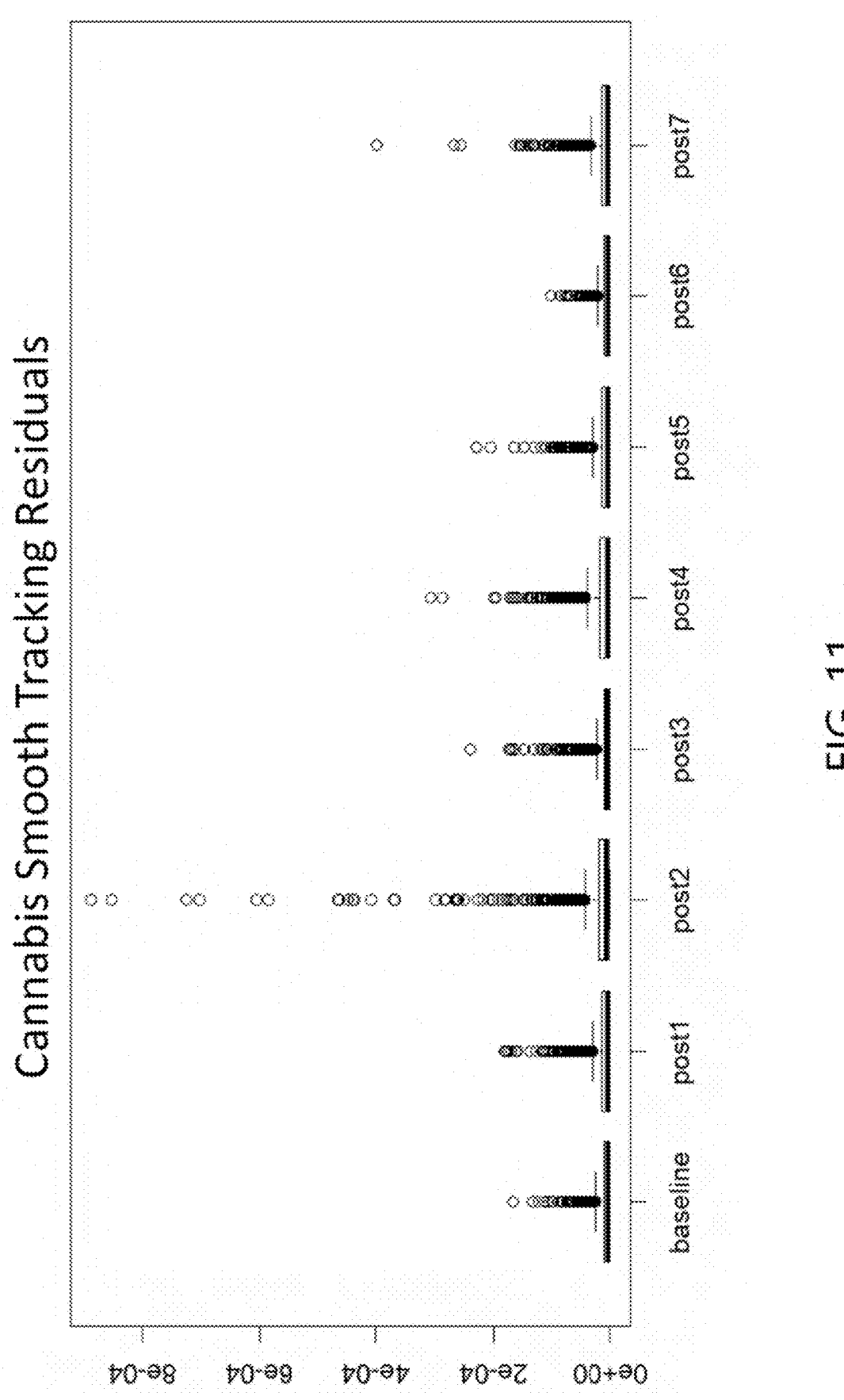

The HGN tracking test was administered to both test subjects A and B to determine whether nystagmus occurred in the test subjects' eyes which may be indicative of impairment. The VR headset 102 performed the HGN test by moving an object to the edge of the test subject's vision to induce nystagmus or jitter in the subject's eyes and tracking the response. The results of the HGN test are shown in FIGS. 6-11, where FIGS. 6-9 show the results from alcohol for test subject A and FIGS. 10-11 show the results from cannabis for test subject B.

Nystagmus was determined from the HGN Tracking test results for each test subject by using the left eye angle to normal variable defined above (the right eye could also be used). The goal of the HGN tracking test is to quantify how smoothly each test subject can track a target displayed by the VR headset 102. Smoother tracking results are assumed to be indicative of less impairment and jittery tracking results are assumed to be indicative of greater impairment.

Figure 6:
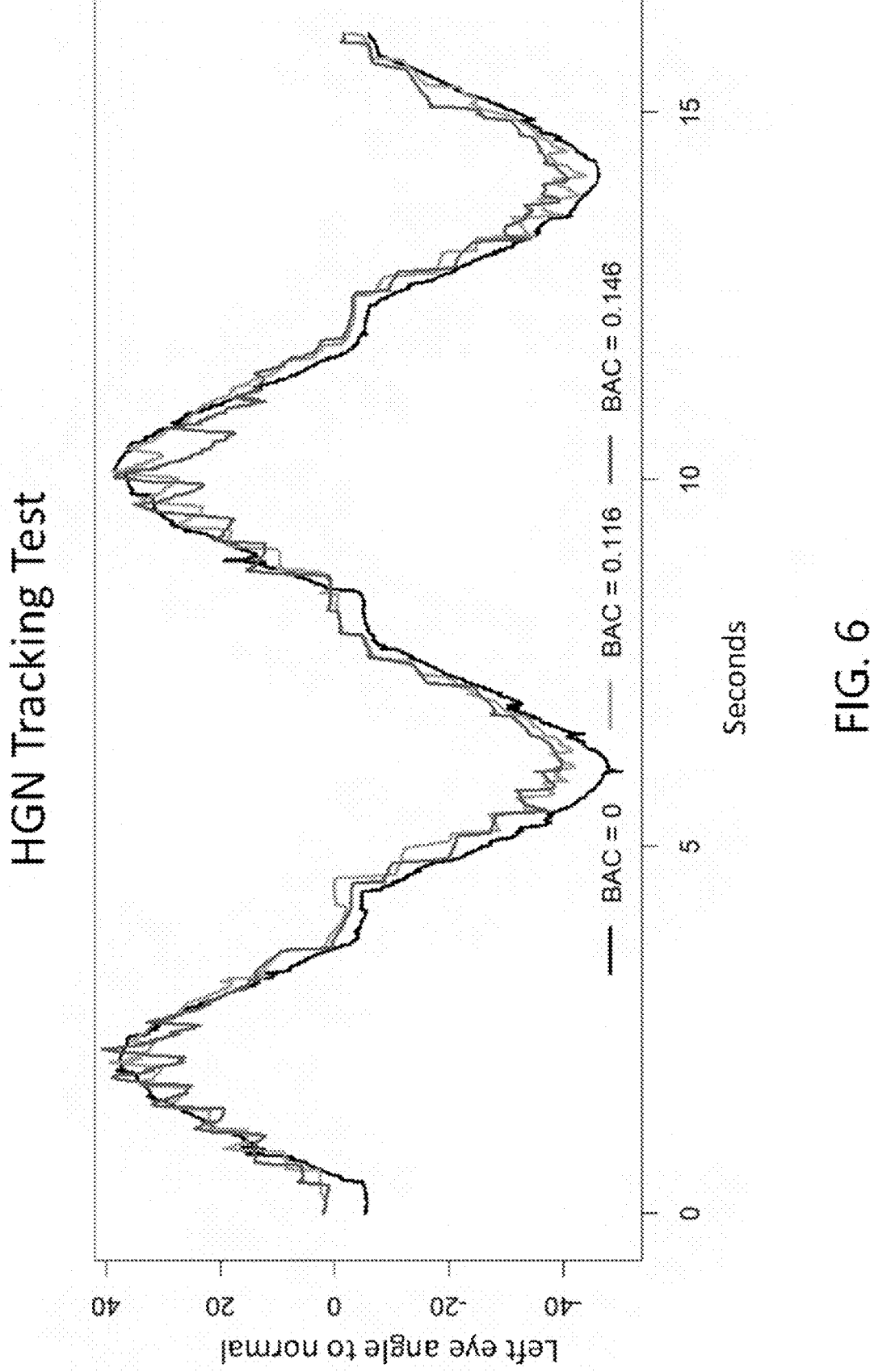
FIGS. 6-11 are illustrations of various charts and plots showing the data obtained from a horizontal gaze nystagmus (HGN) test and the results thereof.
Figure 7:
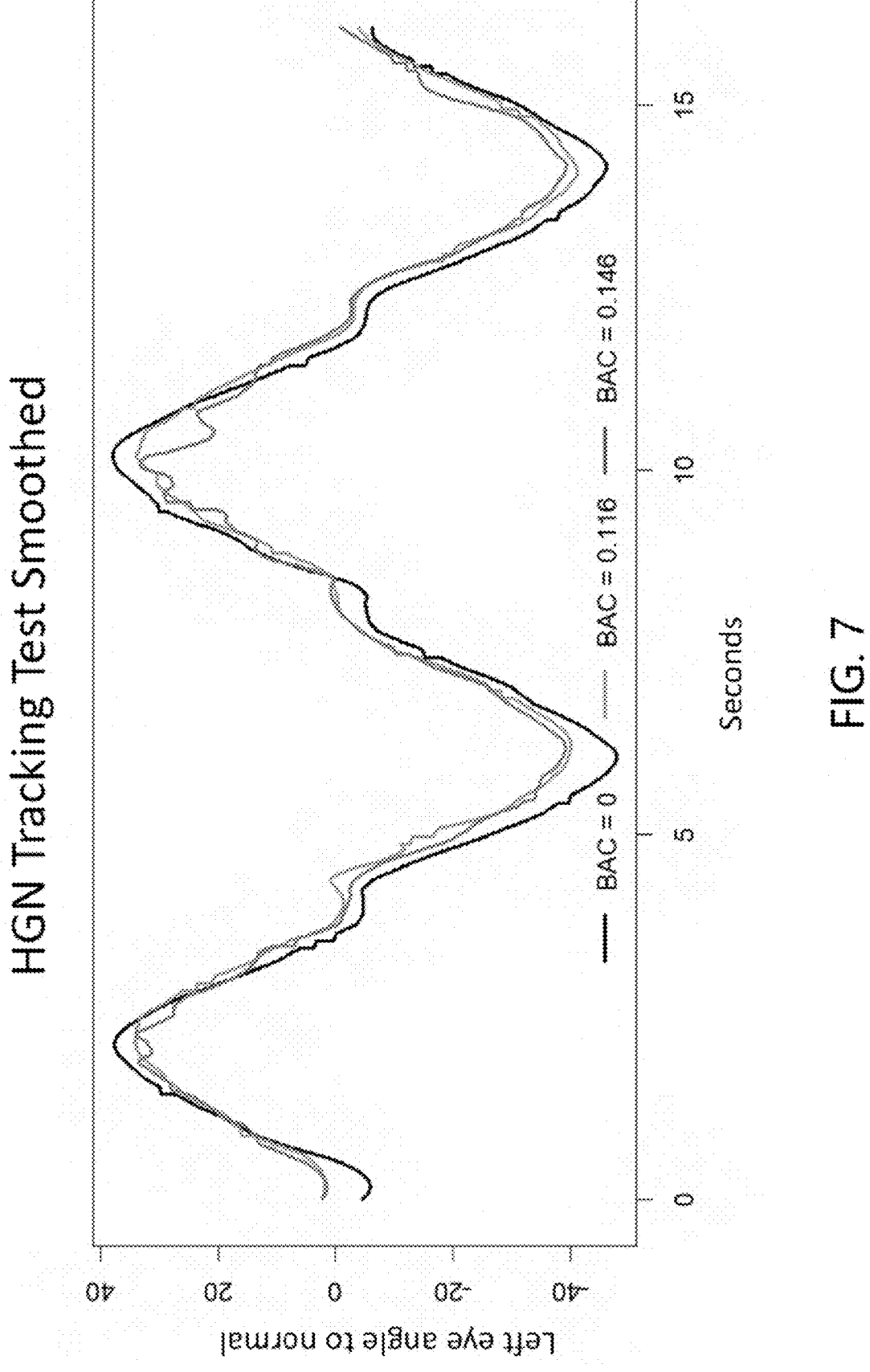
Figure 8:
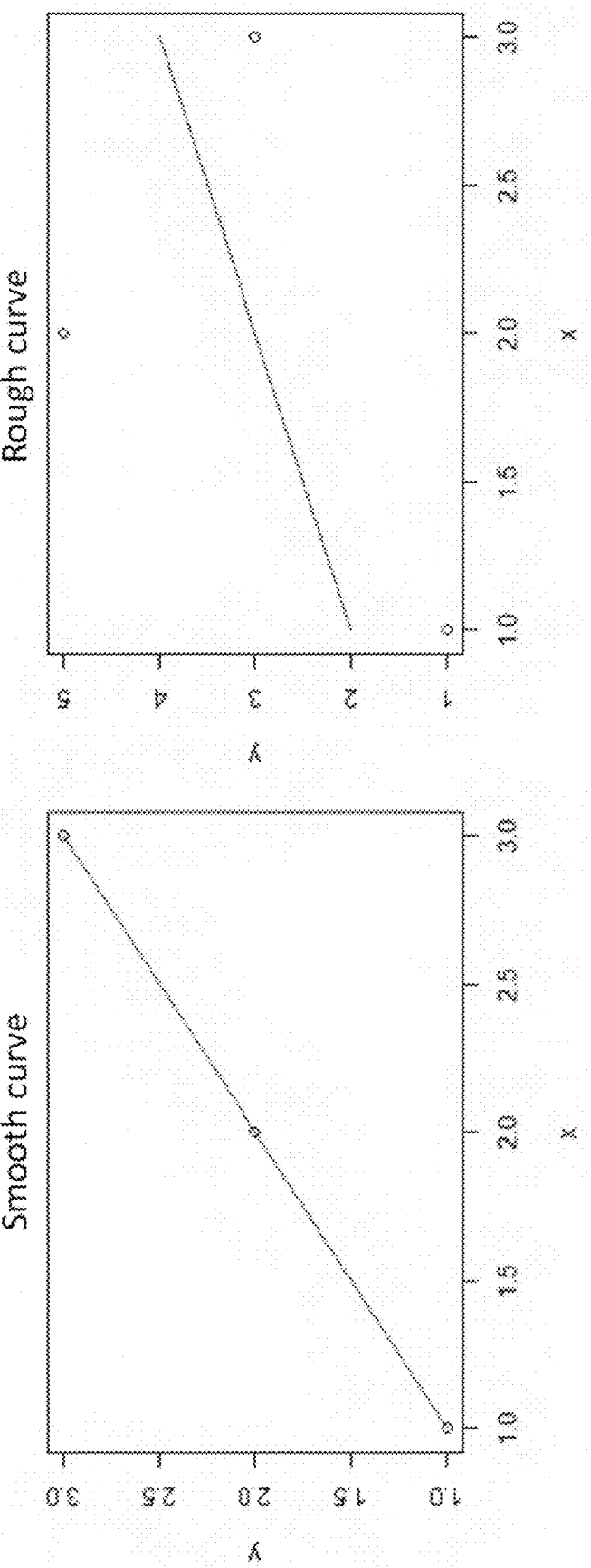

The raw data obtained during the HGN tracking test for test subject A is provided in the chart of FIG. 6 for demonstration purposes. The raw data from the HGN tracking test for test subject B is not shown but would appear similar to the chart in FIG. 6. In FIGS. 7 and 10, the data was smoothed for both test subjects A and B, respectively, using a Loess smoothing window at a length 0.05 seconds. Such smoothing is beneficial to account for irregularities due to blinking, for example.

Next, a line was fit through every 3 points of the smoothed curve. An exemplary smooth curve which fits through all 3 points is shown in the left-side chart of FIG. 8 and an exemplary rough curve which misses all 3 points is shown in the right-side chart of FIG. 8. The deviation between the fitted line and the points from the smoothed curve was then measured, and these deviations are called residuals. The residuals for test subject A are shown in the boxplot of FIG. 9 and the residuals for test subject B are shown in the boxplot of FIG. 11.

The results of the HGN tracking test shown in the charts and plots of FIGS. 6-11 are representative of the type of information output as part of the impairment indication information 140 described above.

HGN Tracking Test Results

Figure 9:
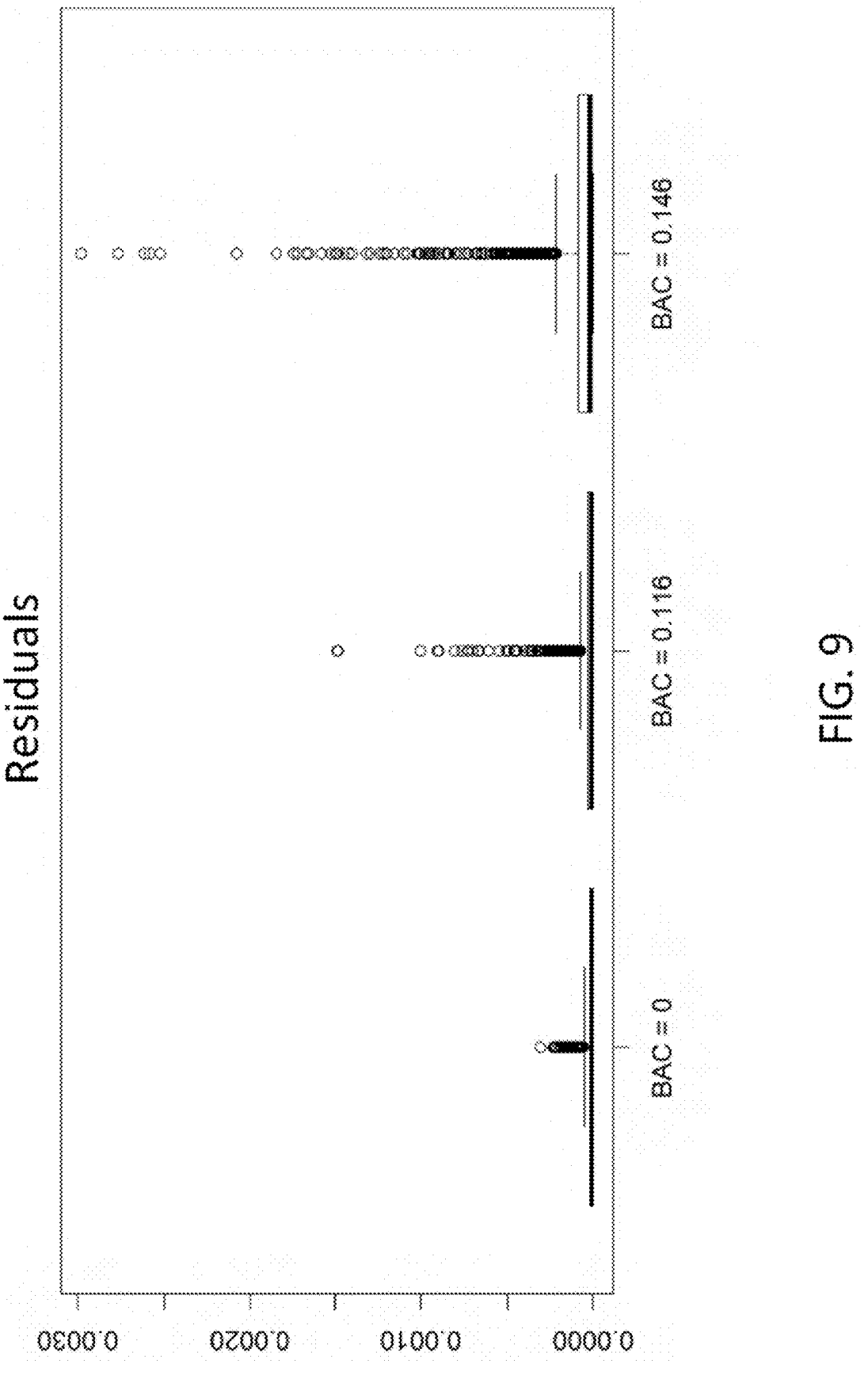

As shown in the boxplot of FIG. 9, the value of the residuals increases as the BAC level increases in test subject A. More particularly, this effect can be observed in the boxplot of FIG. 9 by an increase in the median residual value and an increase in the residual outliers. In other words, as BAC increased, it became more difficult for test subject A to smoothly track the object displayed by the VR headset.

As shown in the boxplot of FIG. 11, the relationship between smooth object tracking and post-smoking time is not clear from test subject B. Based on the large number and high values of outliers seen in Post2 of FIG. 11, it appears that test subject B experienced the most difficulty smoothly tracking an object at this time.

Pupil Rebound Test

The pupil rebound test measures the reaction to light for both test subjects by examining how their pupils responded to changing light intensities. This was conducted by putting each test subject in a low light condition for a period of time, then quickly shining a bright light into the eyes, thereby causing the pupils to constrict. Only the left pupil size was used for this test, but the right eye could also be used.

Figure 12:
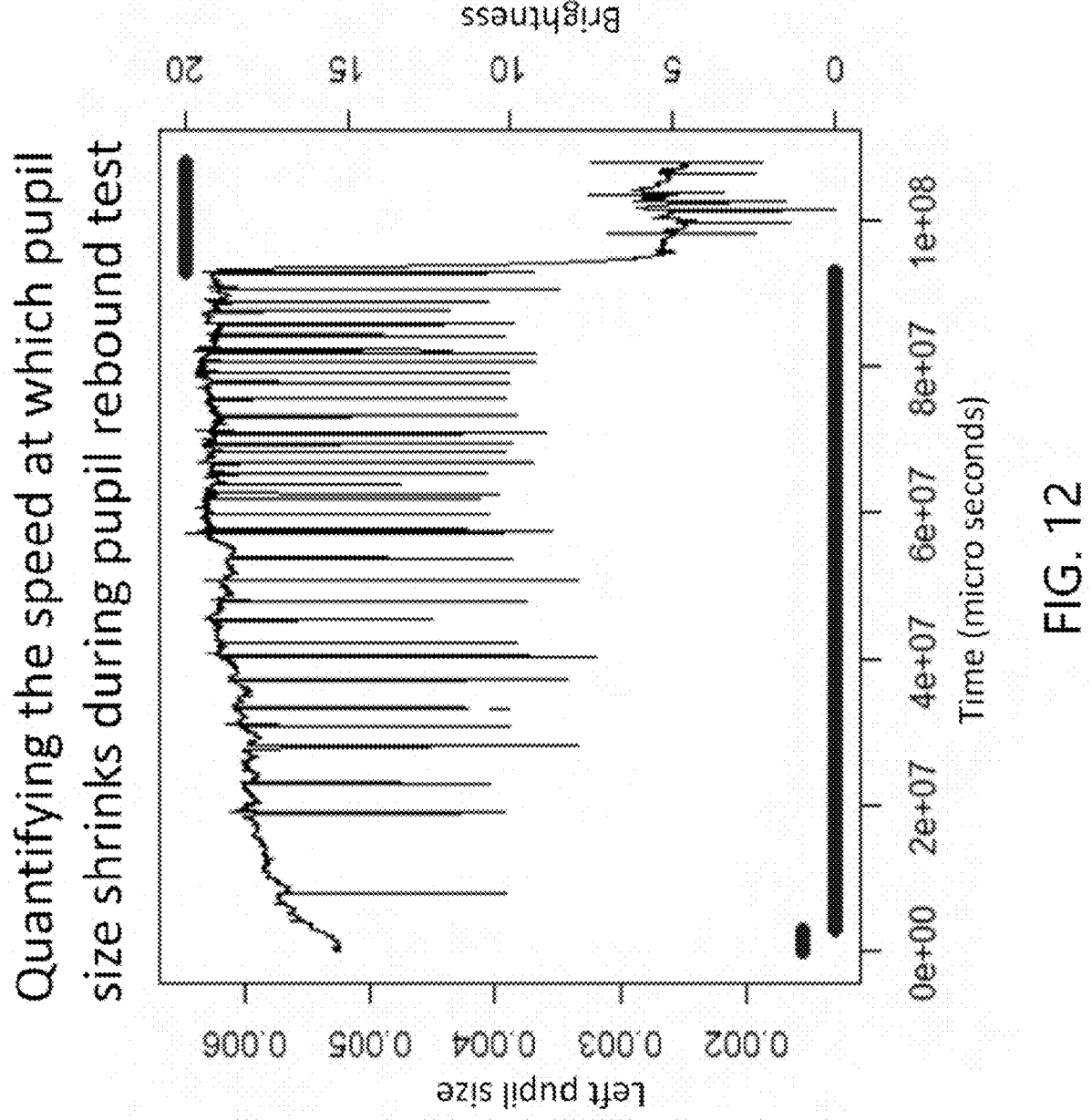
FIGS. 12-18 are illustrations of various charts and plots showing the data obtained from a pupil rebound test and the results thereof.
Figure 13:
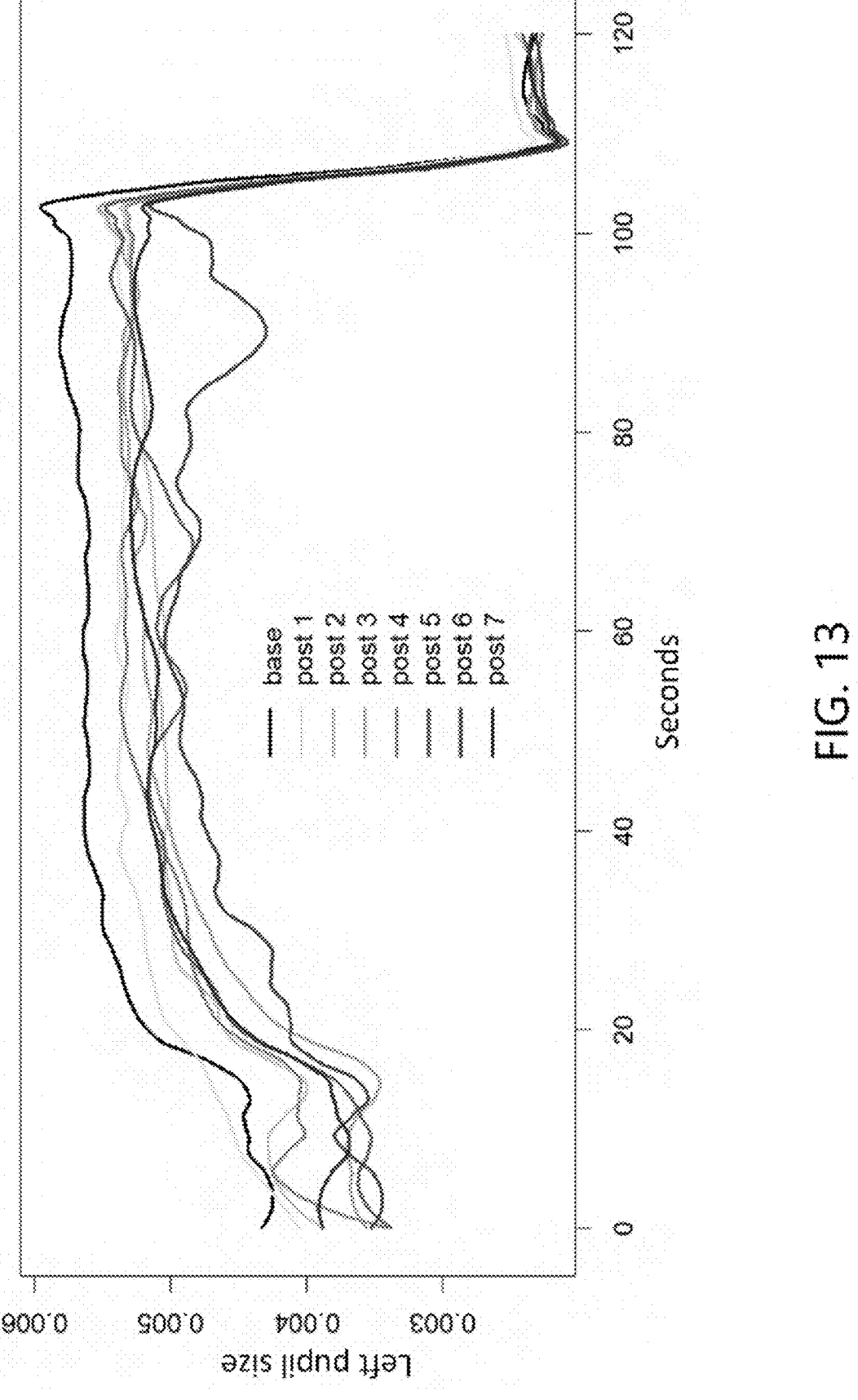

As shown in the exemplary chart of FIG. 12, the pupil rebound test examines the resting pupil size in both low light and bright light conditions, as well as the rate of change of the pupil size when exposed to light. This raw data is then analyzed to estimate pupil rebound speed, which is assumed to decrease during the change from dark to bright light as the level of impairment increases.

Figure 15:
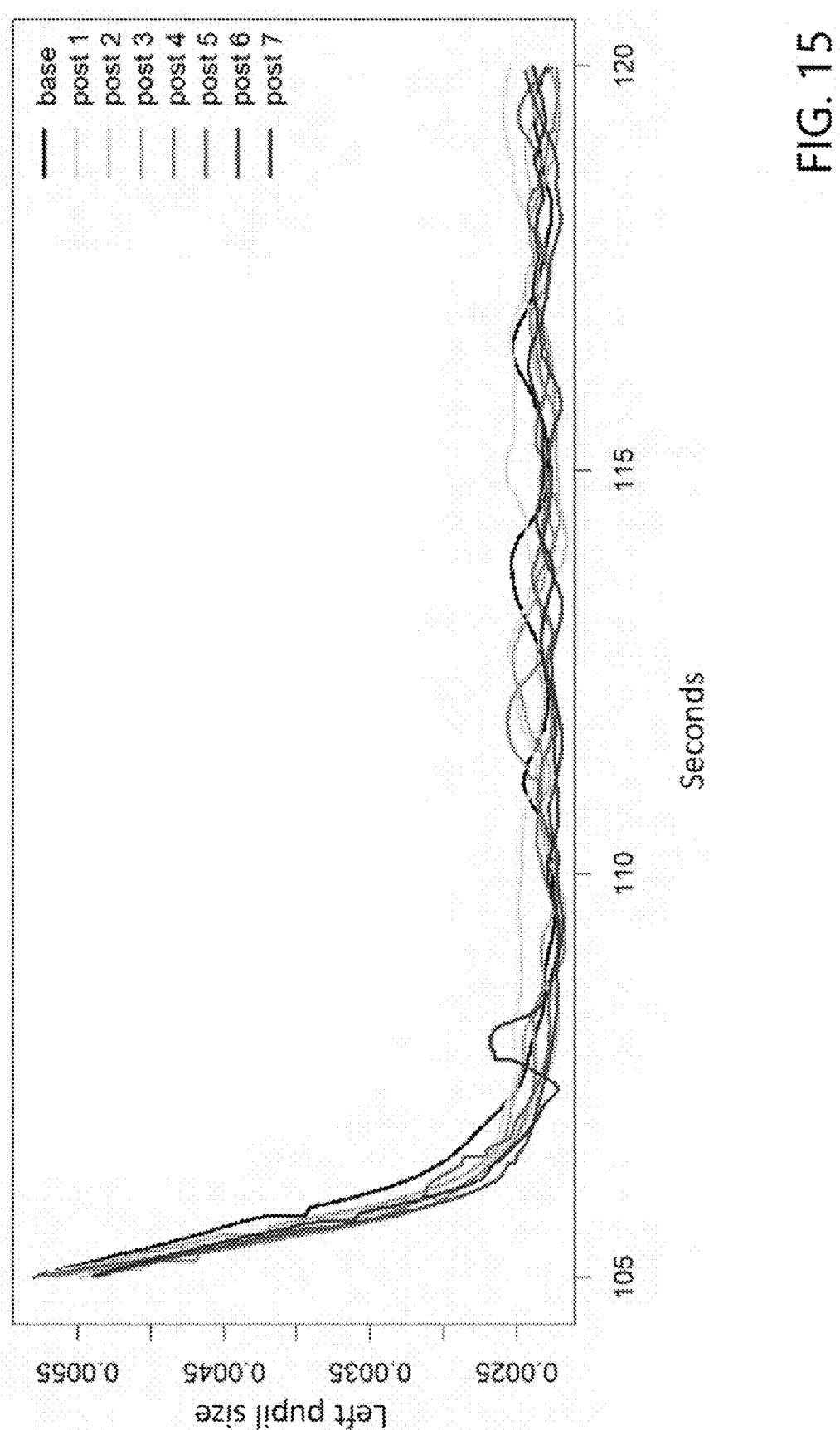
Figure 16:
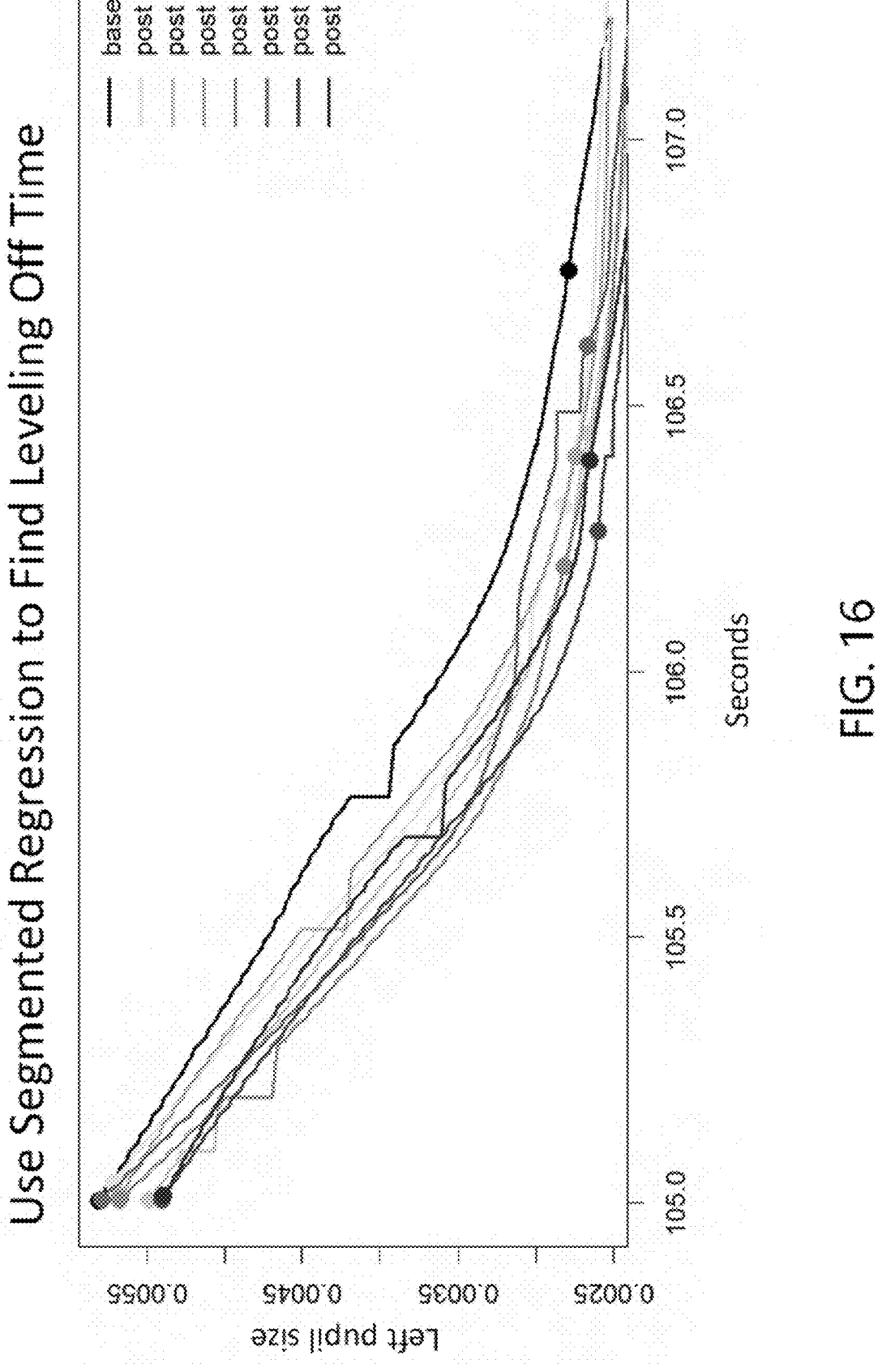
Figure 17:
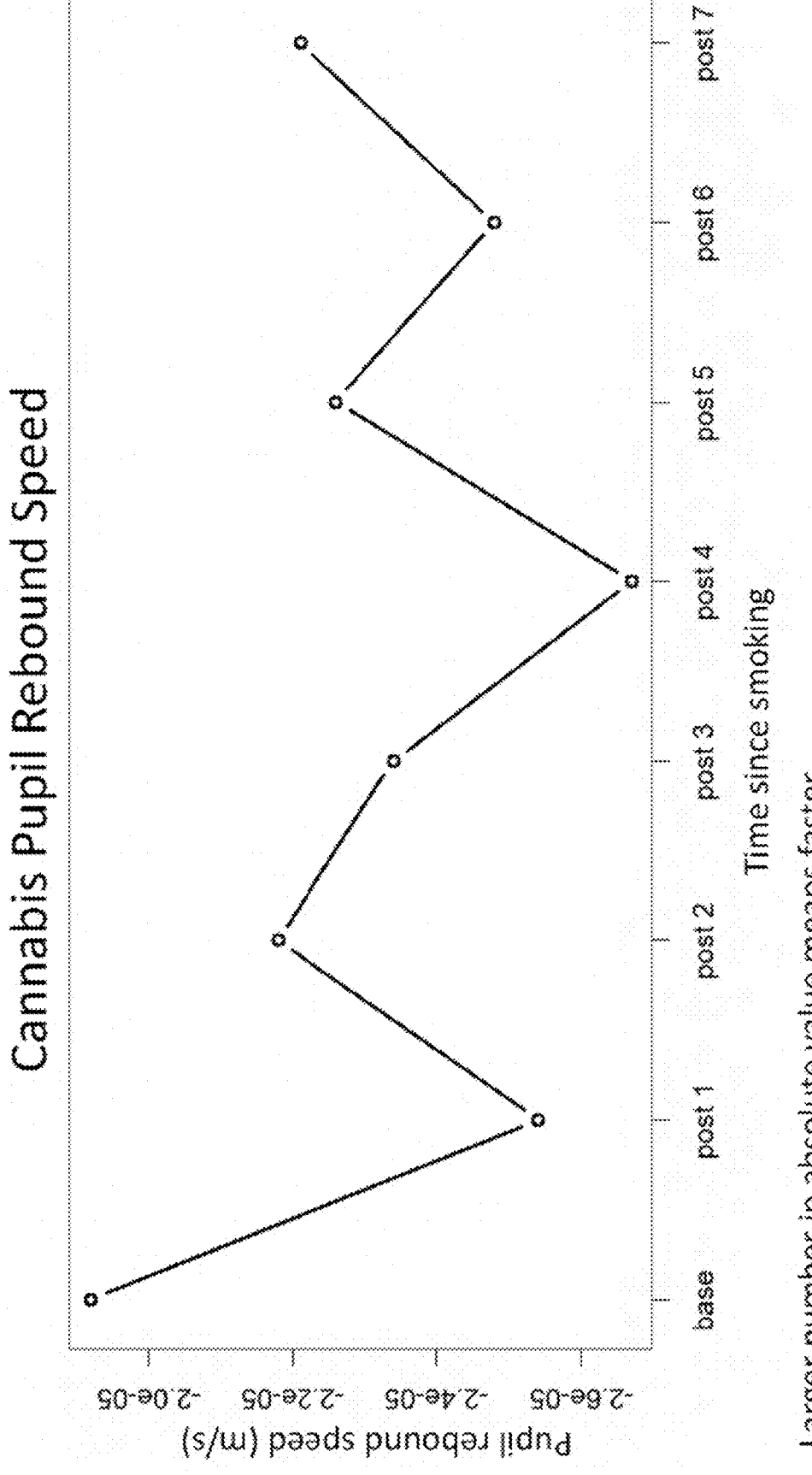
Figure 18:
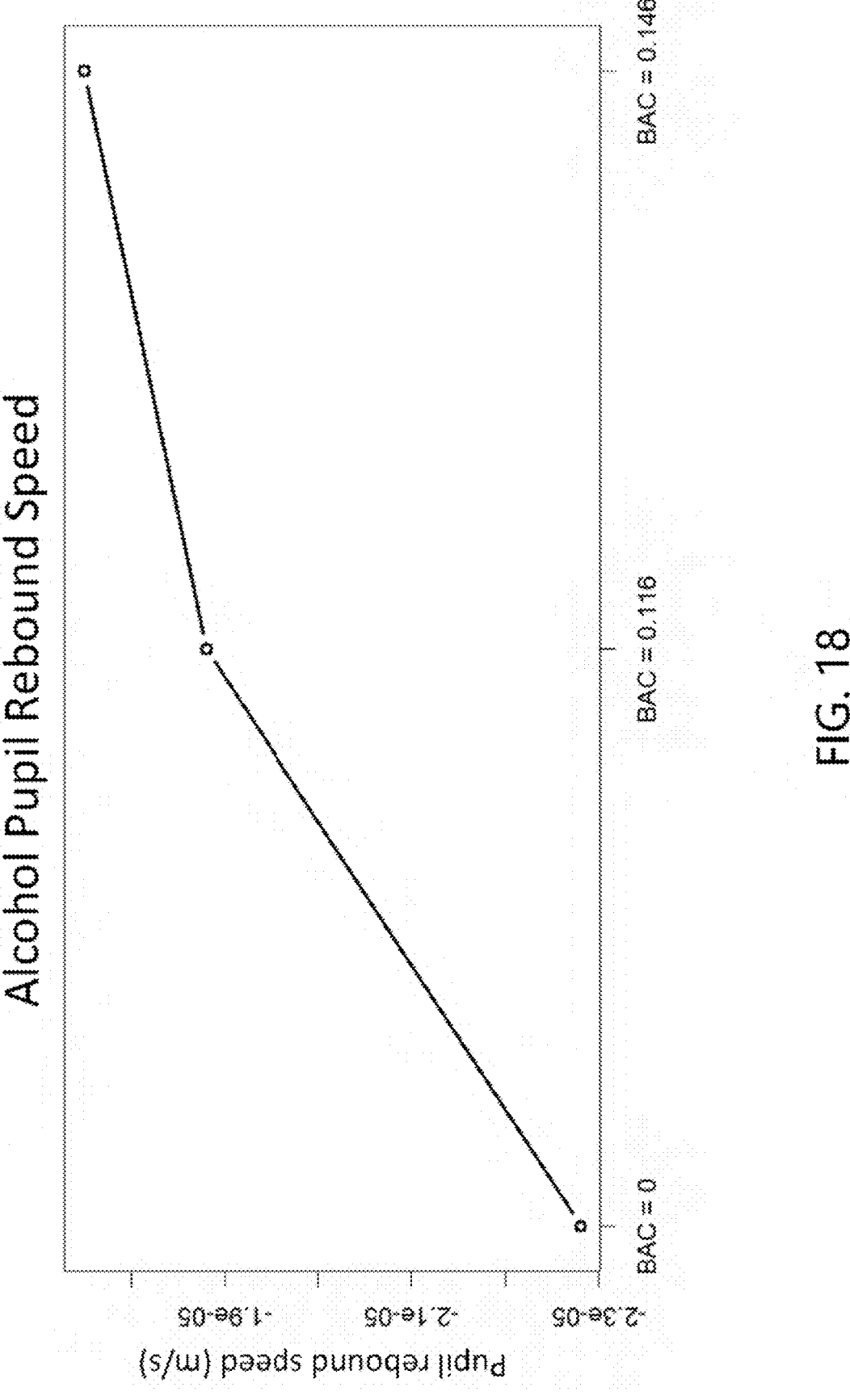

For purposes of concision, only the raw data for test subject B is provided as shown in the charts of FIGS. 13-16. The pupil rebound speed results for test subject B are shown in FIG. 17, and the results for test subject A are shown in FIG. 18.

The data obtained from the VR headset during the pupil rebound test is first analyzed by considering only the pupil size data obtained after the bright light is applied. With reference to FIG. 12, this is represented as the first time the brightness reaches level 20. Segmented regression is then used to determine the time at which each test subject's pupil size leveled off after application of the bright light. Segmented regression is an iterative process which uses an algorithm to find the break point between which a data set is well-approximated by a line.

The segmented regression process first involves calculating the slope of the line between the point when the bright light is applied and the point when the pupil size levels off is calculated. In other words, the pupil size at the first time the brightness reaches level 20 gives one point (time_1, size_1). The time at which the pupil size levels off and the corresponding pupil size at the leveling-off time gives a second point (time_2, size_2). These two points can be seen on the right side of the chart presented in FIG. 13. The slope of the line that connects the two points (time_1, size_1) and (time_2, size_2) represents the pupil rebound speed. Since this connecting line is decreasing, the slope of the connecting line is negative. As such, the absolute value of all slope values is used to find the largest.

The results of the pupil rebound test in the charts and plots of FIGS. 12-18 are representative of the type of information output as part of the impairment indication information 140 described above.

Pupil Rebound Test Results

Figure 14:
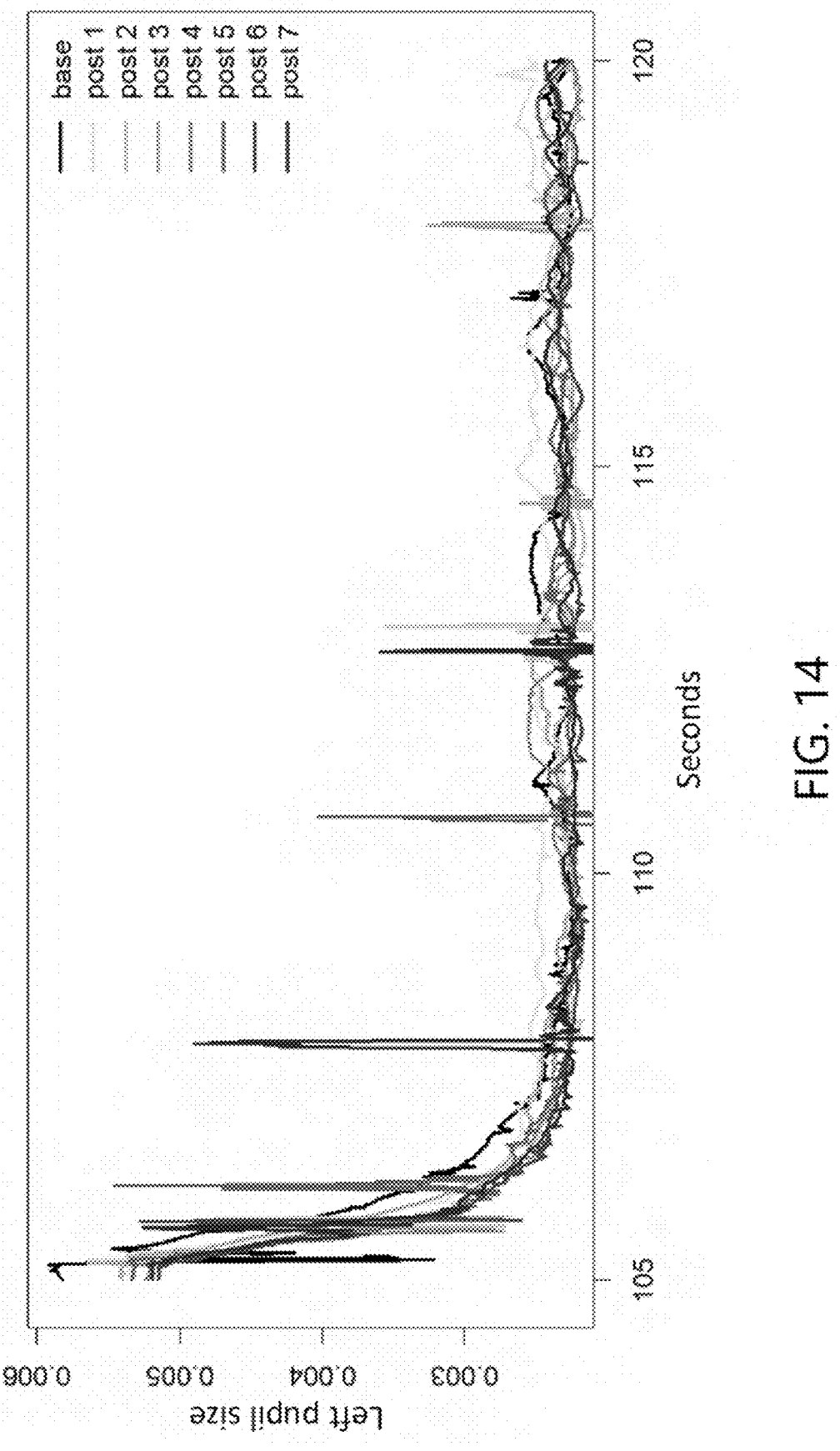

Referring to FIG. 14, a chart is presented which shows the raw data obtained after the bright light is applied to the left pupil of test subject B. In the chart of FIG. 15, the data from FIG. 14 has been smoothed using the Loess smoothing window at a length 0.05 seconds. In FIG. 16, segmented regression has been applied to the data to find the leveling off point described above. FIG. 17 then shows the cannabis pupil rebound speed results from test subject B. Based on the results shown in FIG. 17, no clear relationship is observed between pupil rebound speed and post-smoking time, but the pupil speed was slowest during the baseline and fastest at Post4.

FIG. 18 shows the alcohol pupil rebound speed results from test subject A. Based on FIG. 18, there is a clear relationship between pupil rebound speed and BAC level. This is because the baseline BAC of 0 has the fastest pupil rebound speed and highest BAC of 0.146 has the slowest rebound speed.

HGN45 Test

Figure 19:
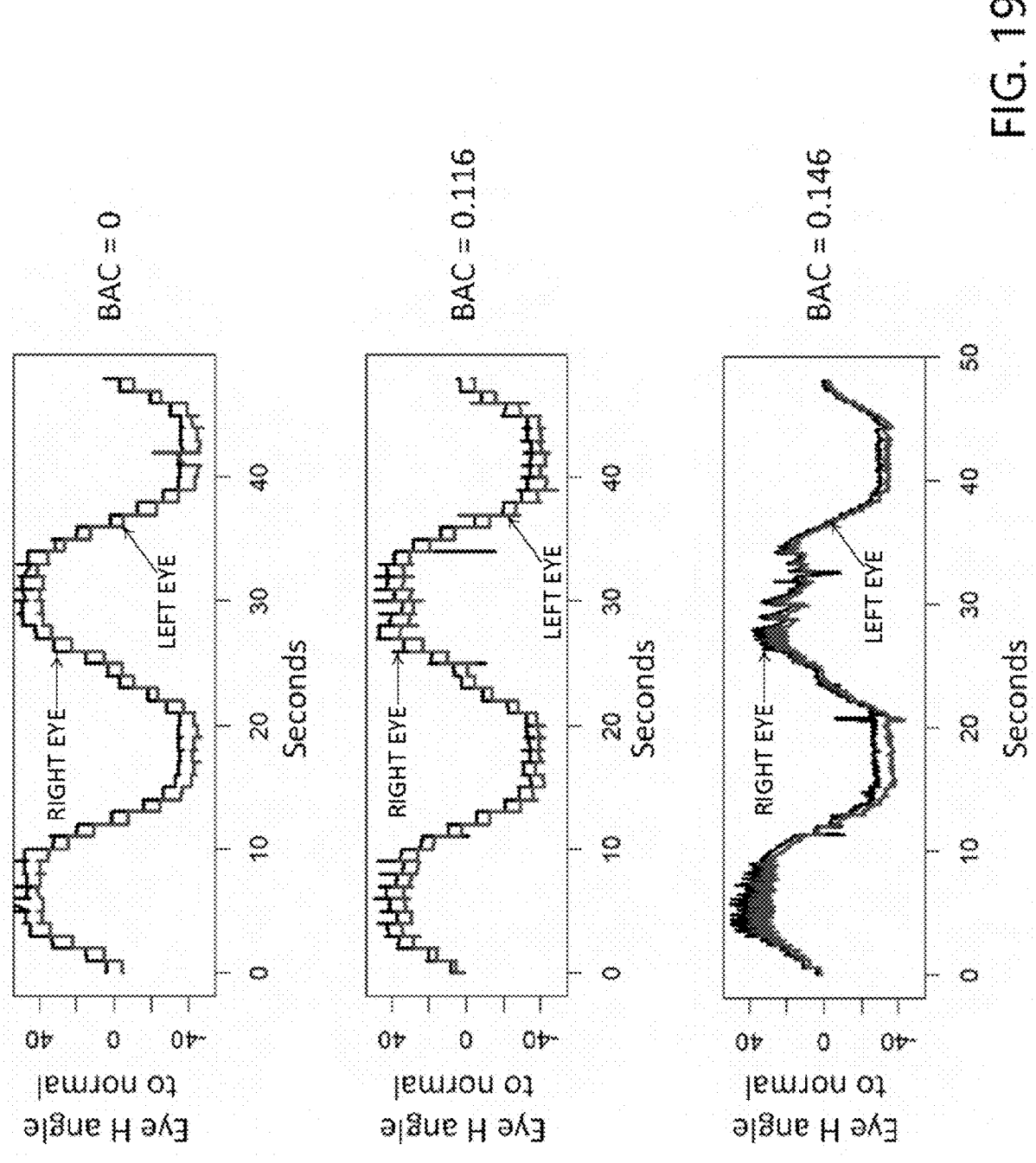
FIGS. 19-21B are illustrations of various charts and plots showing the data obtained from an HGN45 test configured to detect the onset of nystagmus prior to 45 degrees and the results thereof.
Figure 20:
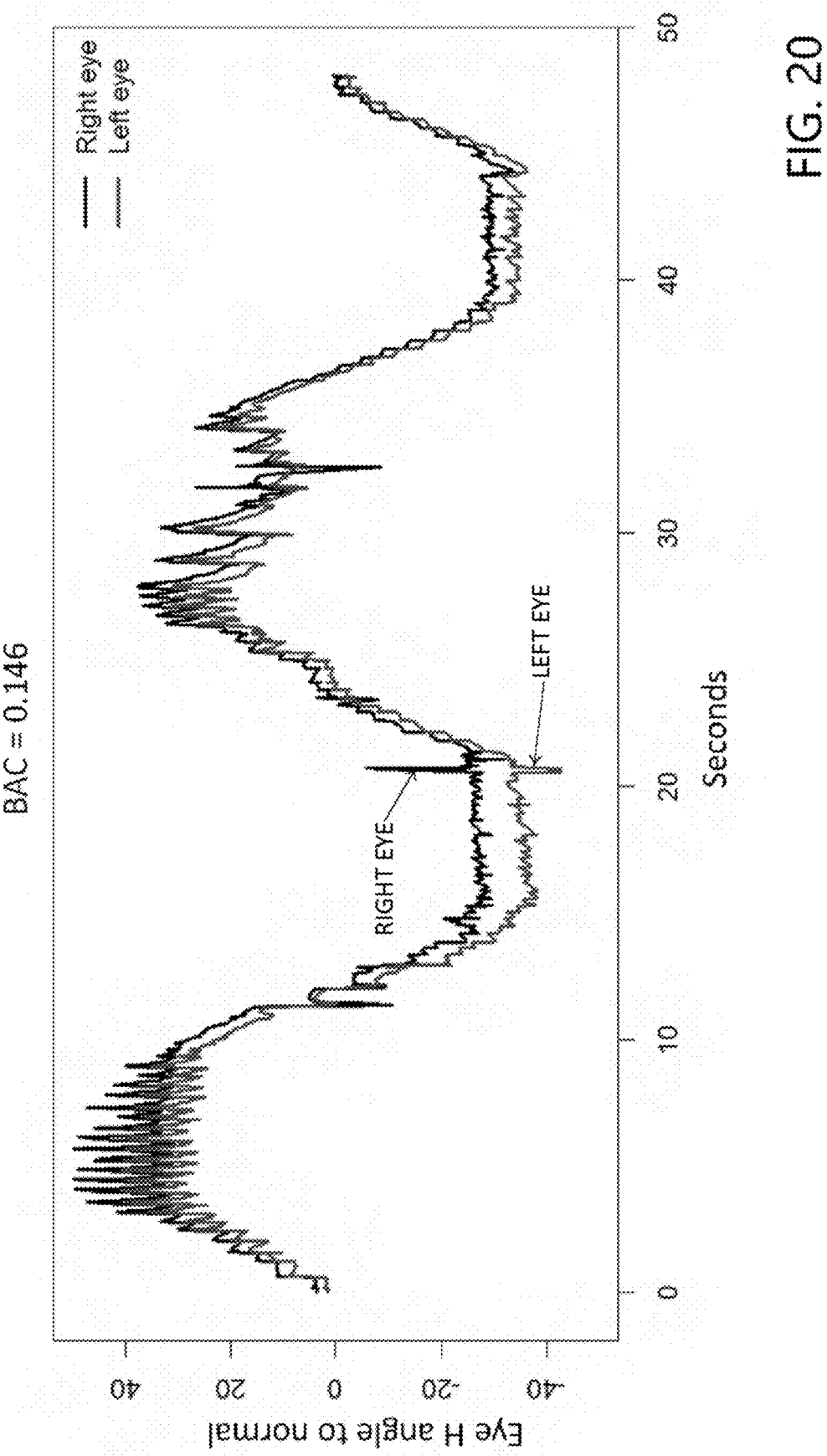
Figure 21A:
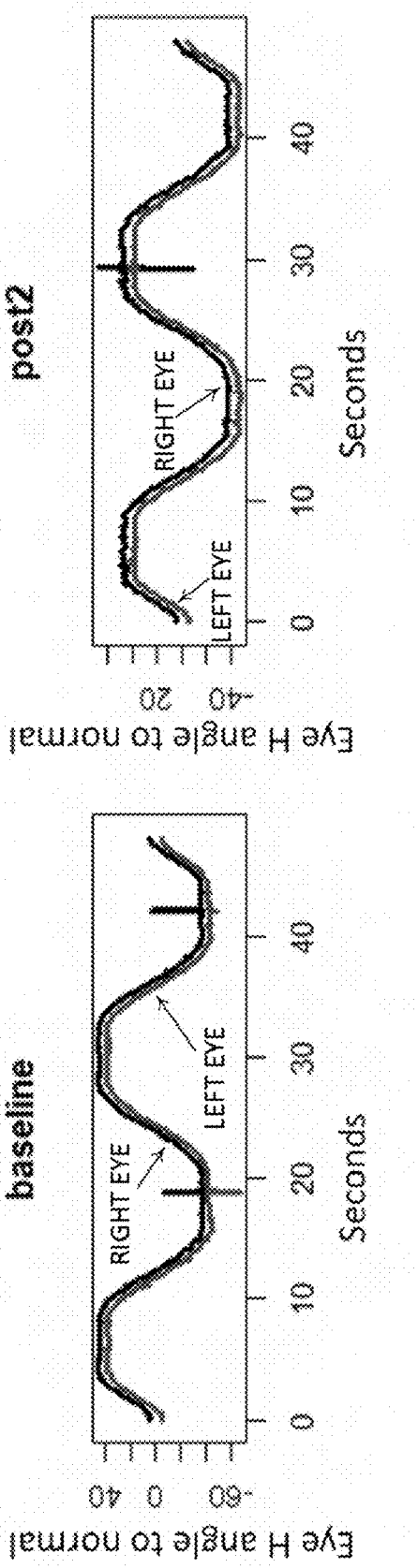
Figure 21B:
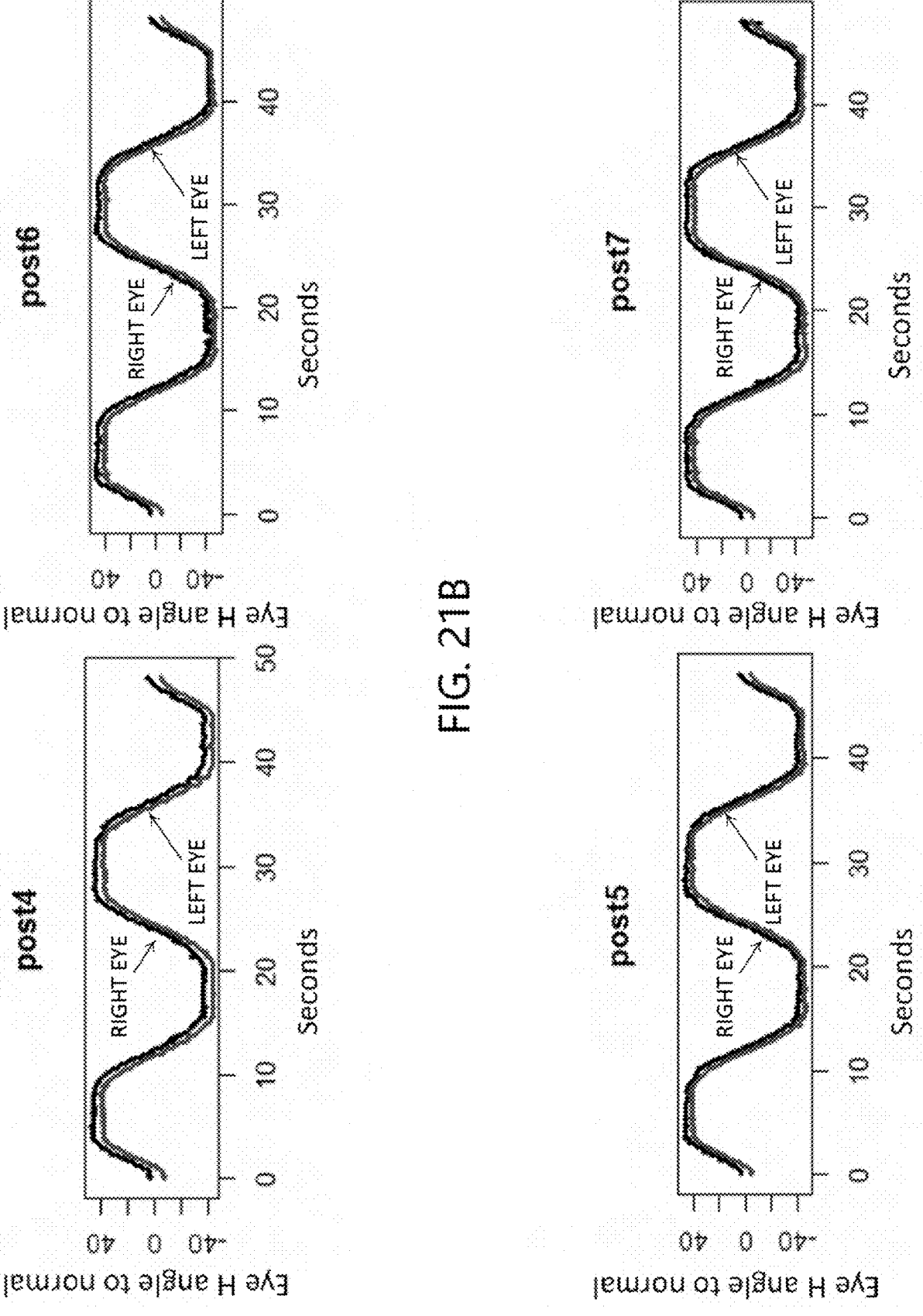

The HGN45 test, represented in FIGS. 19-21B, is similar to the HGN tracking test described above but is specifically configured to detect the onset of nystagmus prior to 45 degrees. The tracking results for test subject A are shown in FIGS. 19 and 20 and the tracking results for test subject B are shown in FIGS. 21A-21B. The results of the HGN45 test in the charts and plots of FIGS. 19-21B are representative of the type of information output as part of the impairment indication information 140 described above.

HGN45 Test Results

In FIGS. 19 and 20, nystagmus prior to 45 degrees is present in test subject A, especially with a BAC level of 0.146. That is, referring to FIG. 20, the group of spikes on the curve between 5 and 10 seconds is representative of high nystagmus indicative of impairment.

In FIGS. 21A and 21B, no nystagmus was indicated for test subject B at any of the post-smoking times.

LOC Test

The LOC test, represented by FIGS. 22A-28B, involved the VR headset moving the tracked object towards the bridge of each test subject's nose and assessing the test subject's ability to cross their eyes and maintain focus on the tracked object. In this regard, the ability to cross eyes indicates non-impairment whereas the inability to cross eyes (i.e., inability of the test subject's eyes to converge, or LOC) is indicative of impairment. LOC was determined from the LOC test data obtained for each test subject by using the right and left eye horizontal (H) angle to normal variable defined above.

Figure 22A:
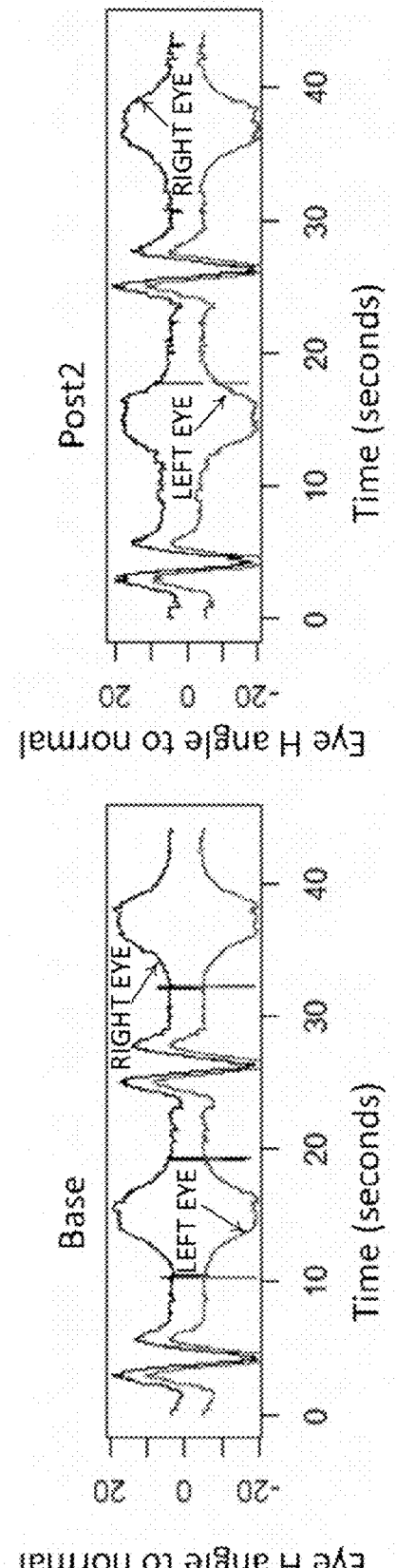
FIGS. 22A-28B are illustrations of various charts and plots showing the data obtained from an LOC test and the results thereof.
Figure 22A:
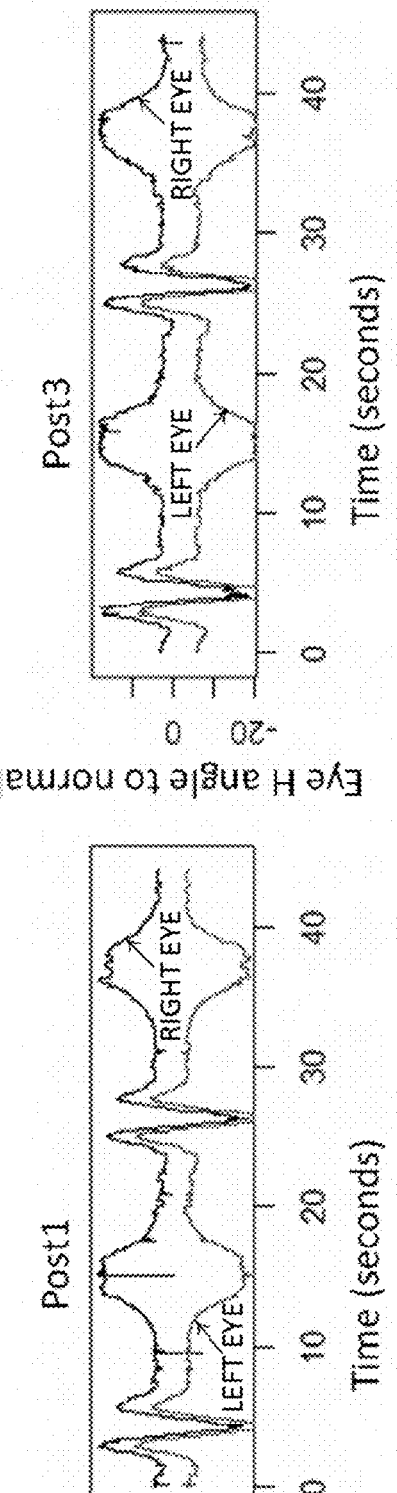
Figure 22B:
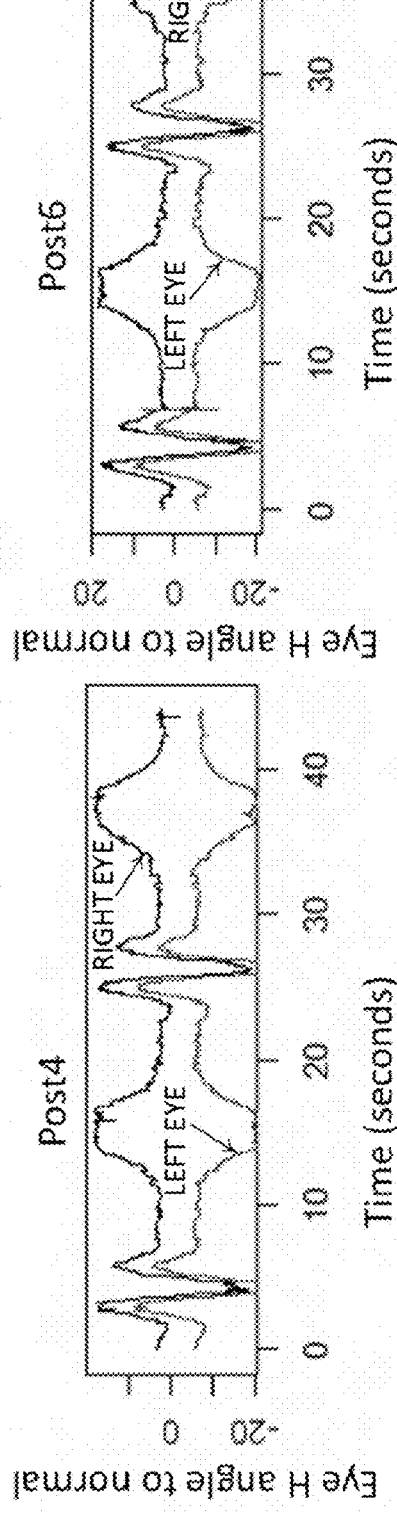
Figure 22B:
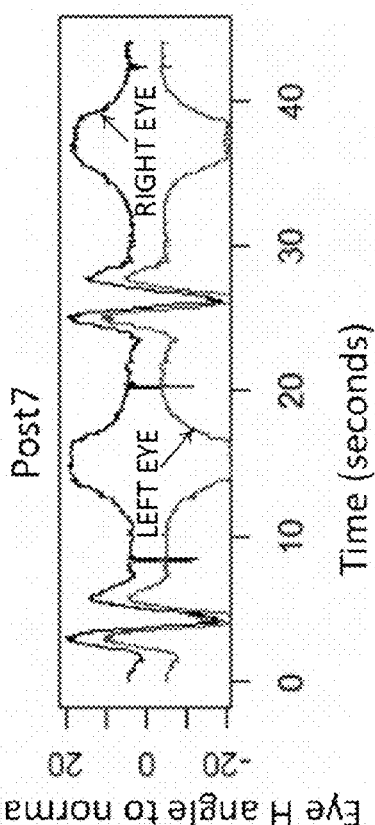
Figure 22B:
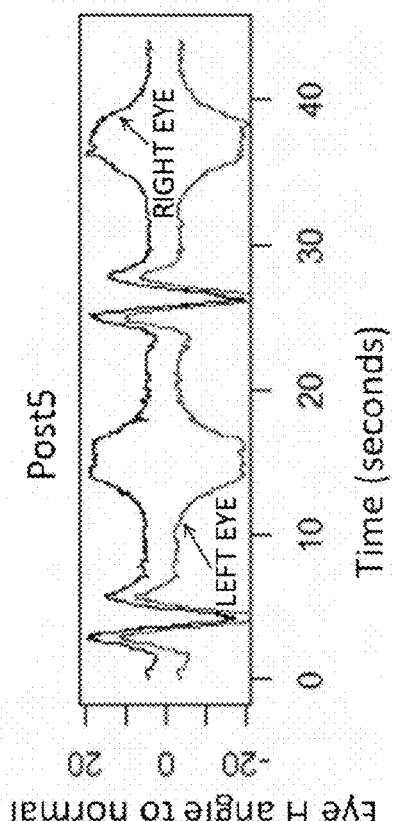
Figure 23:
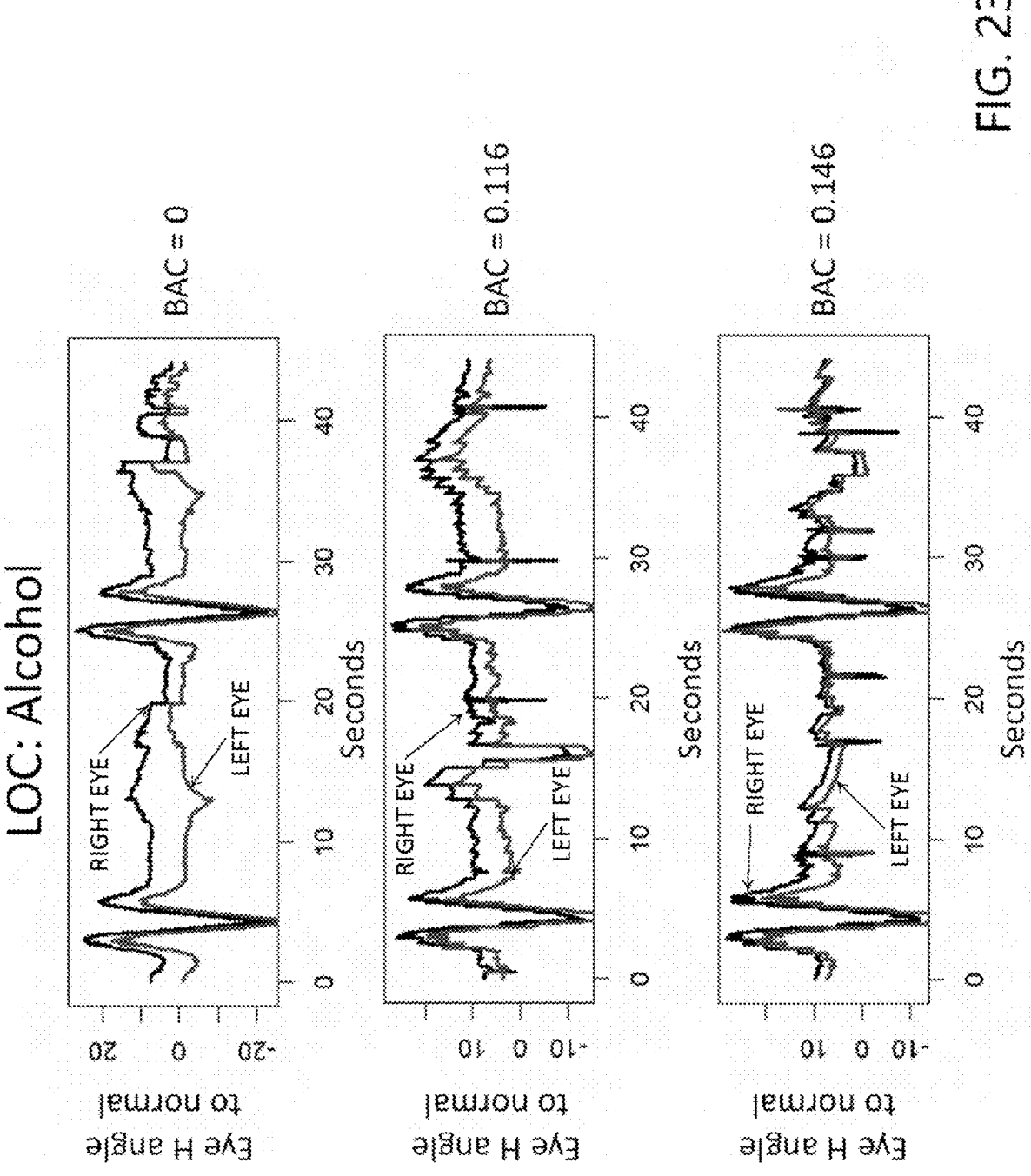

Thus, the goal of the LOC test is to quantify each test subject's ability or inability to cross their eyes when following the object displayed by the VR headset 102. The angles of the test subjects' eyes, as shown by the Y-axes of the charts in FIGS. 22A-23, are measured directly by the sensor of the VR headset. A large difference between the left eye and right eye H angle to normal represents crossed eyes indicative of non-impairment and a small or no difference represents non-crossed eyes indicative of impairment. FIGS. 22A-22B show the results of test subject B and FIG. 23 shows the results of test subject A.

In order to implement the LOC test on the VR headset 102, an algorithm was developed in two primary stages to quantify LOC considering the location of the tracked object. The first stage of algorithm development for the LOC test was to normalize the raw LOC test data curves by taking the absolute values of the differences between the right and left eye H angles. The second stage was to find windows for when the target object was close to and far from the test subject's eyes. The steps of each algorithm development stage are described in further detail below and are at least partially represented by the charts and plots illustrated in FIGS. 24-28B.

It is noted that FIGS. 24-27B specifically use the data obtained from test subject B to illustrate the methodology behind the algorithm development, but the same methodology would be applied to the data obtained from test subject A. Thus, the methodology as applied to test subject A's data is omitted from the figures for purposes of concision, but the LOC test results are provided for subject A in the plots of FIGS. 28A and 28B.

As mentioned above, the first stage of algorithm development involved normalizing the raw LOC test data curves. Step 1 of the first stage of the algorithm development was to remove irregularities in the data due to blinking of the test subject's eyes. In order to characterize the blinks, the variables for the eye H angles were set to a value of 999.

Step 2 of the algorithm development's first stage was implemented to correct errors potentially introduced by the blink removal procedure of step 1. These errors may arise because the blink removal procedure results in the elimination of some of the raw LOC test data. To correct for such errors in step 2, R programming was used to approximate the right and left eye curves so that values could be taken at identical time points. In particular, the R function "approx" was used to approximate the curves.

Figure 24:
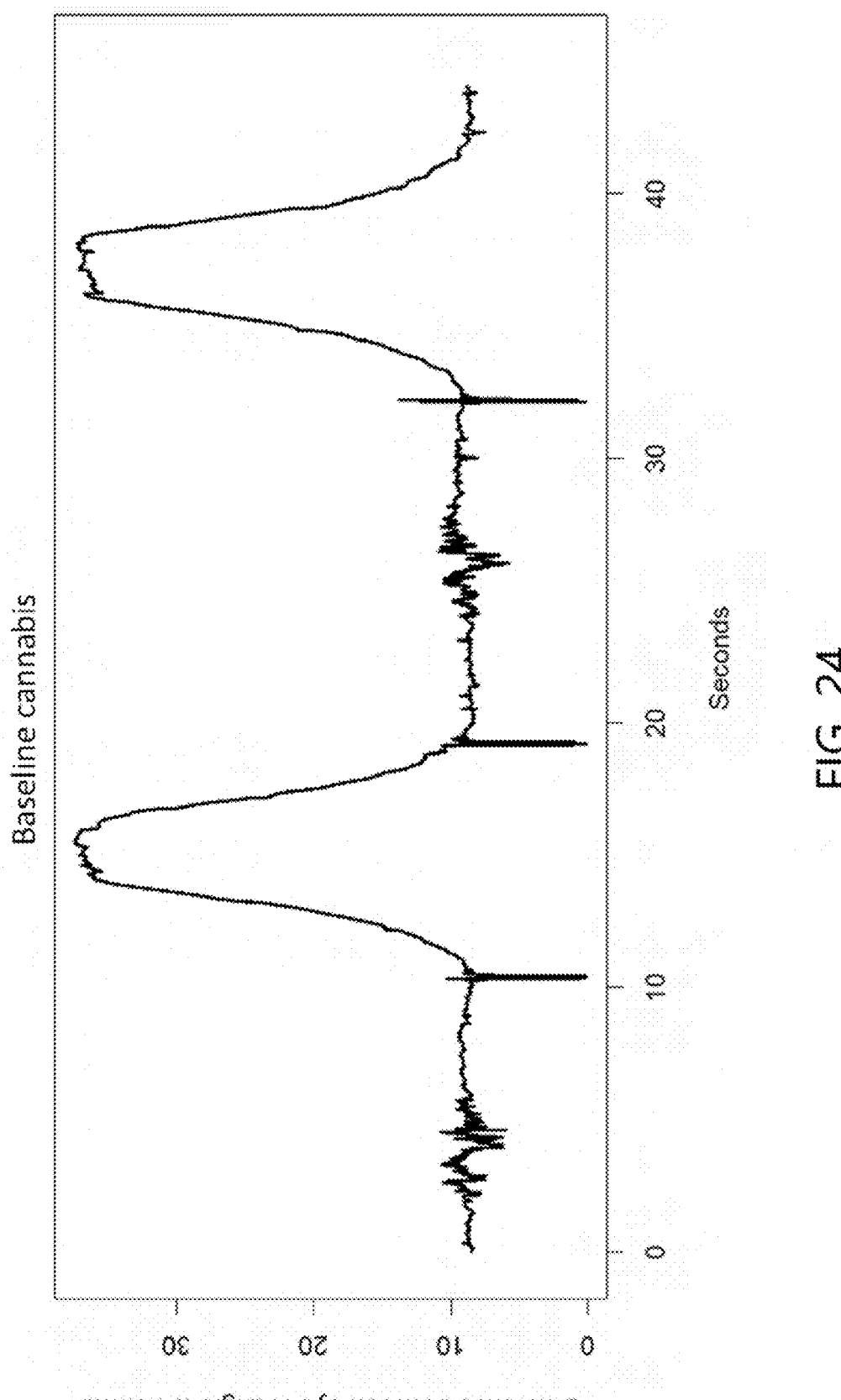

After completion of steps 1 and 2, the differences between right and left eye H angles to normal were determined in step 3 by subtracting the left eye H angles to normal from the right eye H angles to normal at each second interval shown on the X-axes of FIGS. 22A-22B and 23. As illustrated in the chart of FIG. 24, the absolute value of the differences could then be determined to make all values positive. It is noted that FIG. 24 only illustrates the curve of absolute values resulting from the baseline cannabis dataset of FIG. 22A. However, absolute value curves were also generated for each dataset obtained from both test subject A and B.

As briefly discussed above, the second stage of algorithm development was to find windows for when the target object was close to and far from the test subject's eyes. With reference to the right-side Y-axis of FIG. 25, the values for the tracked object Z position were used to find the position of the target. The tracked object Z position is also illustrated in FIG. 25 by the red curve which overlays the absolute value of differences curve taken from FIG. 24.

Figure 25:
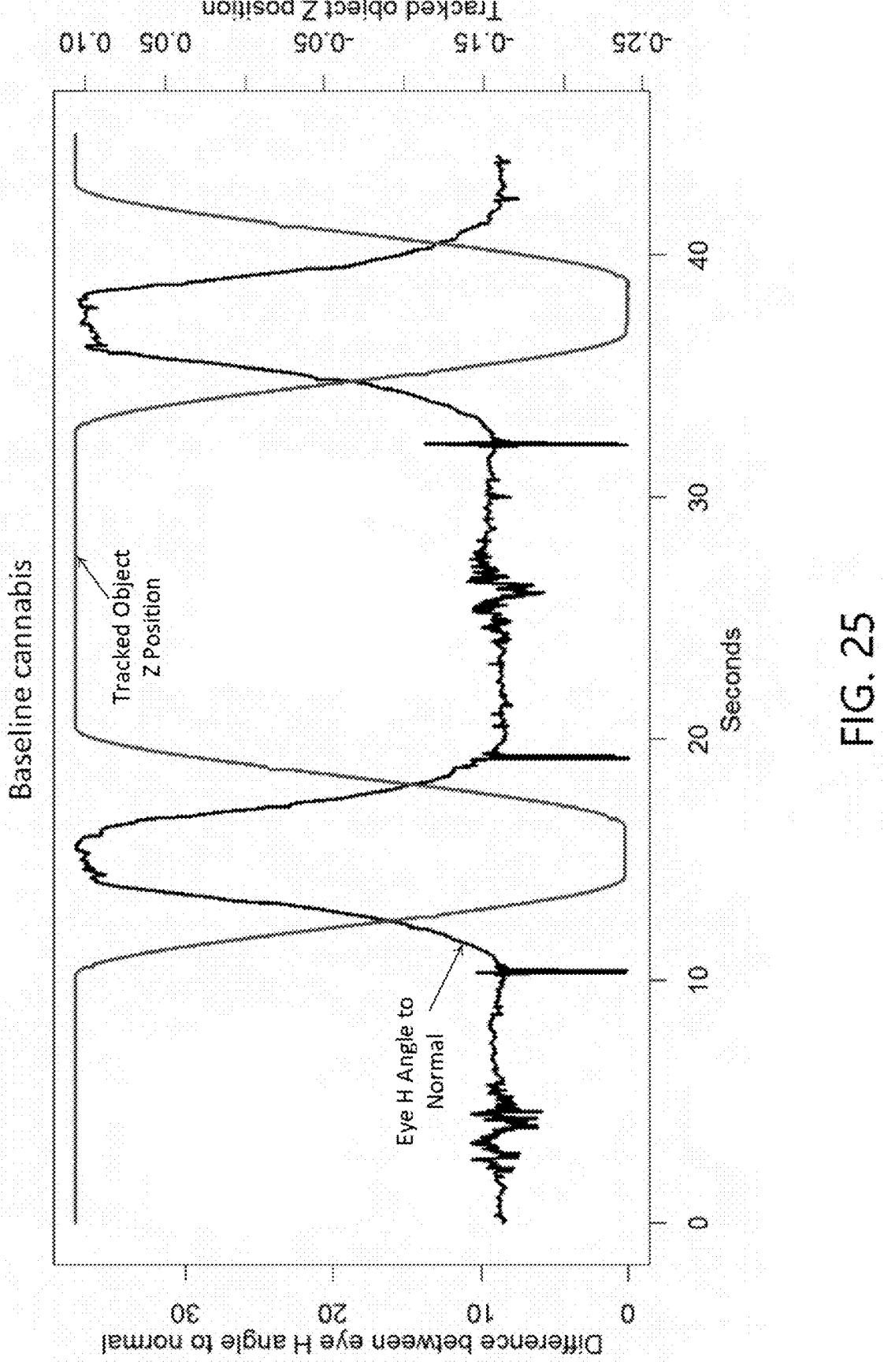
Figure 26:
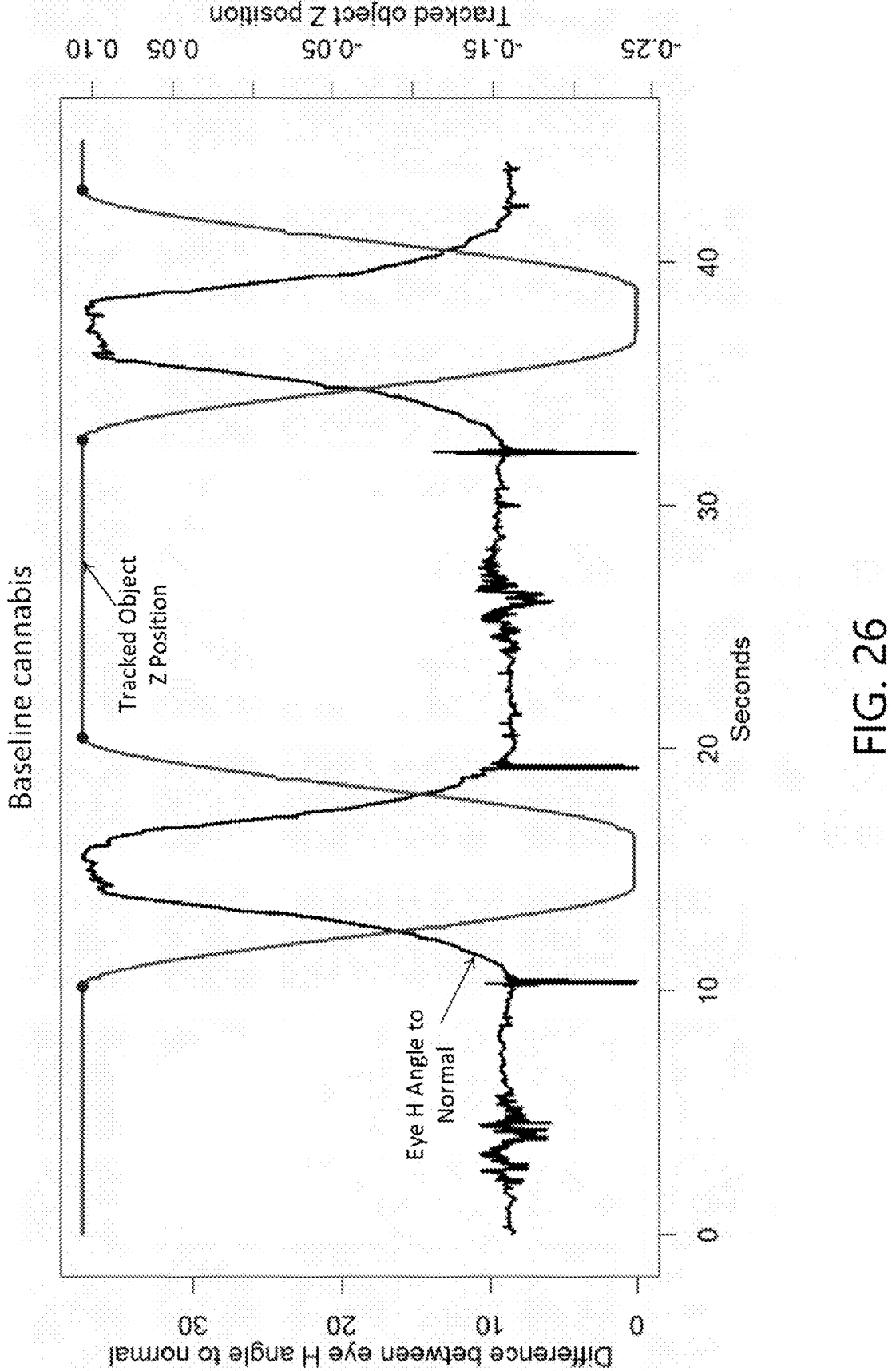

Looking at the overlaying curves illustrated in FIG. 25, it is evident that when the object is far from the test subject's eyes (i.e., higher Z position values), the difference between eye H angle to normal is smaller compared to when the object is close to the test subject's eyes (i.e., smaller Z position values). Furthermore, when the object was far from the test subject's eyes, the Z position values were the same. However, this is not the case when the object was close to the test subject's eyes.

Based on the chart of overlaying curves illustrated in FIG. 25, the second algorithm development stage was implemented to find windows for when the target was close to and far from the test subject's eyes. In step 1 of the second stage, a True/False vector was constructed for Z position values that were the same as the previous three values. Then, positions were marked where the vector changed between True and False or False and True to represent when the object moved close to or far from the test subject's eyes. The blue dots in FIG. 26 indicate when these changes occurred.

Figure 27A:
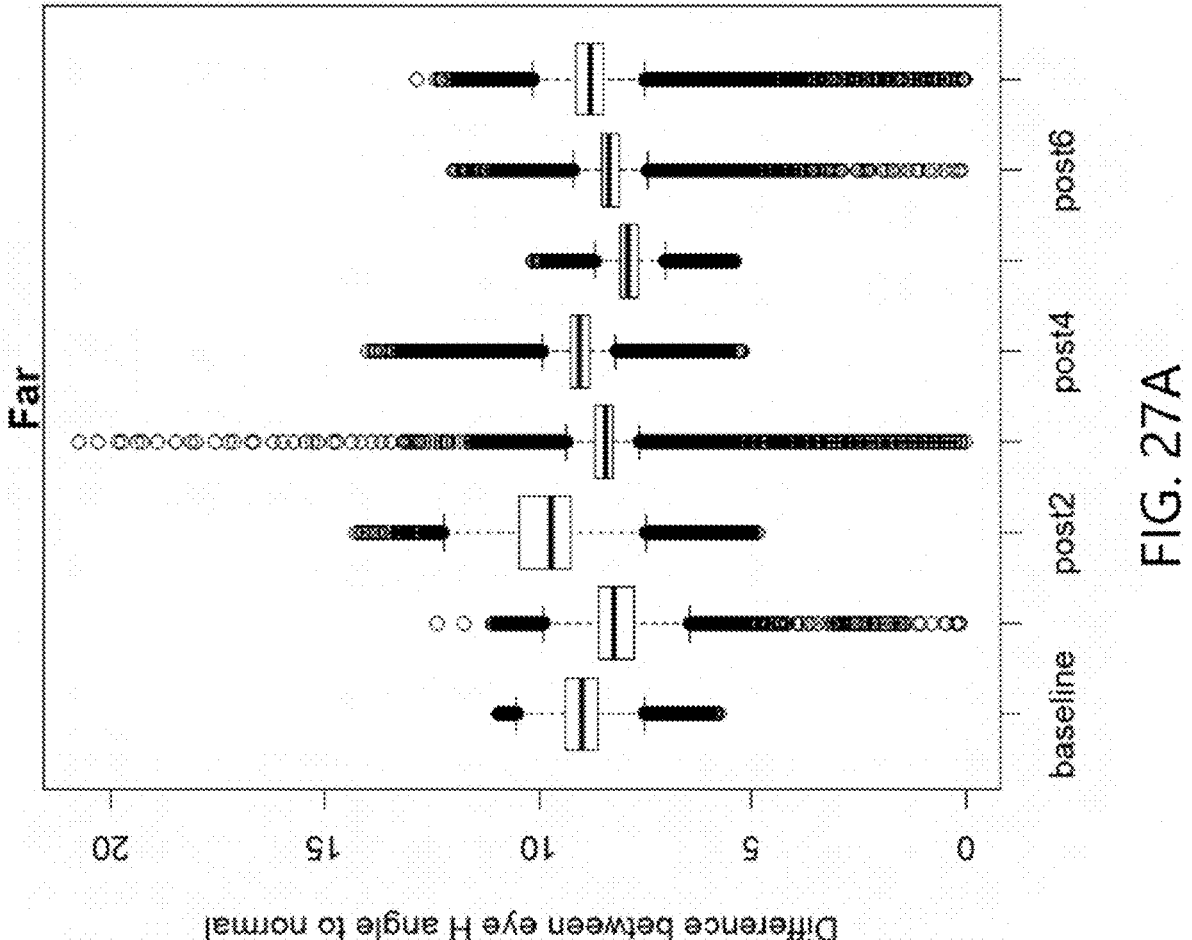
Figure 27B:
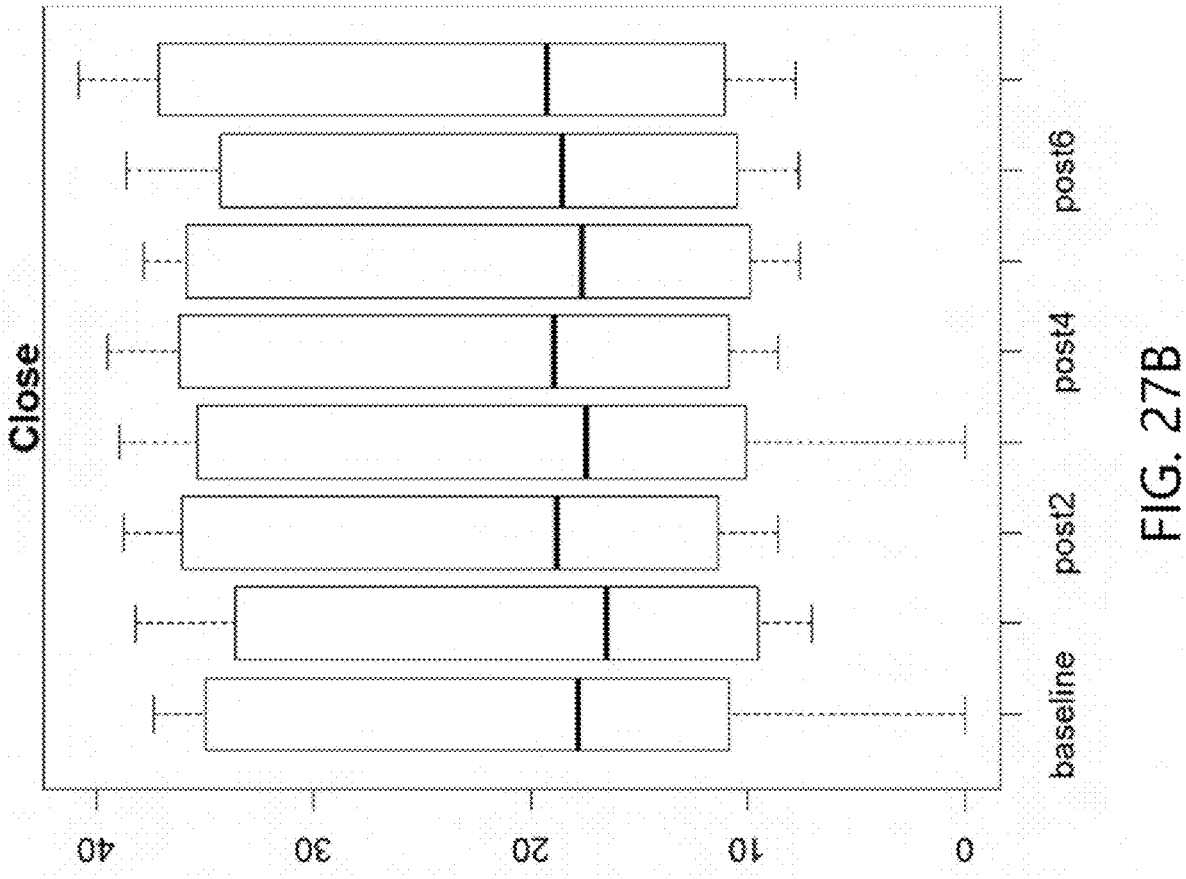
Figure 28A:
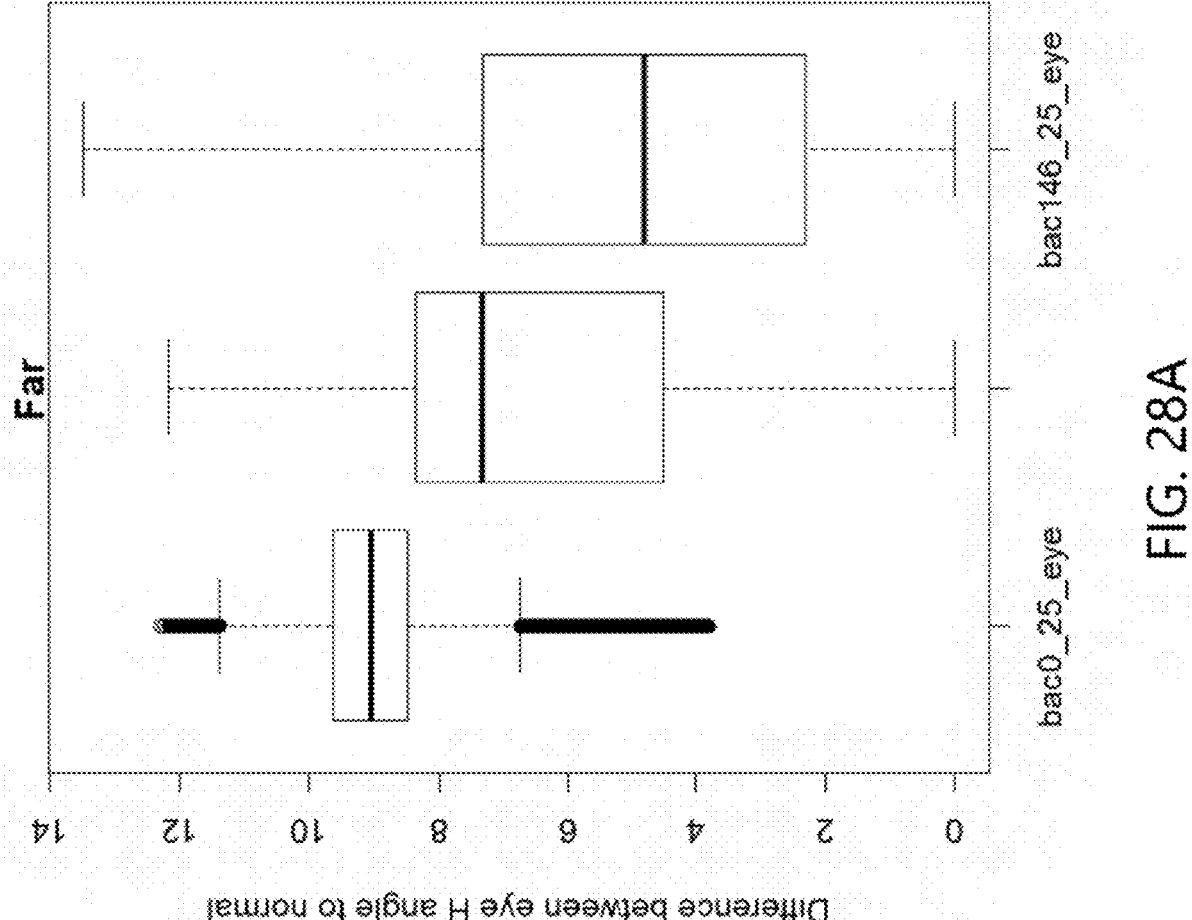
Figure 28B:
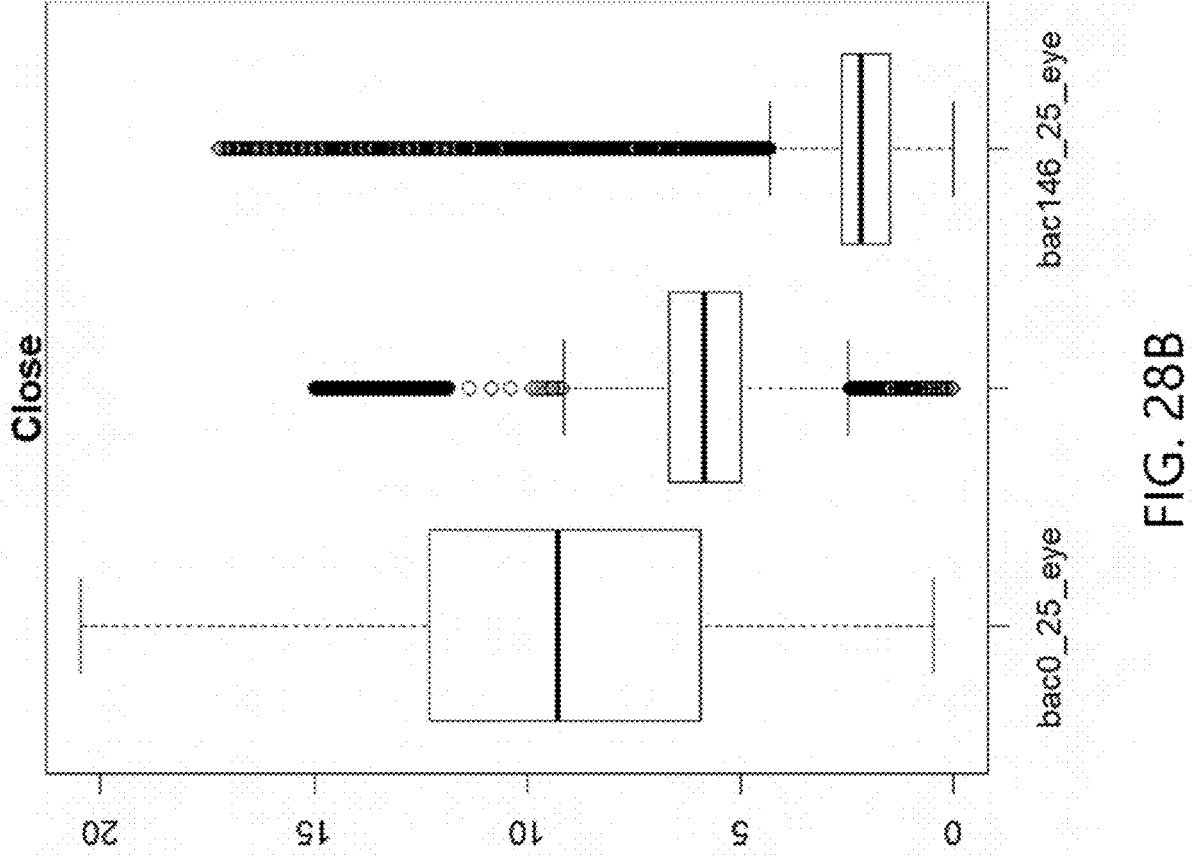

In step 2 of the second stage, the differences between the eye H angles to normal and the vector change positions (i.e., the blue dots in FIG. 26) was found for all occurrences. Distributions for the differences in eye H angles to normal for when the target was both far from and close to the test subject's eyes were then analyzed to draw conclusions from the LOC test data obtained from test subjects A and B. The distribution results for test subject B are illustrated in the boxplots of FIGS. 27A-27B and the distribution results for test subject A are illustrated in the boxplots of FIGS. 28A and 28B.

The results of the LOC test shown in the charts and plots of FIGS. 22A-28B are representative of the type of information output as part of the impairment indication information 140 described above.

LOC Test Results

Referring to FIGS. 23A and 23B, it appears that test subject B did not have much difficulty crossing eyes at any of the post-smoking times. In contrast, with reference to FIG. 24, it appears that test subject A's ability to cross eyes decreased with an increase in BAC. It is noted that test subject A may have had difficulty crossing eyes regardless of impairment based on the results at the baseline BAC of 0.

With reference to the boxplots of FIGS. 27A and 27B for test subject B, the distributions for the differences between eye H angles to normal appeared to be similar within the respective "far from" and "close to" groups. The largest differences occurred in Post3 of FIGS. 27A and 27B, which likely indicates that test subject B exhibited the highest level of cannabis impairment at Post3. With reference to the boxplots of FIGS. 28A and 28B for test subject A, it can be seen that in both the "far from" and "close to" groups, the median differences between eye H angles to normal decreased as the BAC of test subject A increased.

Modified Romberg Test

Figure 29:
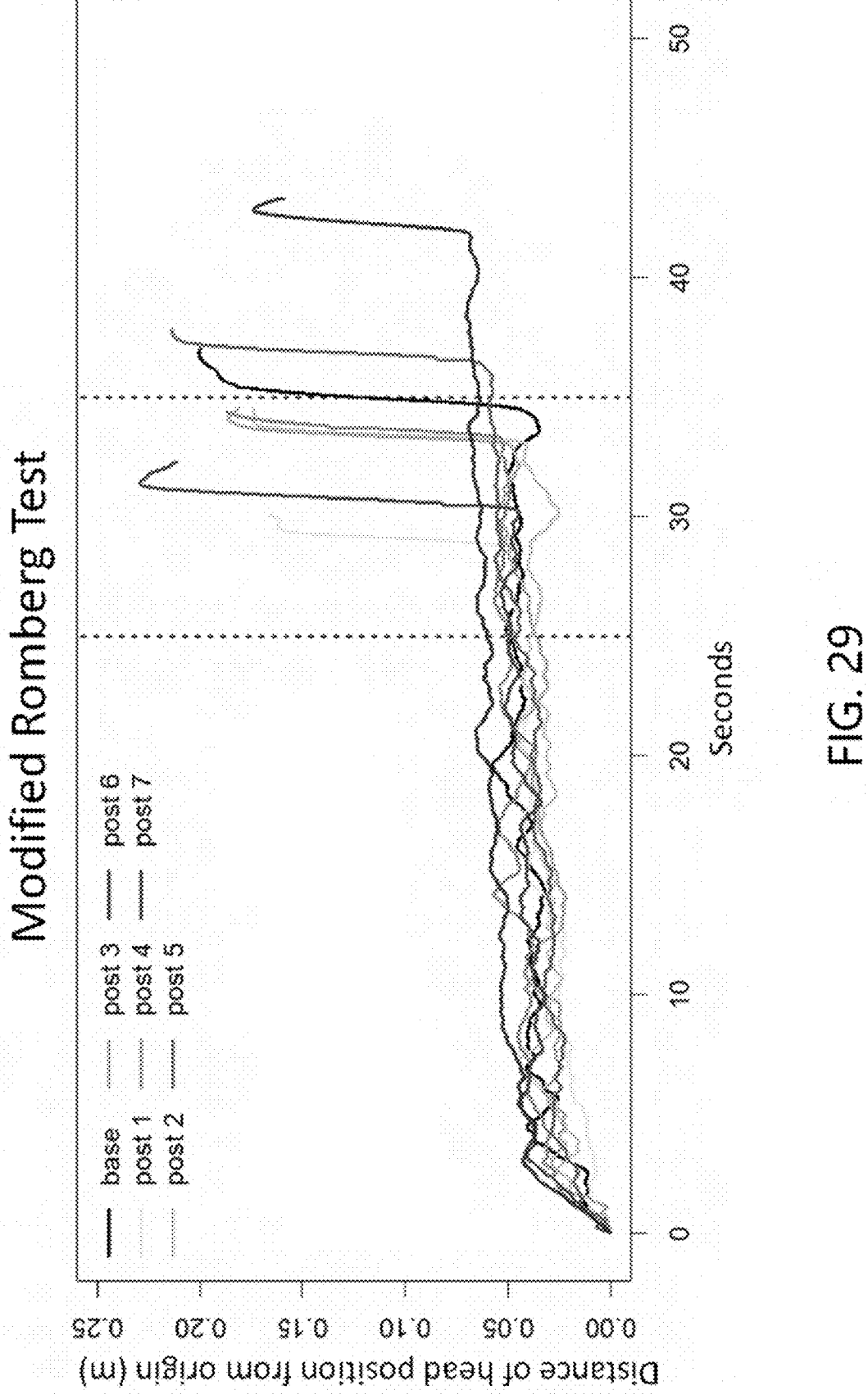
FIG. 29 is a chart showing the data obtained from a Modified Romberg test and the results thereof.

The results of the Modified Romberg test for test subject B are illustrated in FIG. 29. The Modified Romberg test is administered by having the test subject stand straight up with his or her head bent back and eyes closed. The test subject is then asked to estimate once 30 seconds has elapsed.

It is noted that, for purposes of the impairment testing examples disclosed herein, the Modified Romberg test was only administered to test subject A. However, the Modified Romberg test could be administered to test subject B if desired. The methodology for implementing and administering the Modified Romberg test with the VR headset for test subject B would be identical to the methodology described below for test subject A.

In order to implement the Modified Romberg test using the VR headset, an algorithm was developed to determine the amount of deviation from initial head position over time.

The amount of time at which the subject estimates 30 seconds have passed is also measured. This data is obtained and analyzed to find large deviations from origin which would indicate impairment.

Variables referred to as CameraPositionVectorX, CameraPositionVectorY, and CameraPositionVectorZ were used in the algorithm for the head position coordinates. A variable referred to as EyeOpenState was also used for the start time.

The analysis of the data obtained from the Modified Romberg test begins by finding the test start time (i.e., the first time the EyeOpenState variable has a value of 4 for eyes closed). Next, the test start time is normalized to zero. All coordinates of head position are also normalized so that when the test starts the origin is (x,y,z)=(0,0,0). Then, starting from the origin, the distance of each test subject's head position is calculated over time using the distance equation:

$$d = \sqrt{(x_1 - x_2)^2 + (y_1 - y_2)^2 + (z_1 - z_2)^2}$$

The blue dotted lines in the plot of FIG. 29 indicate an acceptable range of +/−5 seconds from the 30 second mark.

The results of the Modified Romberg test in the plot of FIG. 29 is representative of the type of information output as part of the impairment indication information 140 described above.

Modified Romberg Test Results

Referring to FIG. 29, there does not appear to be a significant difference between the distance of test subject B's head position from the origin after smoking compared to before smoking. Also, test subject B was able to accurately estimate the elapse of 30 seconds since most of the post-smoking curves end between the blue dotted lines.

Pupil Size During HGN Test

Turning now to FIGS. 30-48, the results of the pupil size during HGN test are shown. The pupil size during HGN test was developed in view of the HGN tracking test results discussed above. That is, the data necessary for the pupil size during HGN test was obtained using the left pupil size (although the right pupil size could also be used) data from the HGN tracking test data files described above. The data obtained for the pupil size during HGN test is provided in the chart of FIG. 30.

Figure 30:
FIGS. 30-48 are illustrations of various charts and plots showing the data obtained from a pupil size during HGN test and the results thereof.
Figure 31:
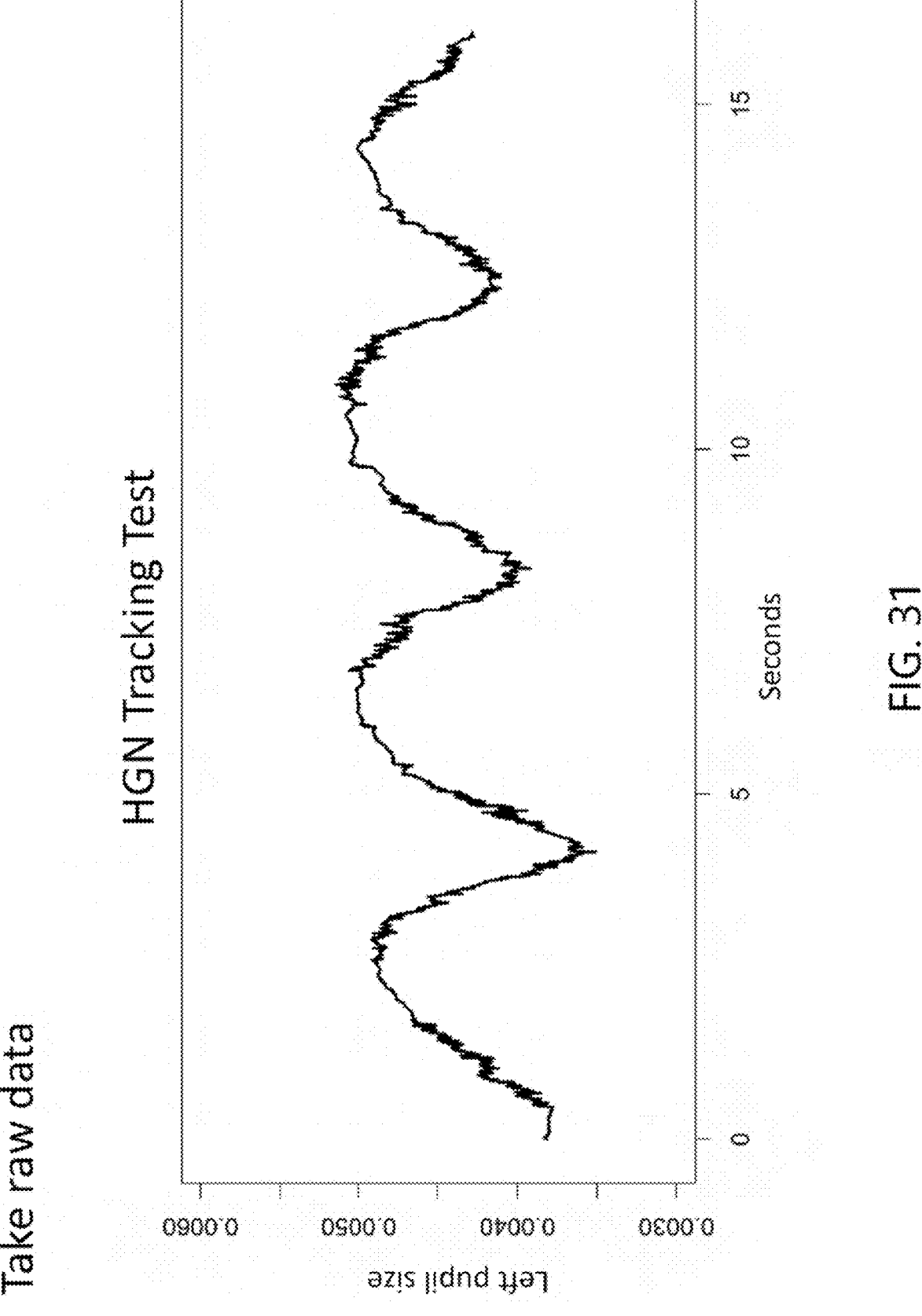

Upon analysis of the charted data in FIG. 30, it was observed at Post1 that the peaks and valleys of pupil size over time had a much smaller ratio when compared to the baseline. As such, it was desirable to determine whether this peak-to-valley ratio could be indicative of impairment. In order to implement the pupil size during HGN test on the VR headset, an algorithm was developed to detect the peaks and valleys. The peaks represent local maximums and the valleys represent local minimums of the curve. The term "local" is used here to mean that these maximums and minimums only pertain to a specific window of time. The algorithm development steps included first smoothing the raw HGN tracking test data for Post1 shown in FIG. 31 using the Loess smoothing window with a size of 0.05 seconds. The smoothed data, which is shown in FIG. 32, is important for eliminating the many local maximums and minimums which would otherwise be present within a window.

Figure 32:
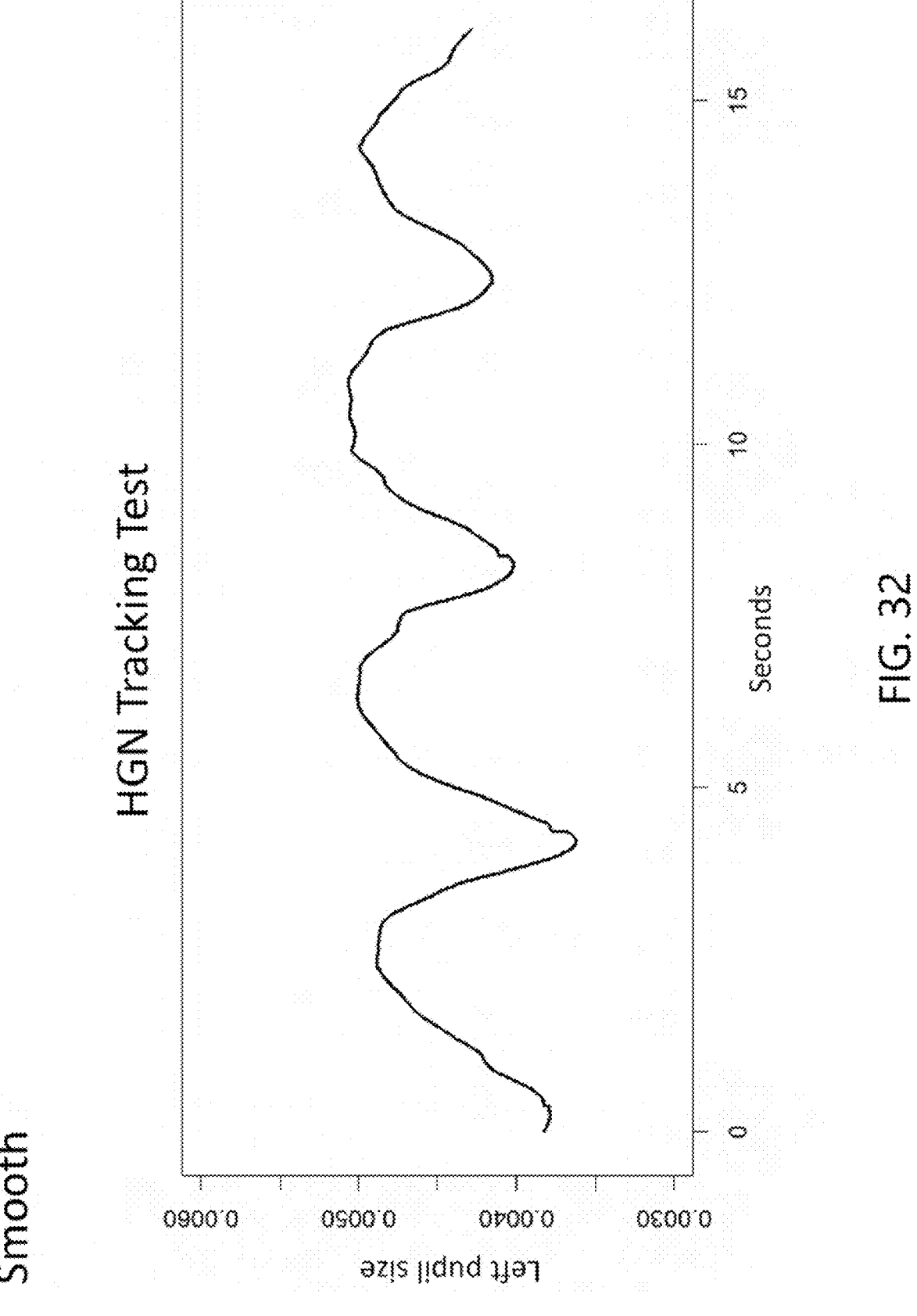
Figure 33:
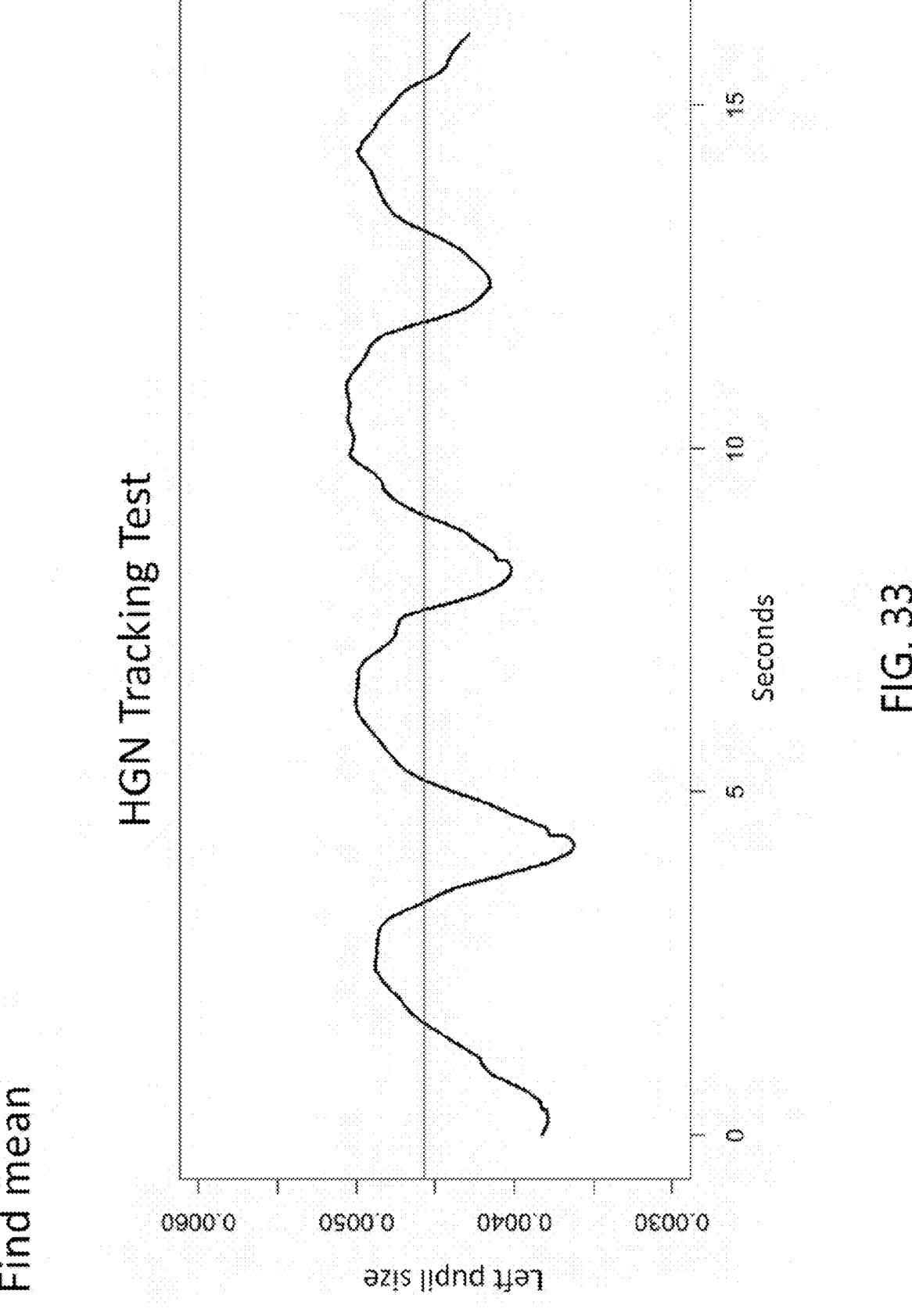
Figure 34:
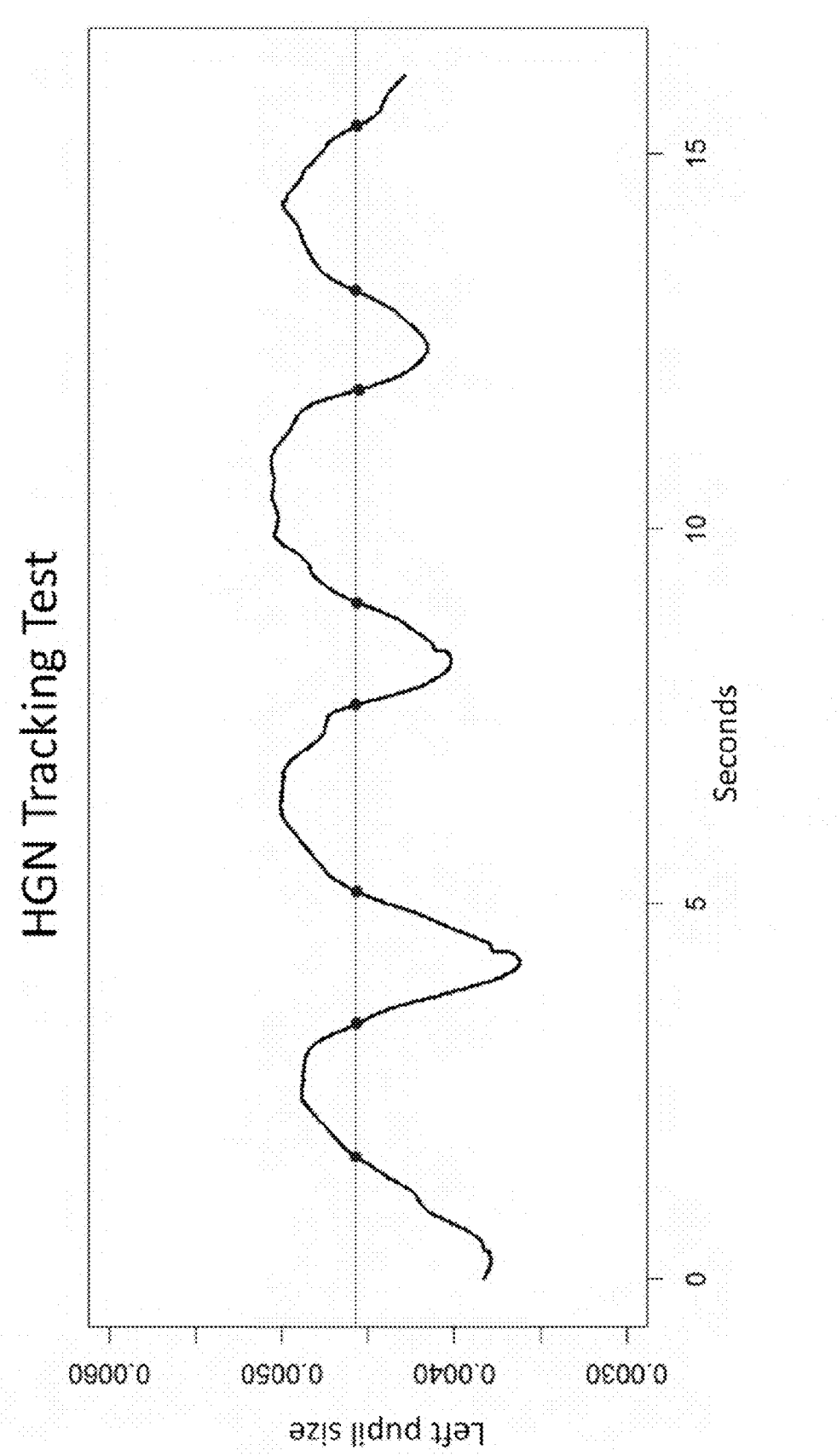
Figure 35:
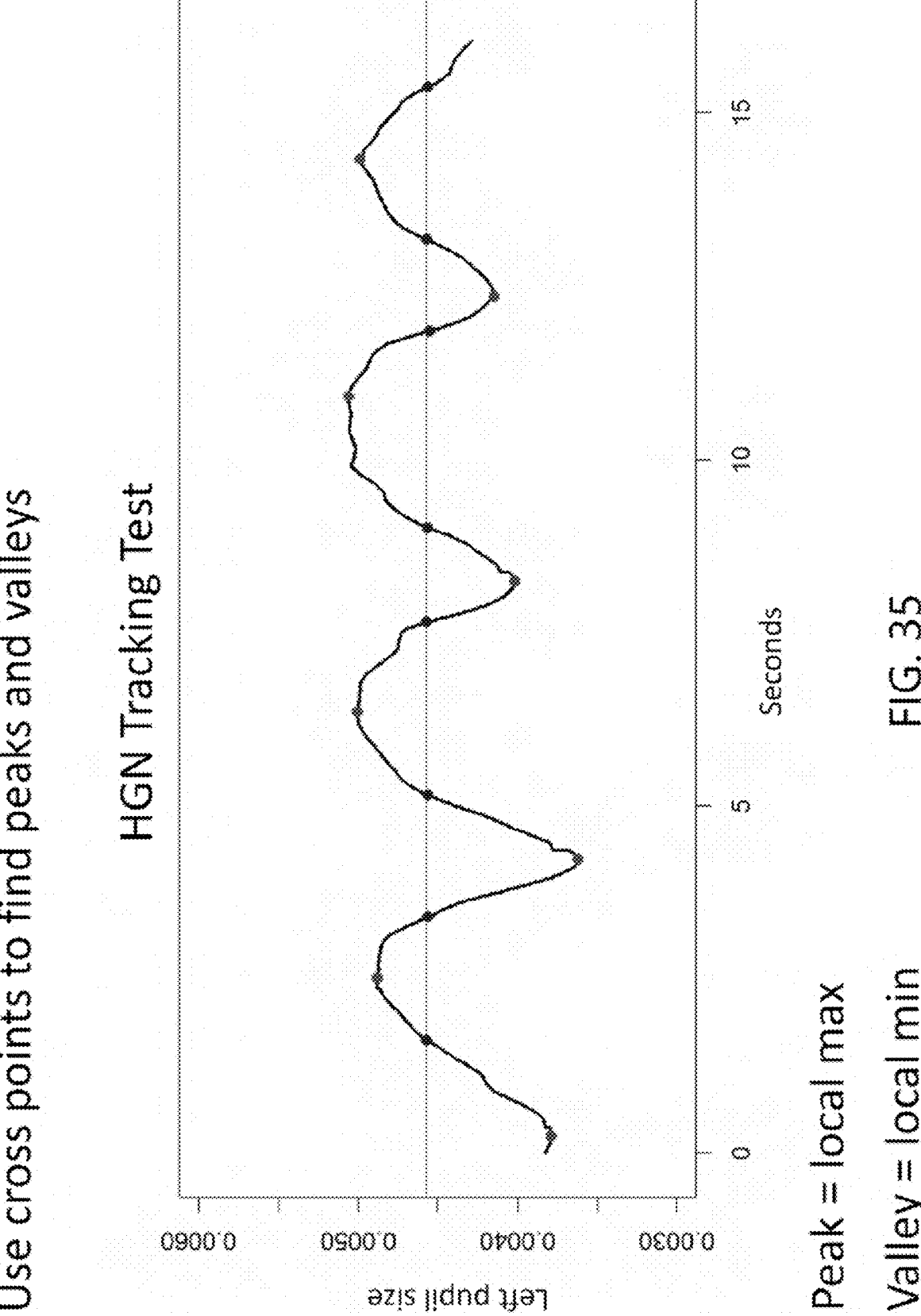

The second algorithm development step was to find the mean of the smoothed curve in FIG. 32. The red line illustrated in FIG. 33 represents the mean of the smoothed curve.

Figure 36A:
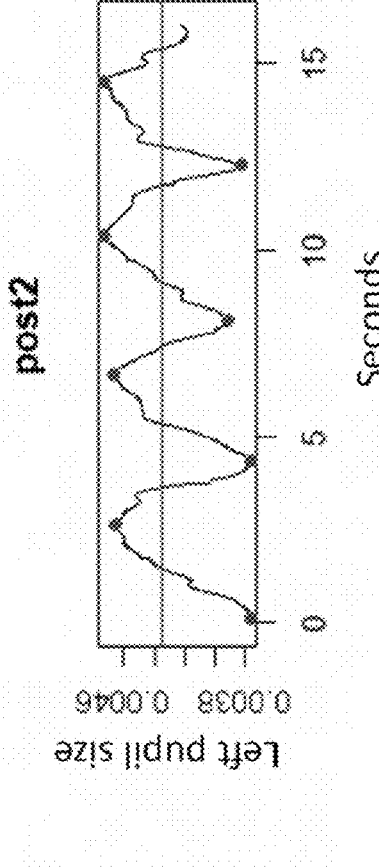
Figure 36A:
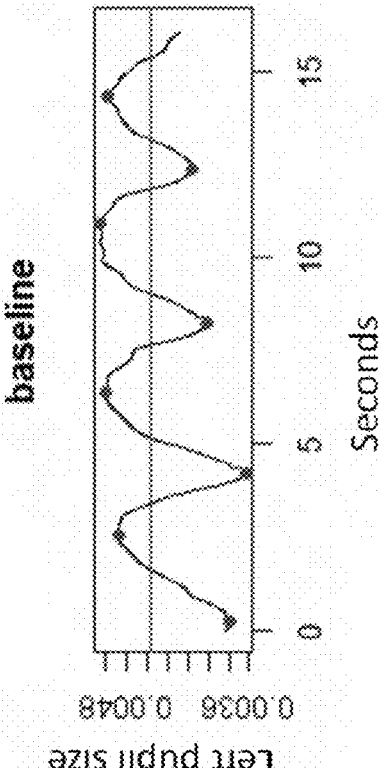
Figure 36A:
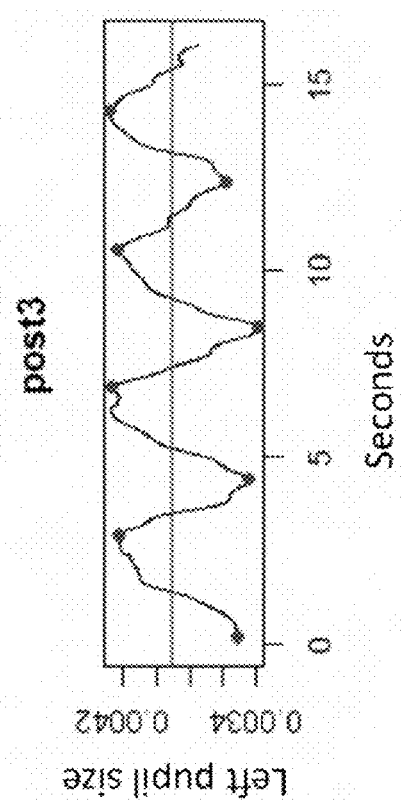
Figure 36A:
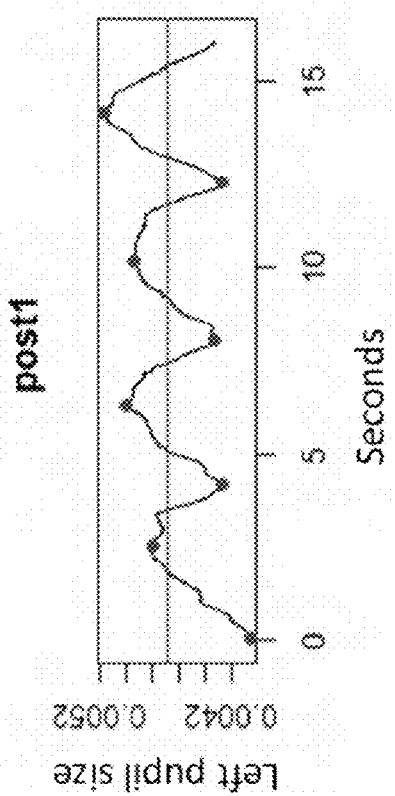

The third step in developing the algorithm was to use the intersection of the mean line with the curve (the "cross points" marked on the curve of FIG. 34) to form windows in which the local maximums and minimums reside. The local maximums and minimums of Post1 are marked with points on the curve of FIG. 35. FIGS. 36A-36B show the local maximums and minimums for all of the remaining HGN tracking test data, including the Baseline and Post2-Post7.

Next, in the fourth step of developing the algorithm, the left valleys were paired to the right peaks to create multiple peak-valley pairs.

At the fifth step, the peak value was divided by the valley value to obtain the peak-to-valley ratio (only one peak-to-valley ratio for each peak-valley pair). The distribution of these peak-to-valley ratios can be seen in the boxplot illustrated in FIG. 37.

The results of the pupil size during HGN test as illustrated in FIGS. 30-48 is representative of the type of information output as part of the impairment indication information 140 described above.

Pupil Size During HGN Test Results

Figure 37:
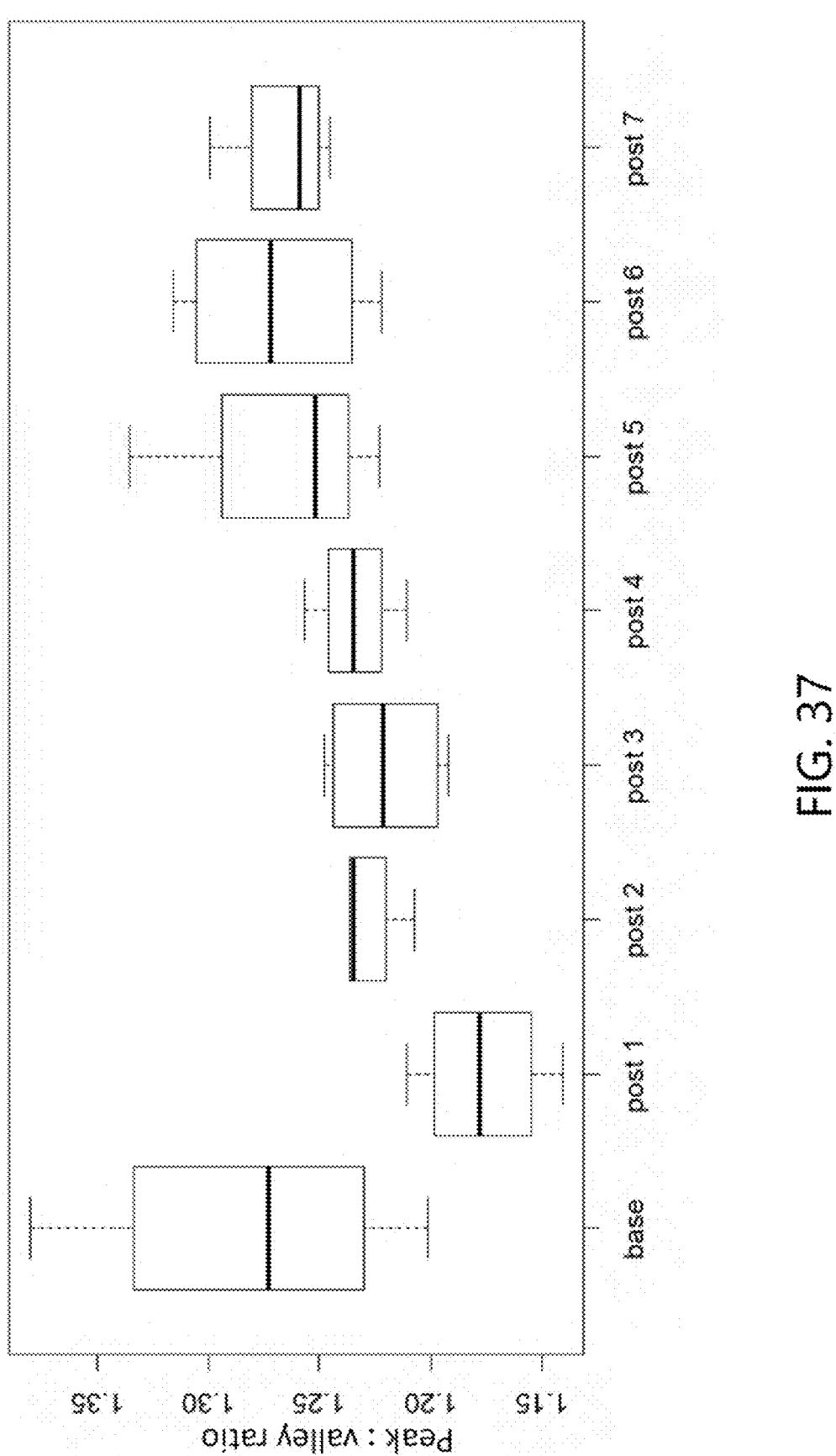
Figures 38, 39:
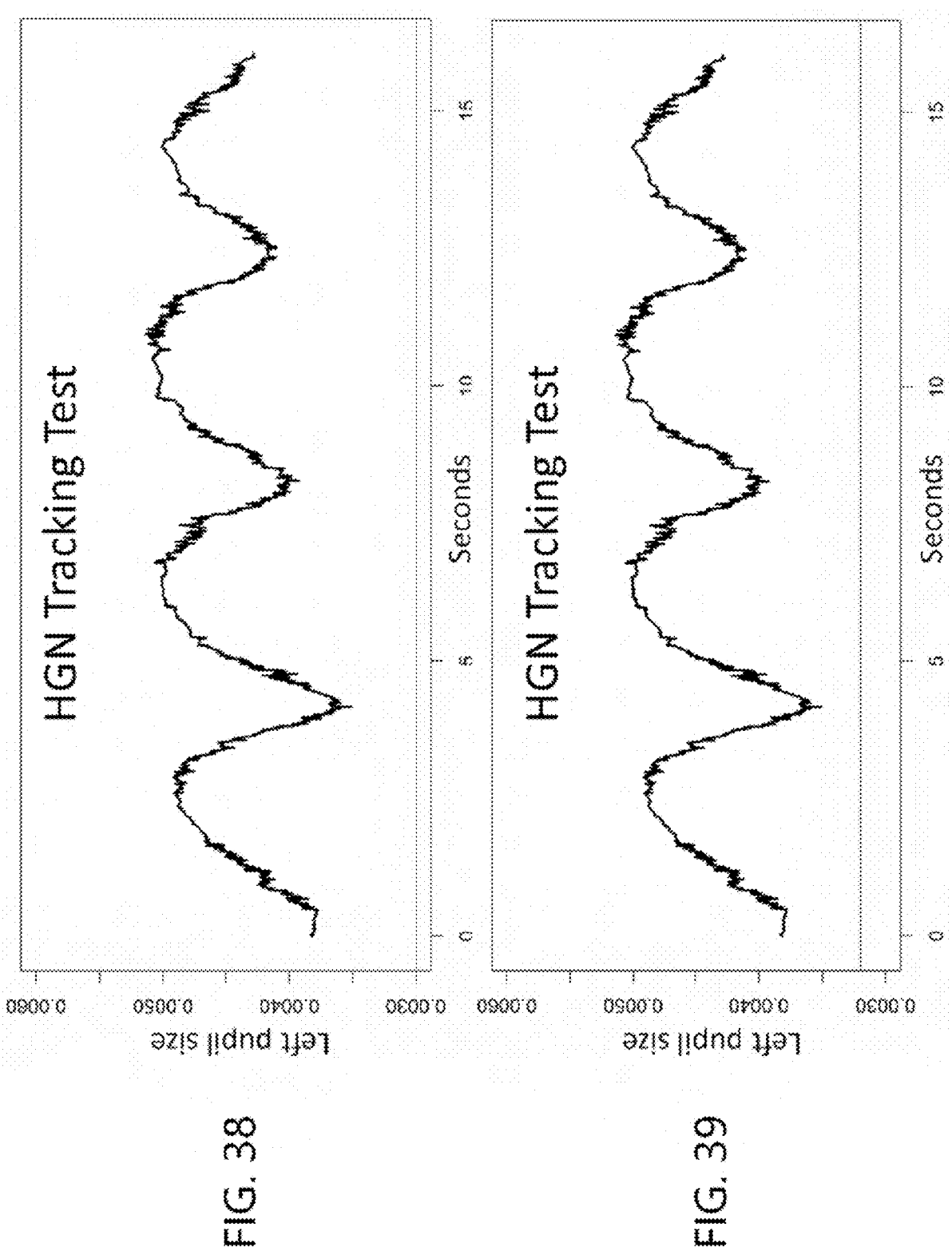
Figures 40, 41:
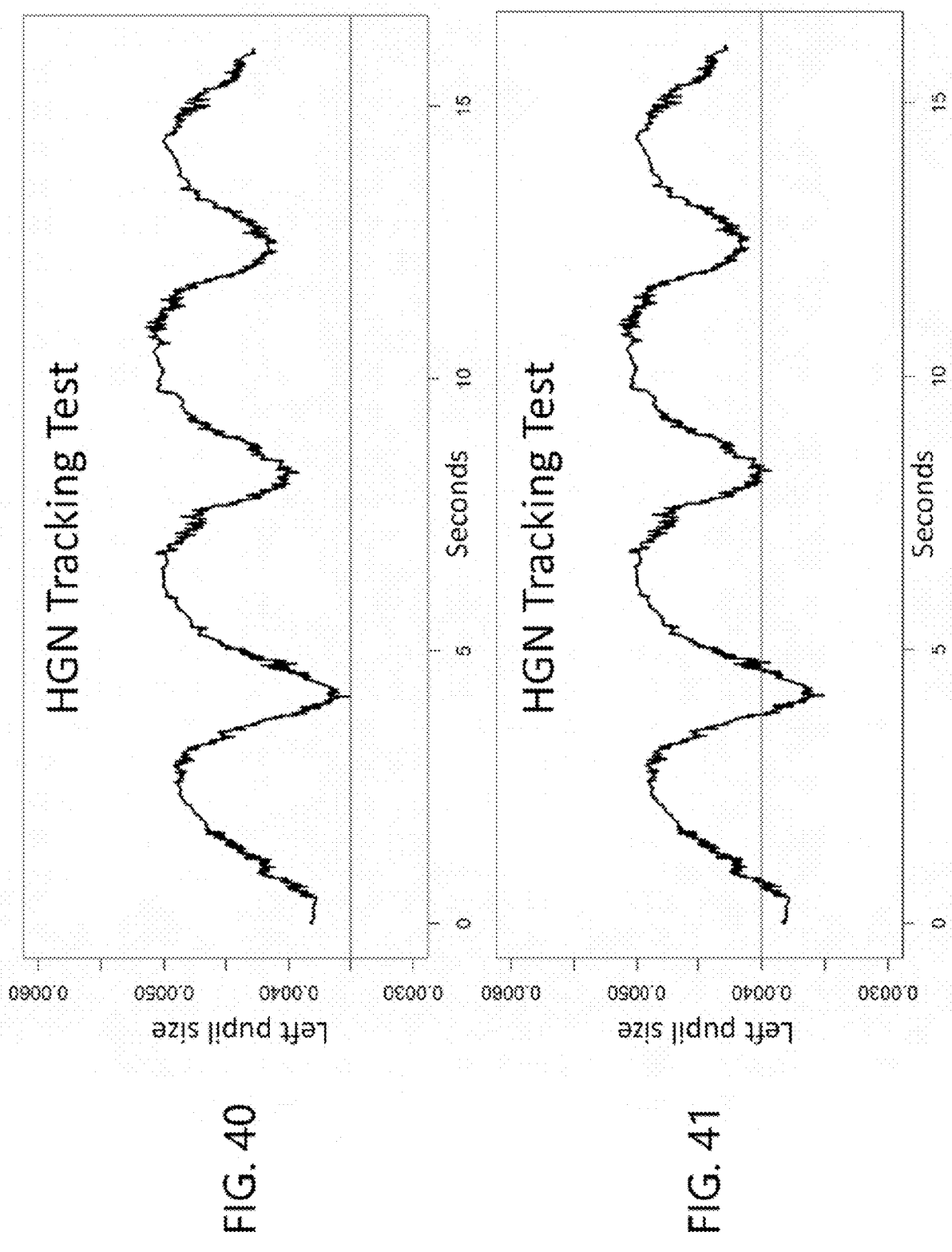
Figure 42:
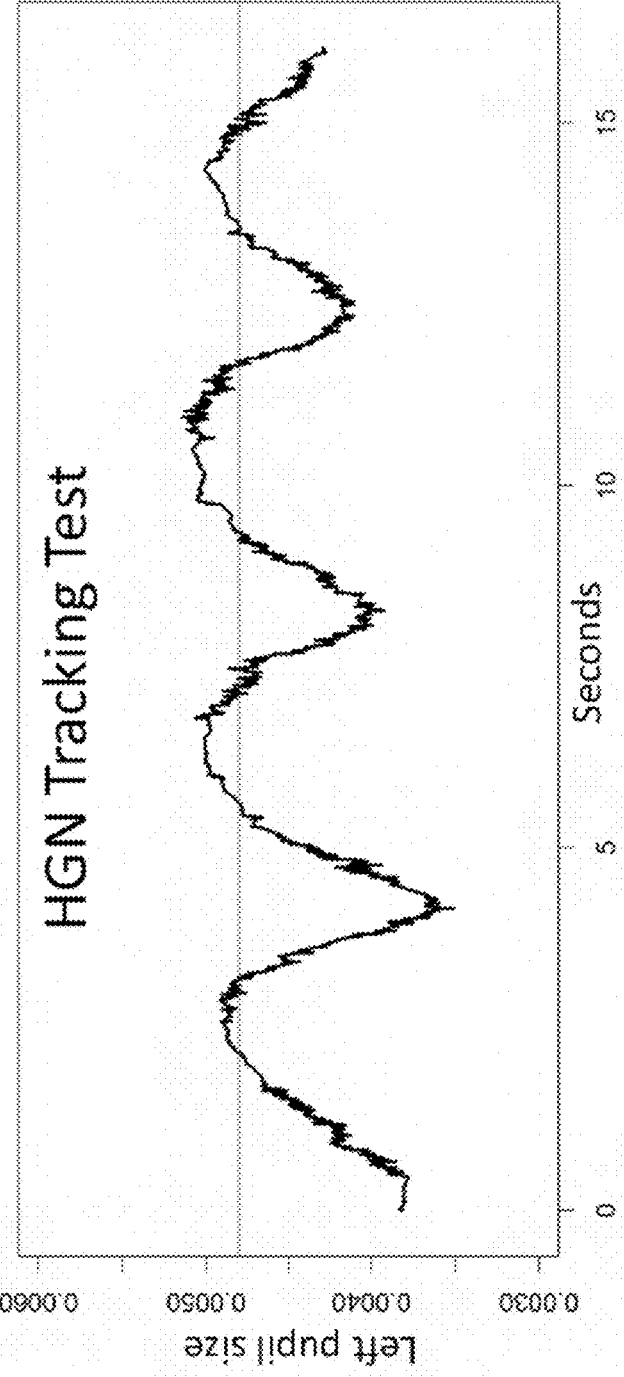

Referring to the boxplot of FIG. 37, the baseline has the highest median peak-to-valley ratio. There is a sharp decrease in median peak-to-valley ratio at Post1 and an increase in median peak-to-valley from Post2 to Post7, where the median peak-to-valley ratio at Post7 is approximately the same as the baseline ratio. These results indicate that the peak-to-valley ratio is potentially indicative of impairment, especially if the test subject was most impaired at Post1 (i.e., 10 minutes after smoking). However, it is noted that additional testing on more subjects is needed to verify that the peak-to-valley ratio is indicative of impairment.

Moreover, it is noted that some problems may arise using the peak and valley detecting algorithm described above. Ideally, it is desirable to modify the data as little as possible. However, the smoothing of the raw HGN tracking test data does require data modification which may result in peaks and/or valleys being missed if the curve does not cross the mean line at the peak/valley points. Thus, the smoothing step can potentially result in an inaccurate peak-to-valley ratio.

A method was thus developed to address the potential weaknesses discussed above. The aforementioned method is illustrated throughout FIGS. 38-48 and is based on an algebraic method known as persistent homology. Persistent homology is used to distinguish time series curves by their features. Examples of features for time series curves can be seen with reference to FIG. 38, where even though the curve is imperfect distinguishable peaks can still be seen at approximately 2.5, 6, 10.5, and 14.5 seconds, and distinguishable valleys can be seen at approximately 1, 4.5, 8.5, and 12 seconds.

Figure 43:
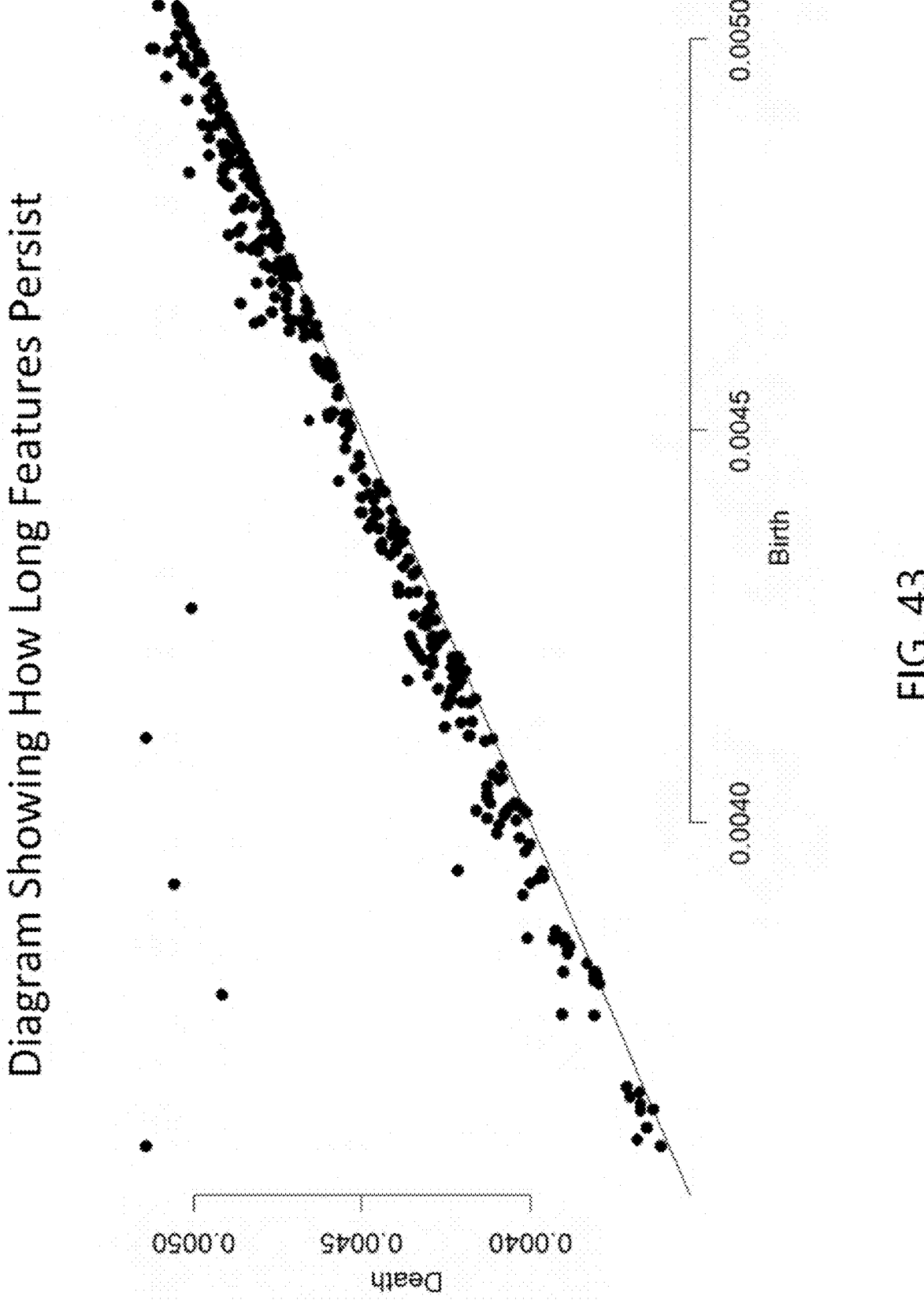
Figures 44, 45:
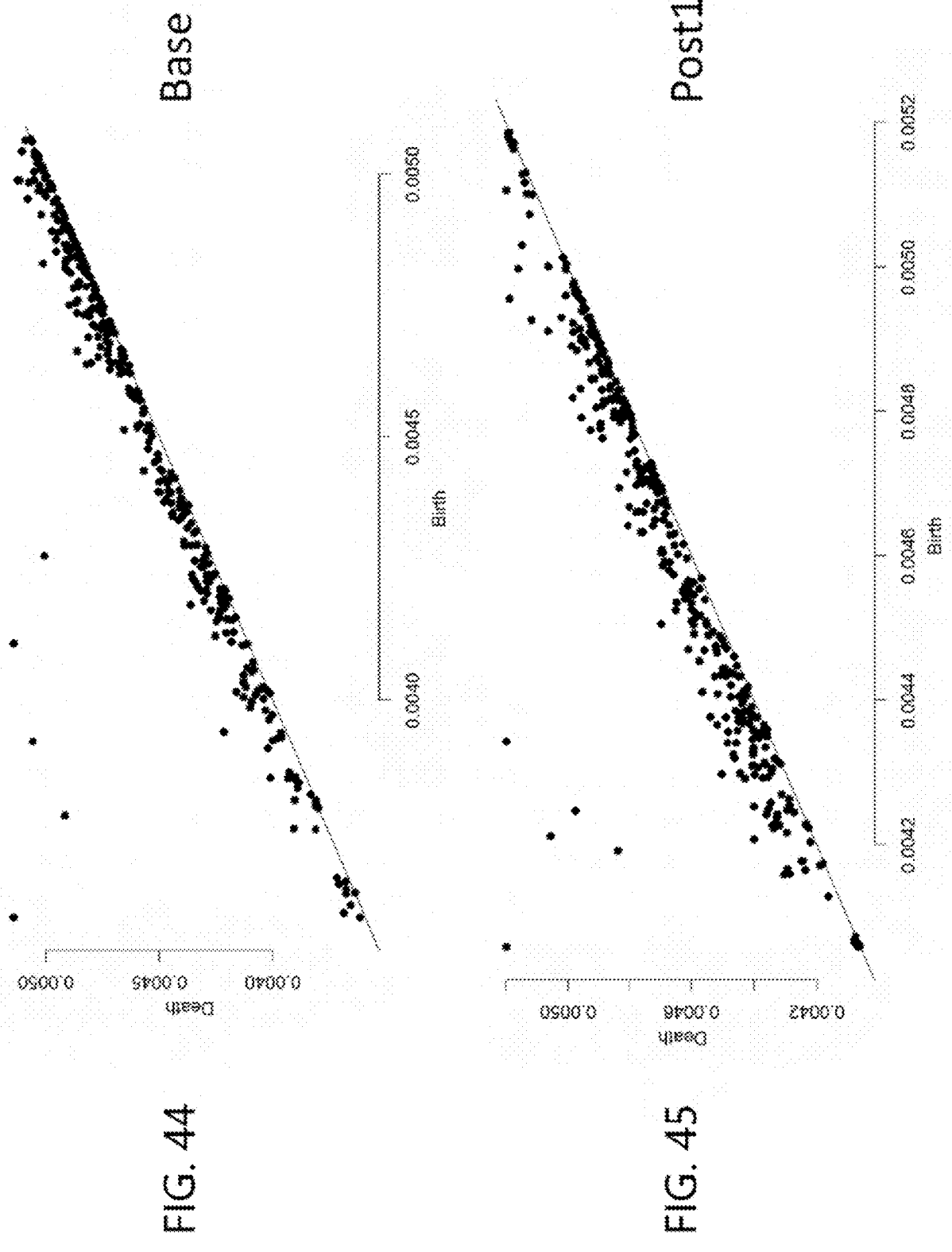

In order to implement persistent homology here, many lines are used to determine the location of the local maximums and minimums of the curve instead of one line (such as the mean line discussed above). FIGS. 38-42 illustrate this use of many lines to determine the location of the local maximums and minimums of the curve. The local maximums and minimums located from FIGS. 38-42 can be paired up to determine how long features persisted. The length of time these features persisted can be visualized in a birth-death diagram as illustrated in FIG. 43.

Thus, the time series curves can now be represented as a birth-death diagrams which can be compared using a mathematical metric since individual birth-death diagrams will look different for different curves. Such a comparison is illustrated between the baseline birth-death diagram of FIG. 44 and the Post1 birth-death diagram of FIG. 45. Diagrams that are close together are more similar, whereas diagrams that are far apart are more dissimilar.

Figure 46A:
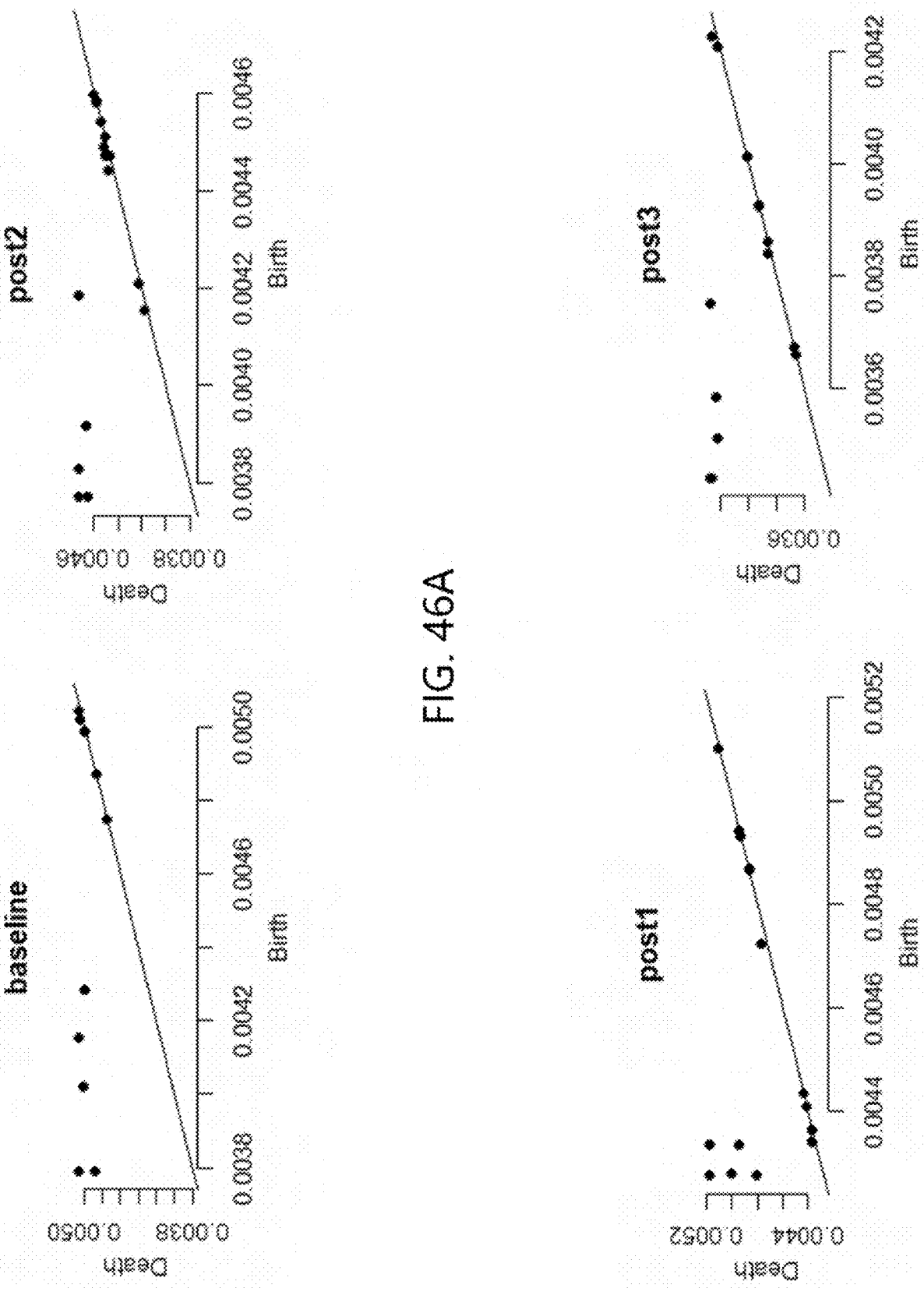
Figure 46B:
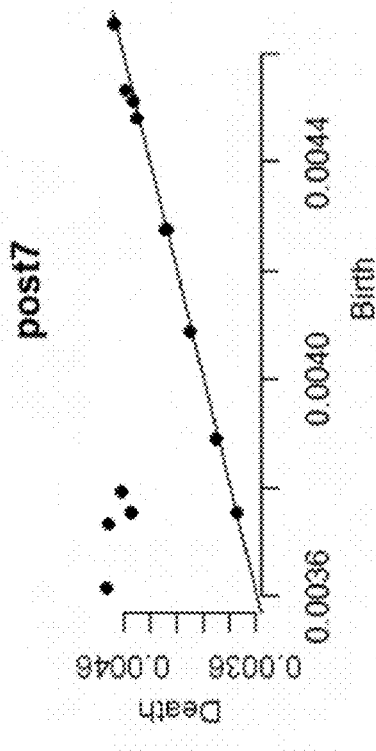
Figure 46B:
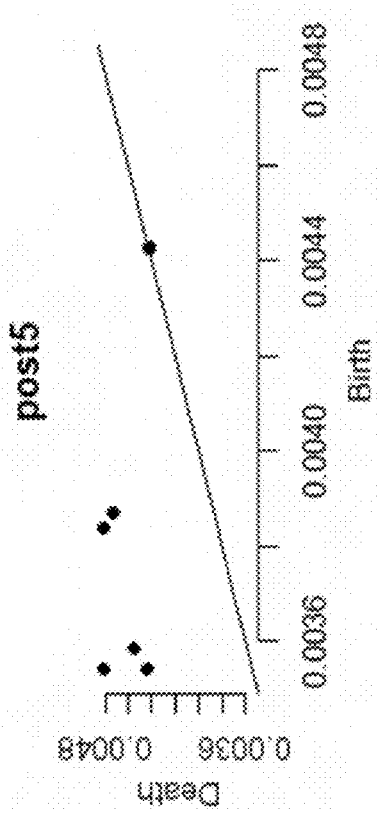
Figure 47:
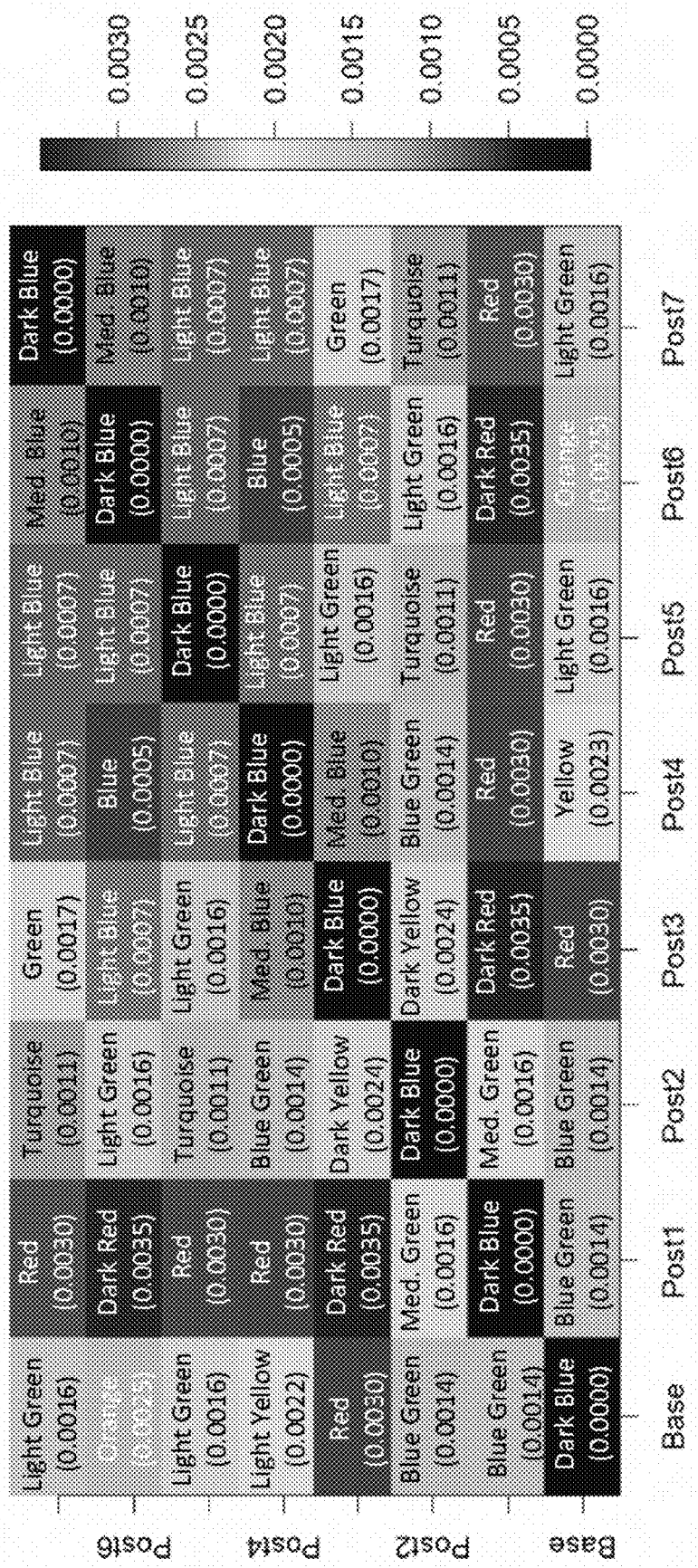

Referring now to FIGS. 46A-46B, birth-death diagrams are provided for each of the baseline and post-smoking times Post1-Post7. In FIG. 47, a distance matrix is provided which shows how close all the birth-death diagrams in FIGS. 46A-46B are to each other. The hot colors (colors toward the red end of the spectrum) in FIG. 47 represent being far apart and the cool colors (colors toward the blue end of the spectrum) indicate being close together. The diagonal in FIG. 47 is exactly 0 since a diagram is 0 distance from itself. The distance matrix in FIG. 47 is symmetric such that it can be read either by rows or by columns. FIG. 47 indicates the various colors and corresponding approximate values in each block to allow for non-color representative illustration.

Pupil Size During HGN Test with Persistent Homology Results

With continued reference to FIG. 47, Post3 was found to be the most different from the baseline as indicated by the red color at row 4, column 1, or by the red color at row 1, column 4. This may indicate that test subject B was the most impaired at Post3 (assuming test subject B was the least impaired at the baseline). Post4-Post7 were found to be the most similar, as represented by the cool colors in the upper right of the matrix in FIG. 47.

Figure 48:
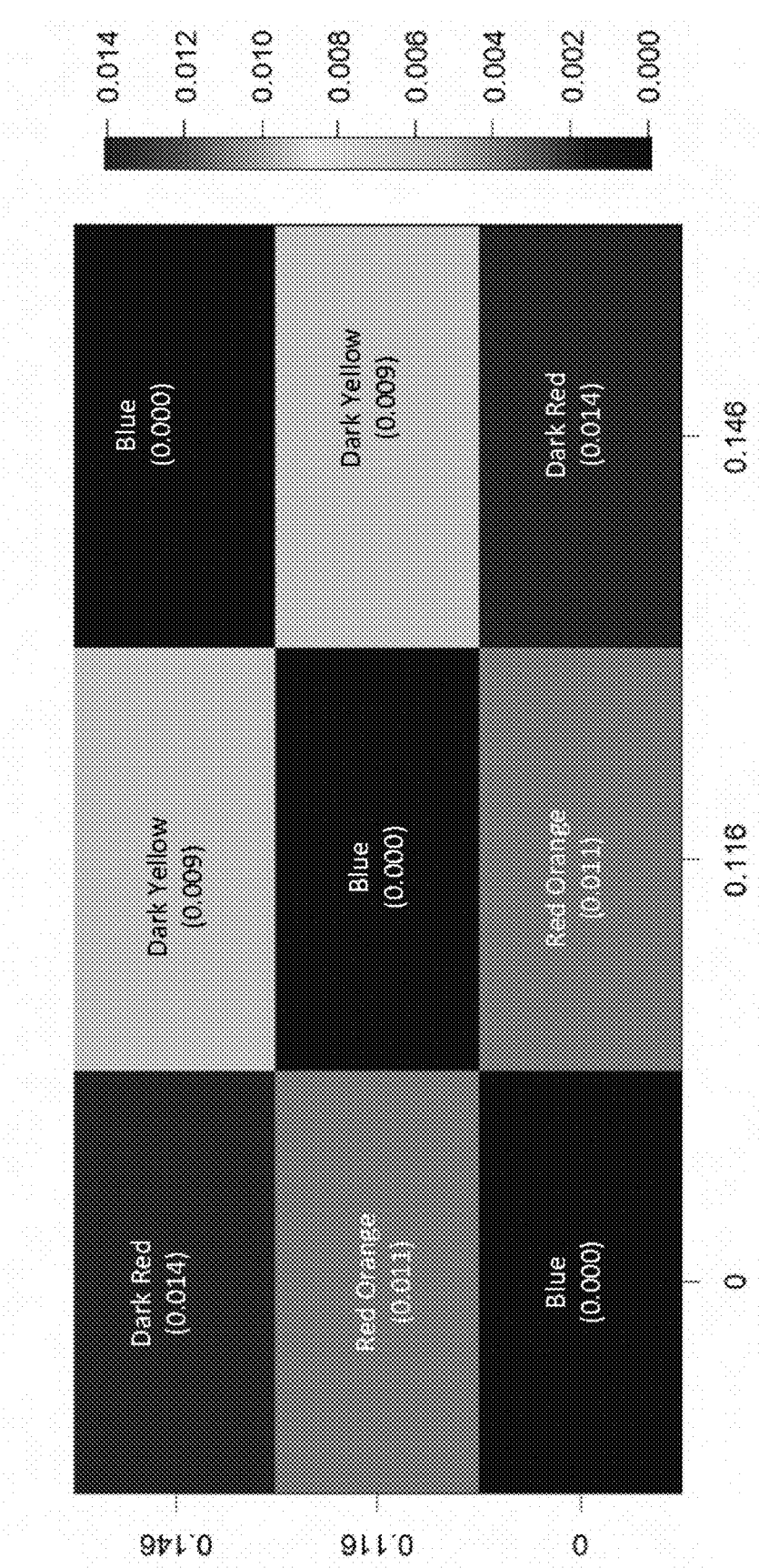
Figure 49:
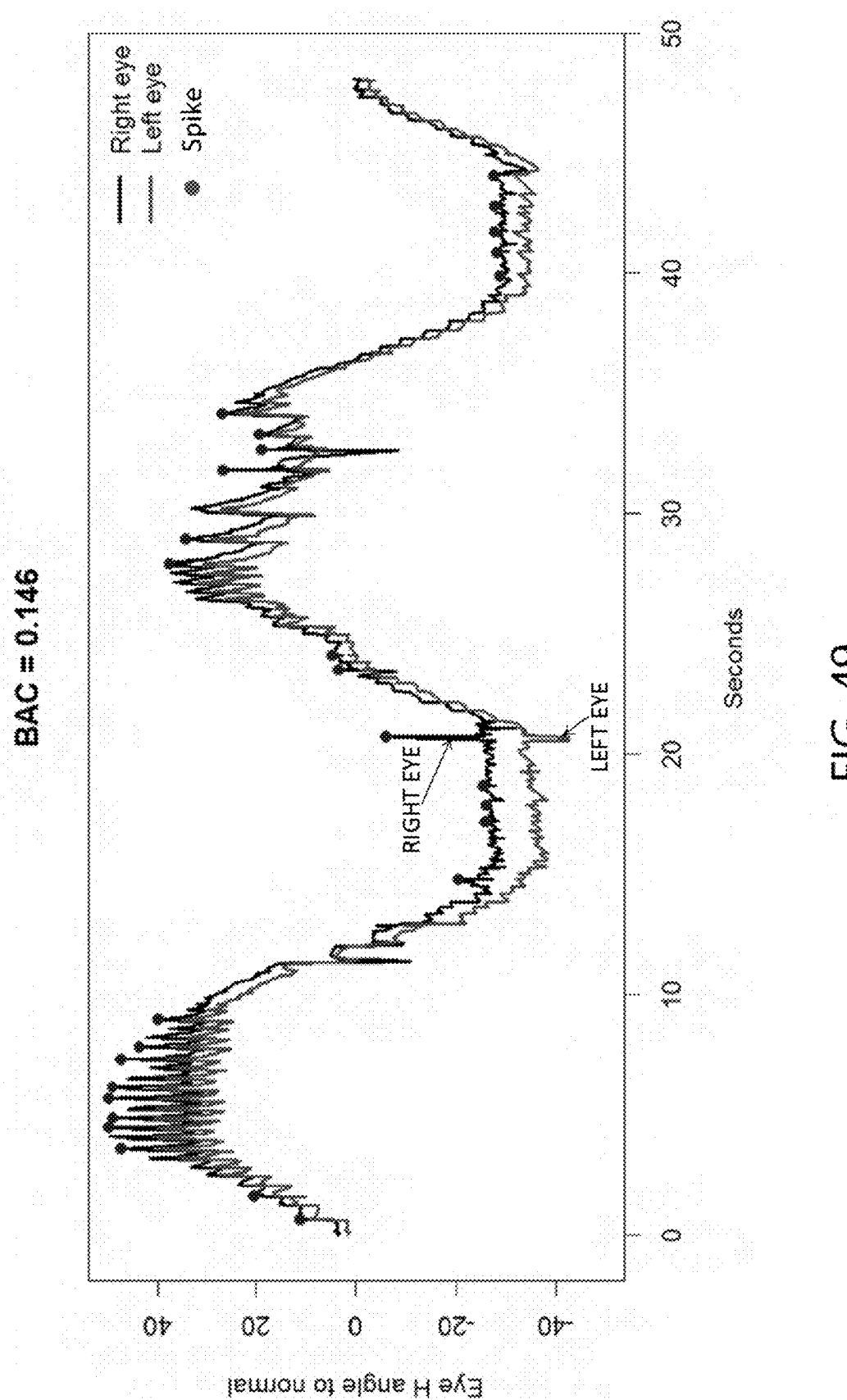
FIGS. 49-54 are illustrations of various charts and plots showing the data obtained from a HGN during HGN45 test and the results thereof; and, FIGS. 55-60 are illustrations of various charts and plots showing the data obtained from a targeting test and the results thereof.
Figure 50:
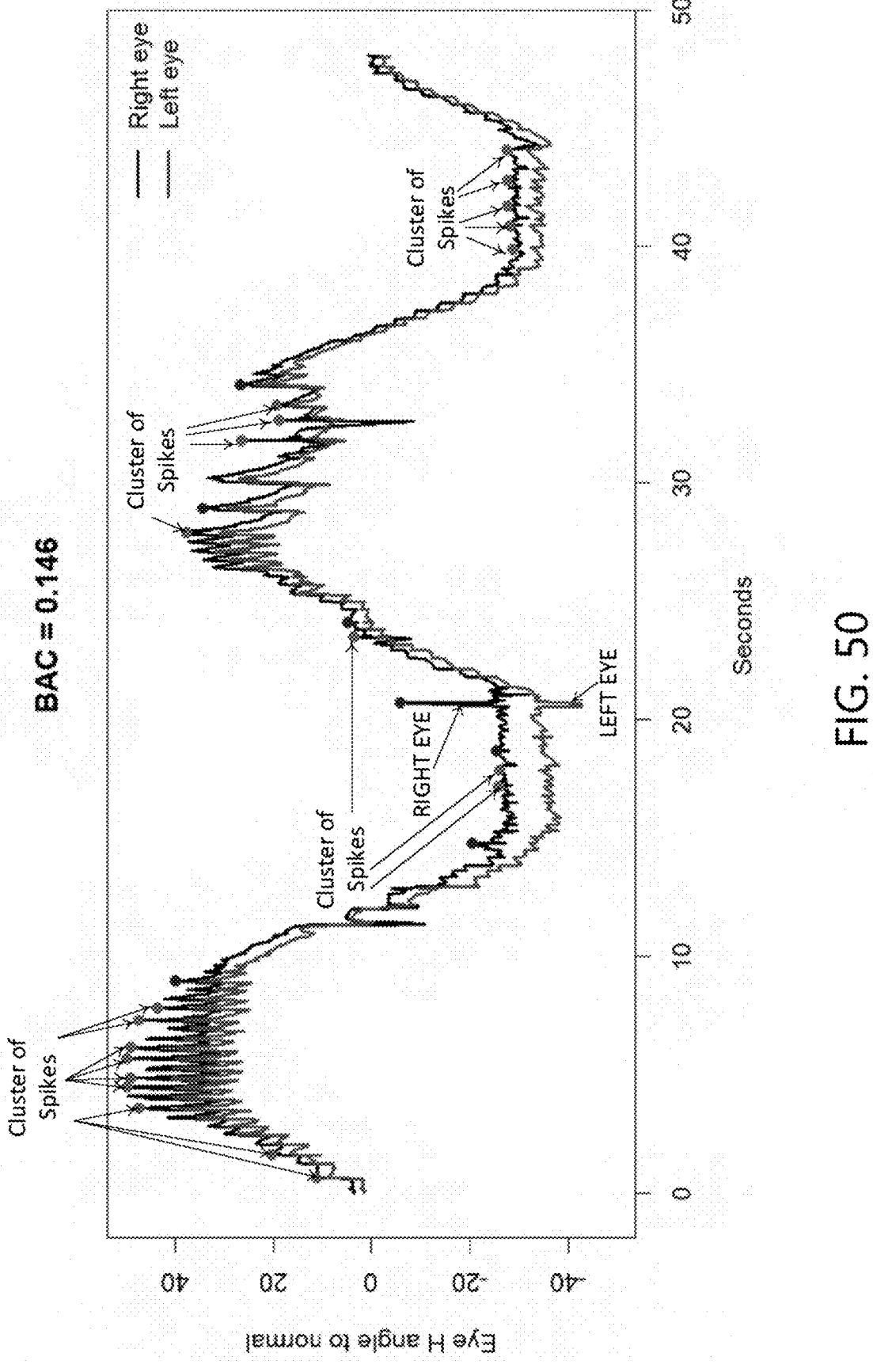
Figure 51:
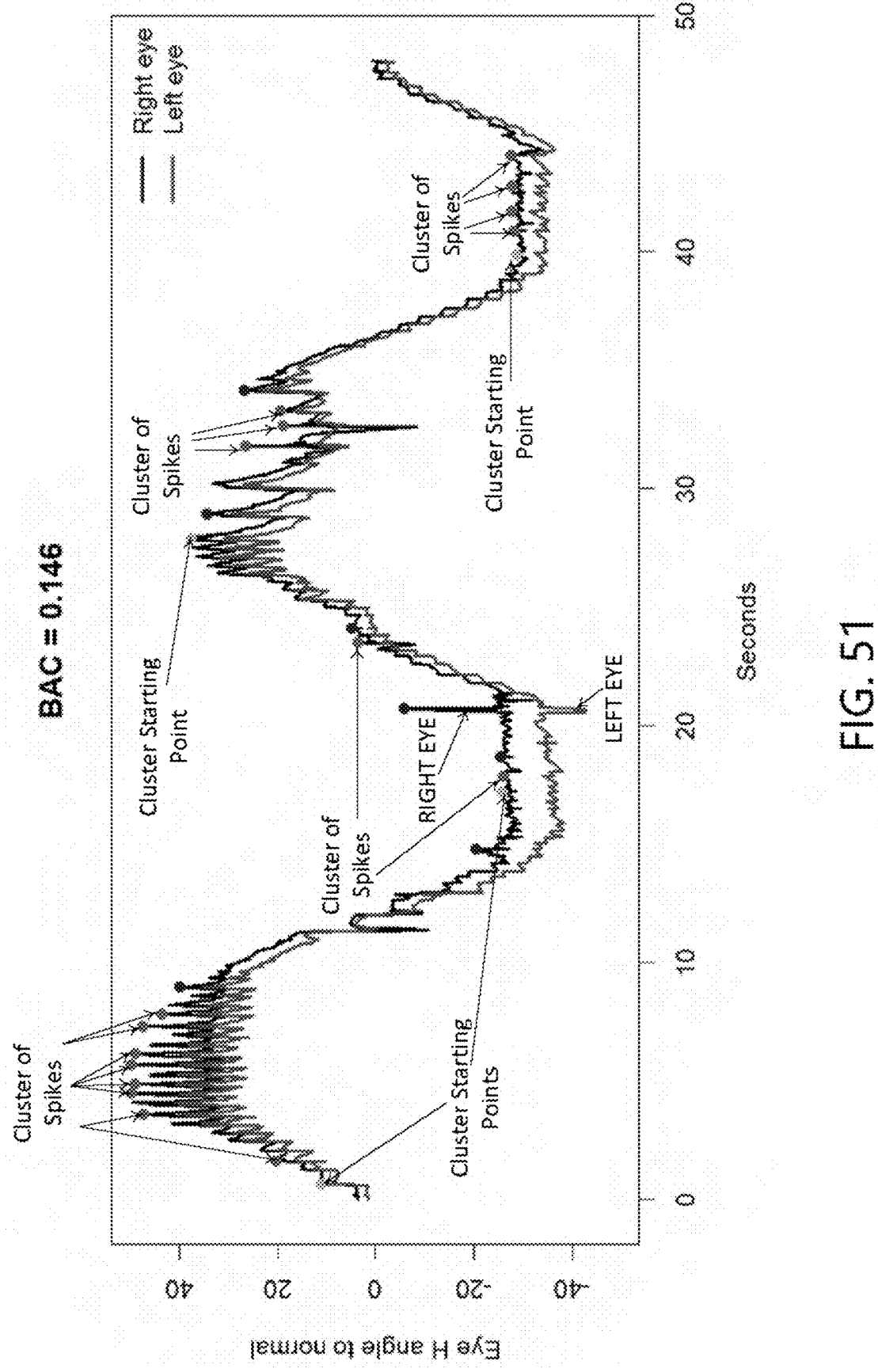

Referring now to FIG. 48, the same pupil size during HGN test with persistent homology was performed on the alcohol data from test subject A. These results are shown by the distance matrix in FIG. 48. The difference between increasing BAC levels and the baseline is evident, with the highest BAC of 0.146 being the most different from the baseline as indicated by the dark red color in row 3, column 1, or by the dark red color in row 1, column 3. Although additional testing for cannabis impairment is likely required, there is a clear relationship between BAC level and impairment as shown by the distance matrix of FIG. 48. As such, this suggests that the change in pupil size during the HGN test is a potential metric for determining cannabis impairment. FIG. 48 includes suitable labels denoting color and corresponding values for example purposes and non-color reproduction.

Horizontal Gaze Nystagmus During HGN45 Test

Turning now to FIGS. 49-54, the results of the HGN during HGN45 test are shown. the HGN during HGN45 test was developed in view of the HGN45 test results discussed above and shown in FIGS. 19 and 20. It was observed that clusters of spikes indicative of nystagmus occurred in the data obtained from test subject A (see, for example, the clusters of spikes occurring between about 5 and 8 seconds in FIG. 20). As such, it was desirable to determine when these clusters of spikes occur.

The data necessary for the HGN during HGN45 test was obtained using the right and left eye H angle to normal data from the HGN45 test data files described above. In order to implement HGN during HGN45 test on the VR headset, an algorithm was developed to detect the clusters of spikes. The algorithm development steps included first detecting when a spike occurs and then finding when a cluster of spikes occurs.

In order to detect the occurrence of a spike, irregularities in the data due to blinking of the test subject's eyes were first removed. In order to characterize the blinks for removal, the variables for the eye H angles to normal were set to a value of 999. Then, R programming language was used to find the spikes. More particularly, the "find_peaks" algorithm from the ggpmisc package in R was used with a span of 71 to find the spikes. The spikes are represented by the blue dots illustrated in FIG. 49.

In order to detect clusters of spikes indicative of nystagmus, a cluster was first defined as spikes which occur within a 2 second threshold of each other. However, a different threshold could also be used if desired. The clusters of spikes based on this definition are represented by the purple dots and designated as such, and individual spikes are represented as blue or undesignated dots illustrated in FIG. 50.

Figure 52:
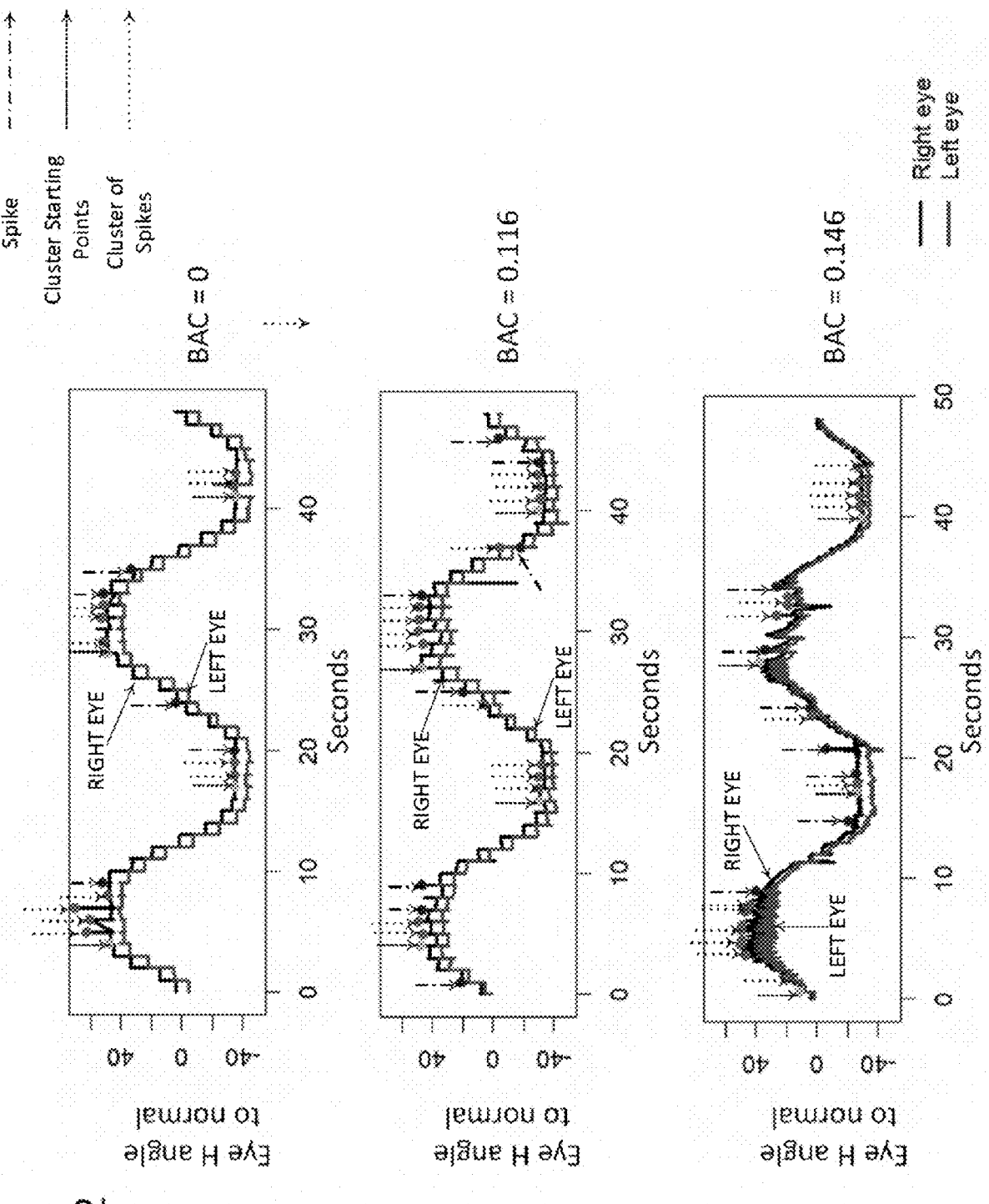

Next, it was desirable to detect the starting point for clusters of spikes indicative of nystagmus. The angle at which these clusters start gives the onset angle of nystagmus, and the start of the cluster is defined as the first spike in a cluster that occurs more than 10 seconds before the next cluster. However, a threshold value other than 10 seconds could also be used if desired. Cluster starting points based on this definition are represented by the orange dots (and designated as such) illustrated in FIG. 51. As shown in FIG. 52, the spike and clusters of spikes detection techniques described above were then applied to the time series curves for each of test subject A's BAC levels as shown in FIG. 19 and as discussed above.

Figure 53:
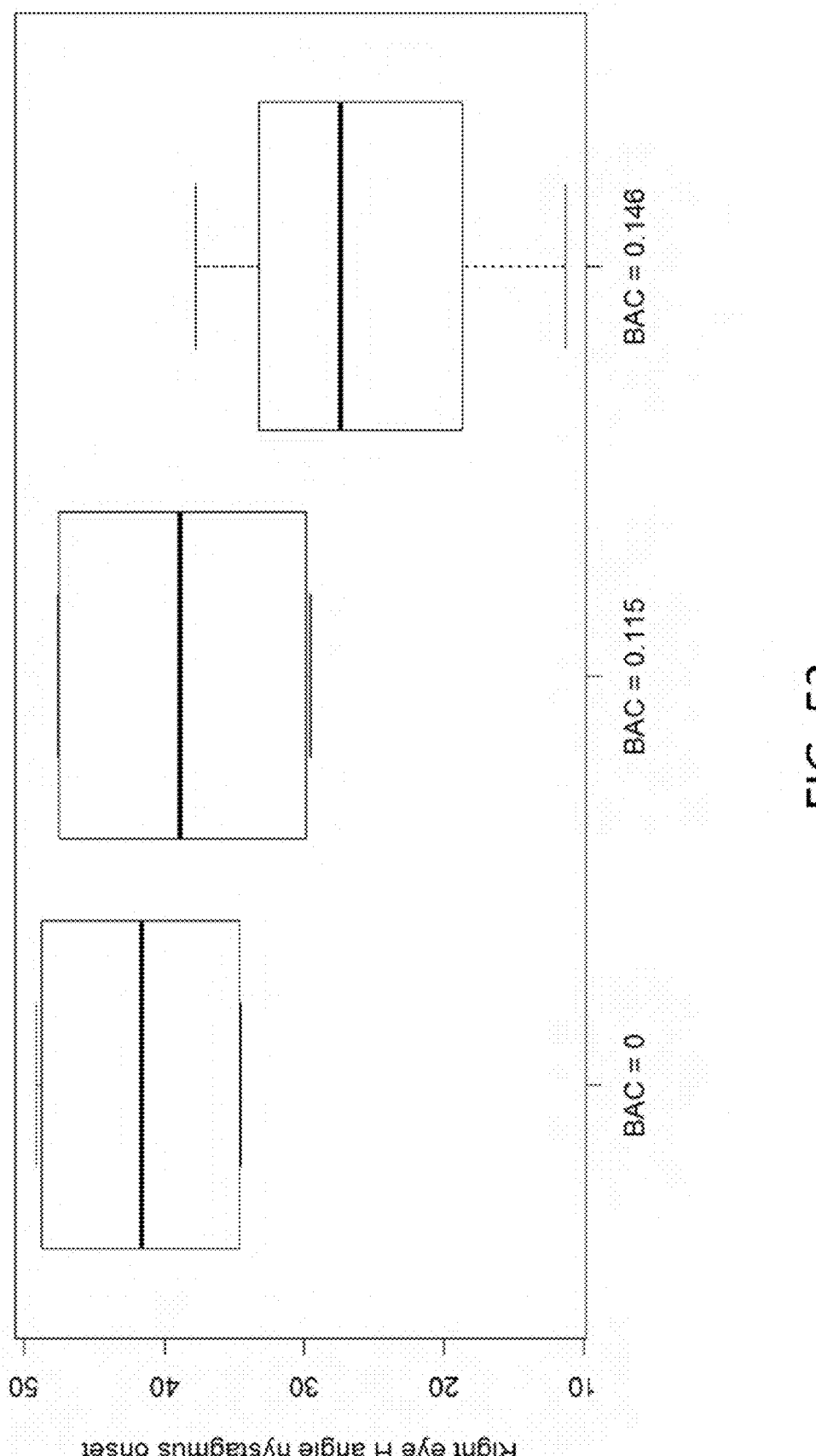

Next, the differences between the values represented by the orange dots (i.e., the starting points of clusters and the angles of onset of nystagmus) was found for all occurrences. Distributions for these differences were then analyzed to draw conclusions from the HGN during HGN45 test data obtained from test subject A. The distribution results for test subject A are illustrated in the boxplot of FIG. 53 (only the results for the right eye is shown but the left eye could also be used).

Figure 54:
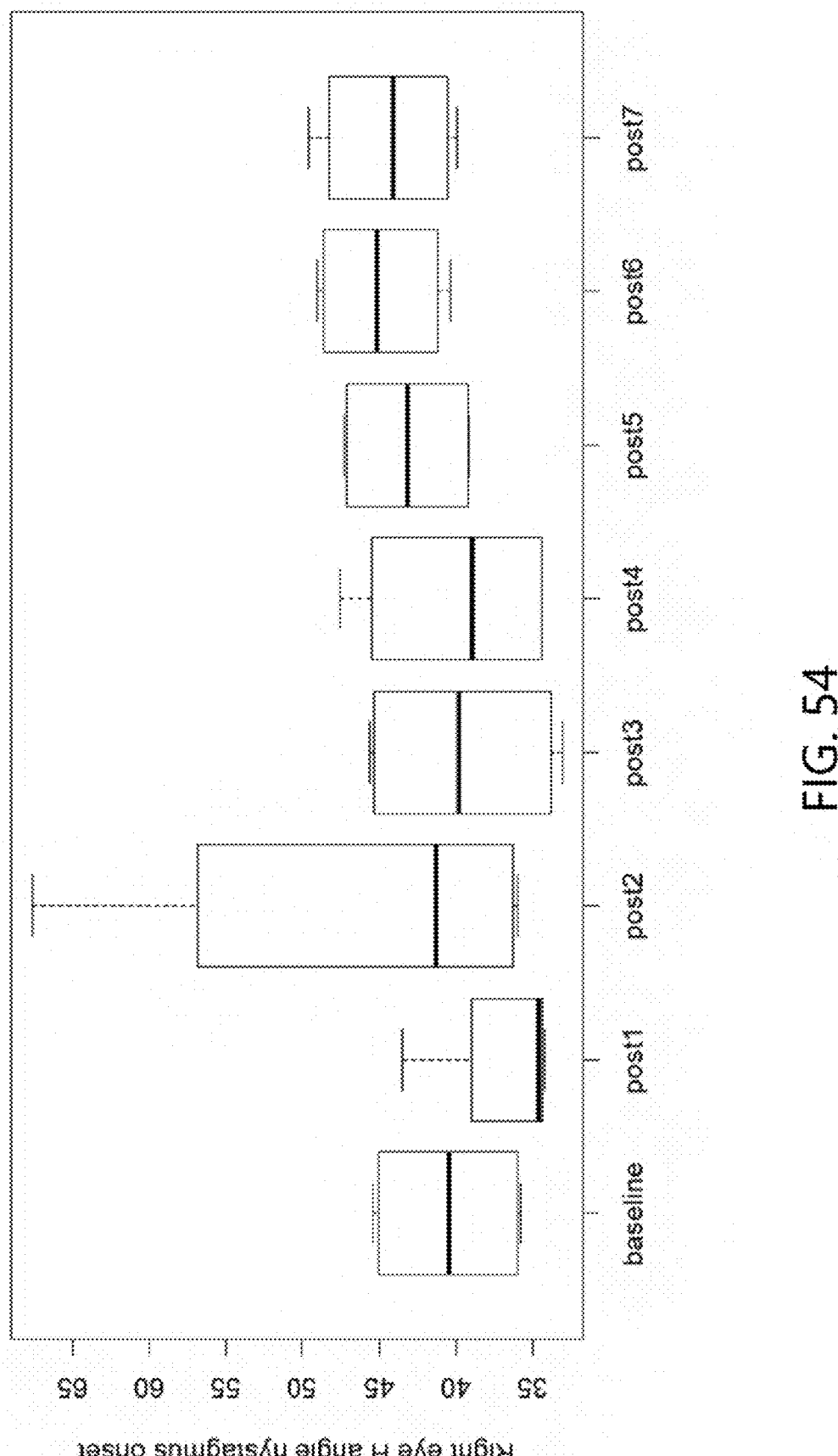
Figure 55:
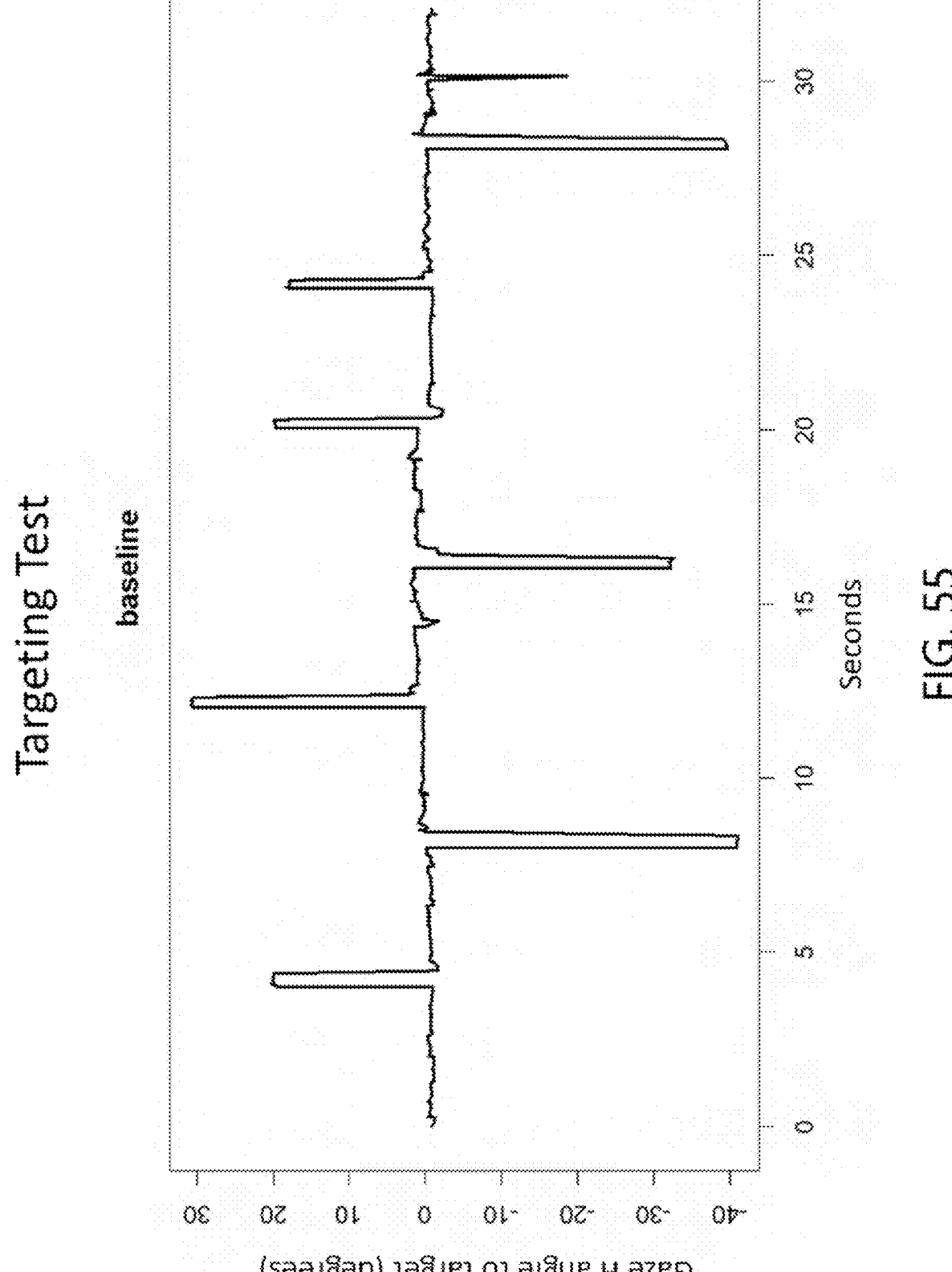
Figure 56:
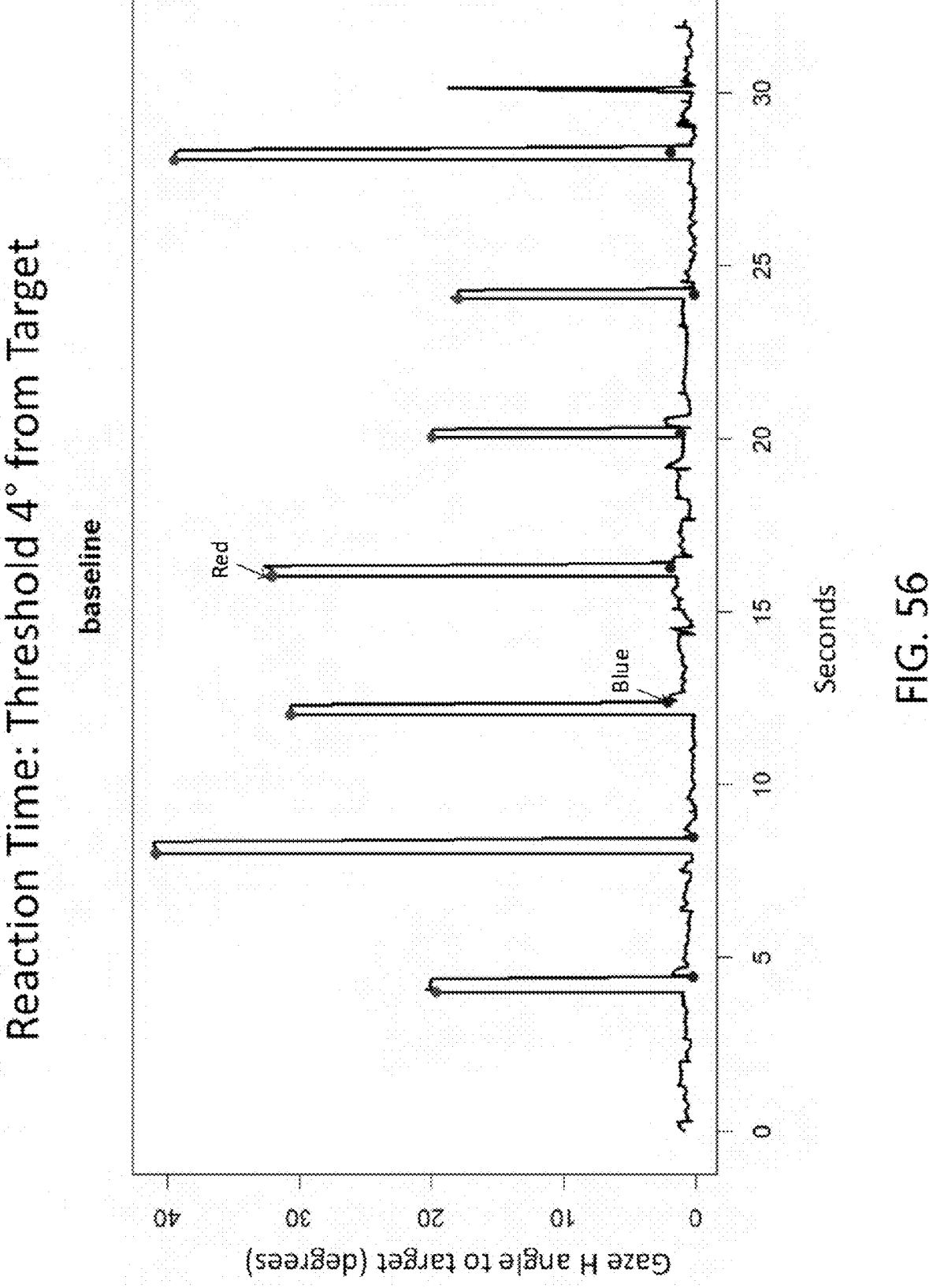

Moreover, this methodology was also applied to the HGN tracking test results obtained from test subject B as shown in FIGS. 2A-2B and as described above. The distribution results for test subject B are illustrated in the boxplot of FIG. 54 (only the results for the right eye are shown but the left eye could also be used).

The results of the HGN during HGN45 test shown in the charts and plots of FIGS. 49-54 are representative of the type of information output as part of the impairment indication information 140 described above.

Results of Horizontal Gaze Nystagmus During HGN45 Test

With reference to the boxplot of FIG. 53 for test subject A, the distribution of the absolute value of the y-value of the orange dots from the charts of FIG. 52 is represented. From FIG. 53, it can be seen that the angle of onset of nystagmus in the right eye decreased as the BAC of test subject A increased.

With reference to the boxplot of FIG. 54 for test subject B, the distribution of the absolute values of the y-value of the orange dots determined from the data illustrated in FIGS. 2A-2B is represented. From FIG. 54, it can be seen that the smallest angle of onset appeared to occur at Post1. In addition, the angle of onset generally appeared to increase with post-smoking time. However, more testing of cannabis impaired subjects I likely required to determine if the angles of nystagmus onset illustrated in FIG. 54 are indicators of impairment.

With reference to the boxplots of FIGS. 27A and 27B for test subject B, the distributions for the differences between eye H angles to normal appeared to be similar within the respective "far from" and "close to" groups. The largest differences occurred in Post3 of FIGS. 27A and 27B, which likely indicates that test subject B exhibited the highest level of cannabis impairment at Post3. With reference to the boxplots of FIGS. 28A and 28B for test subject A, in can be seen that in both the "far from" and "close to" groups, the median differences between eye H angles to normal decreased as the BAC of test subject A increased.

Targeting Test

Referring now to FIGS. 55-60, the results of a targeting test performed on test subject B are shown. The targeting test measures the test subject's ability to detect the presence of an object appearing in the test subject's field of vision and the test subject's ability to focus their gaze on that object. The VR headset 102 administers the targeting test by making an object appear at several locations for a set amount of time in the test subject's field of vision. For example, the results of a baseline targeting test shown in FIG. 55.

It is noted that, for purposes of the impairment testing examples disclosed herein, the targeting test was only administered to test subject B. However, the targeting test could be administered to test subject A if desired. The methodology for implementing and administering the targeting test with the VR headset for test subject A would be identical to the methodology described below for test subject B.

Figure 59:
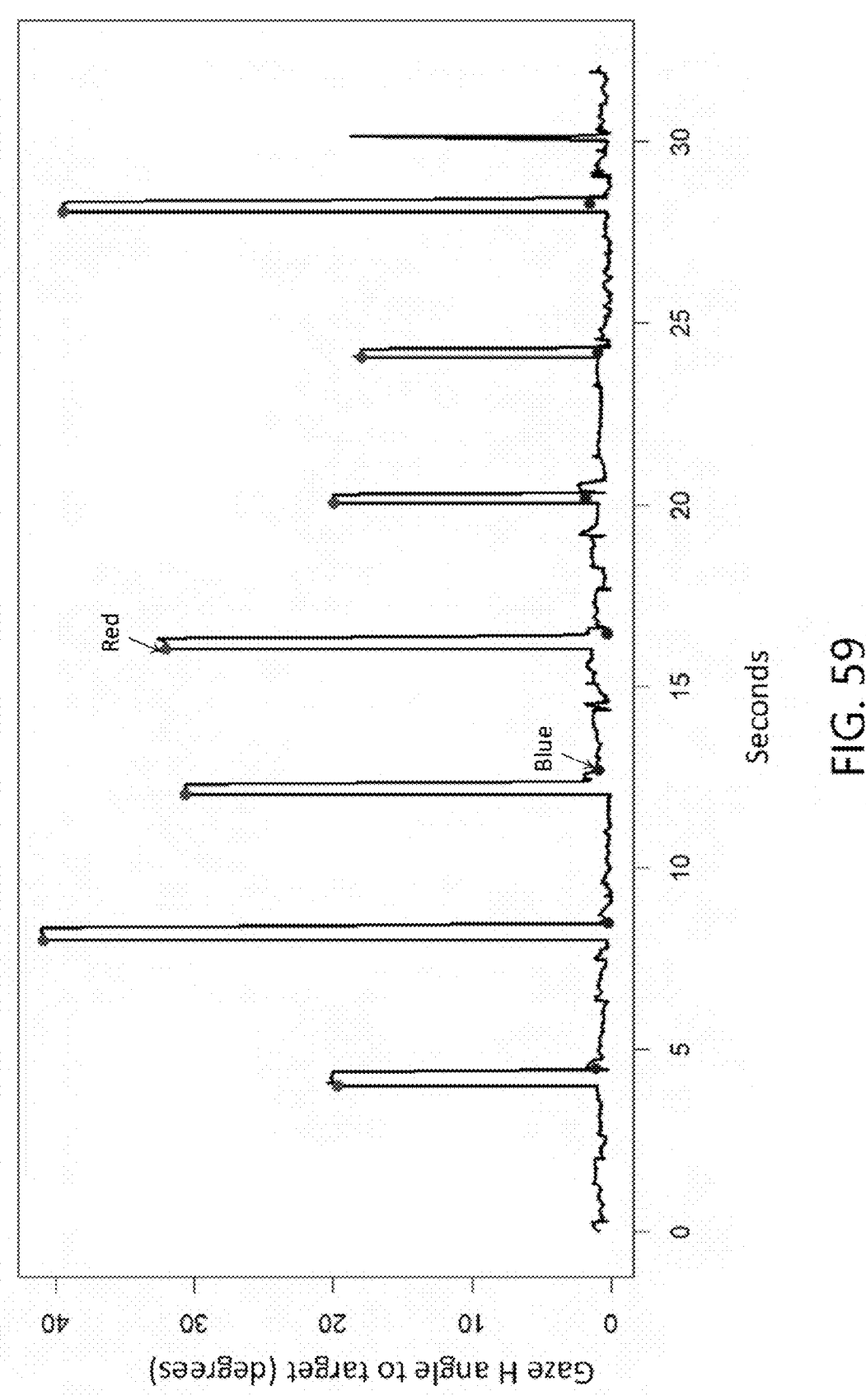

In order to implement the targeting test on the VR headset 102, an algorithm was developed to determine the time it took for the subject to identify the target in their field of vision and the time it took for the subject to accurately track the target. With reference to the baseline results illustrated in FIG. 56, target identification or reaction time is defined as the moment the gaze H angle to target was within a 4-degree threshold of the target coming into test subject B's field of vision. With reference to FIG. 59, the target tracking accuracy time is defined as the moment the gaze H angle to target was within a 1-degree threshold of the target coming into test subject B's field of vision. The variables GazeToTargetCaseHAngle and TrackedObjectX were used in the data file for the Targeting Test, and the variable TrackedObjectX was used to find the time when the target came into the subject's field of view.

The steps of the developed algorithm included first removing blinks by setting a gaze to target cast H angle of 999 degrees. Next, the gaze to target cast H angle data was normalized so that all values were positive. Then, the time when the target appeared in the test subject's field of view was found. Since the x value of the target had unique discrete values throughout the test, the time that the target appeared is the time when these discrete values changed.

Next, the first time when the gaze to target cast H angle was within 4 degrees (i.e., the reaction time, represented by the blue dots in FIG. 56) or within 1 degree (i.e., the accuracy time, represented by the blue dots in FIG. 59). Then, the difference between the time of the target's appearance and the time of either reaction or accuracy (i.e., the time of the blue dot minus the time of the red dots) was found for all occurrences. The distributions for the reaction times is shown by the boxplot in FIG. 57 and the distributions for the accuracy times is shown by the boxplot in FIG. 60.

The results of the targeting test as illustrated in FIGS. 55-60 is representative of the type of information output as part of the impairment indication information 140 described above.

Targeting Test Results

Figure 57:
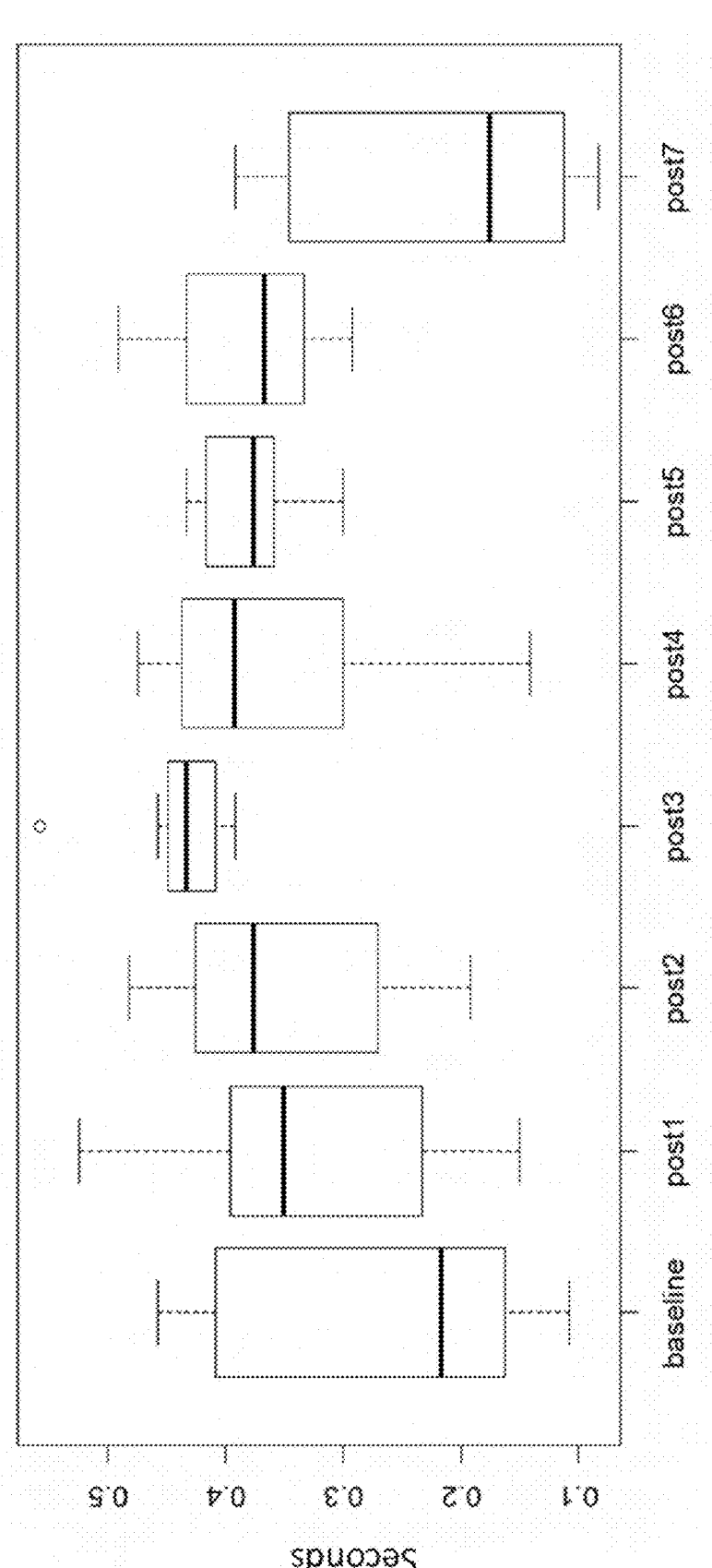
Figure 58:
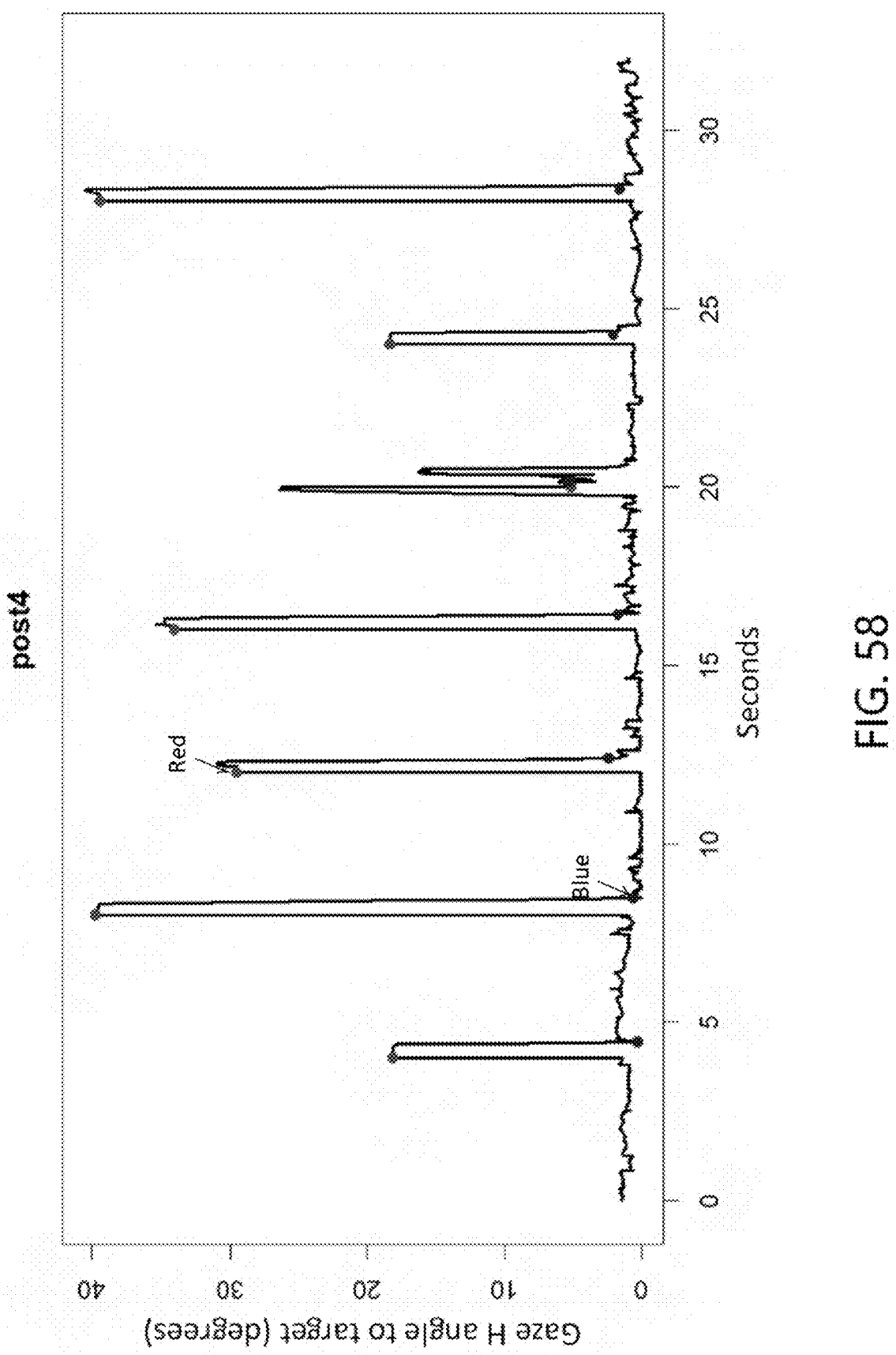

With reference to the boxplot of FIG. 57 showing the distribution for reaction times, the median reaction time increased from the baseline and peaked at Post3. The fastest median reaction time occurred at Post7. Moreover, the variability in reaction time (represented by the length of the box/interquartile range) generally decreased with an increase in post-smoking time up to Post7. This would indicate that reaction time is a potential indicator indicative of cannabis impairment, especially when test subject B was most impaired at Post3.

Figure 60:
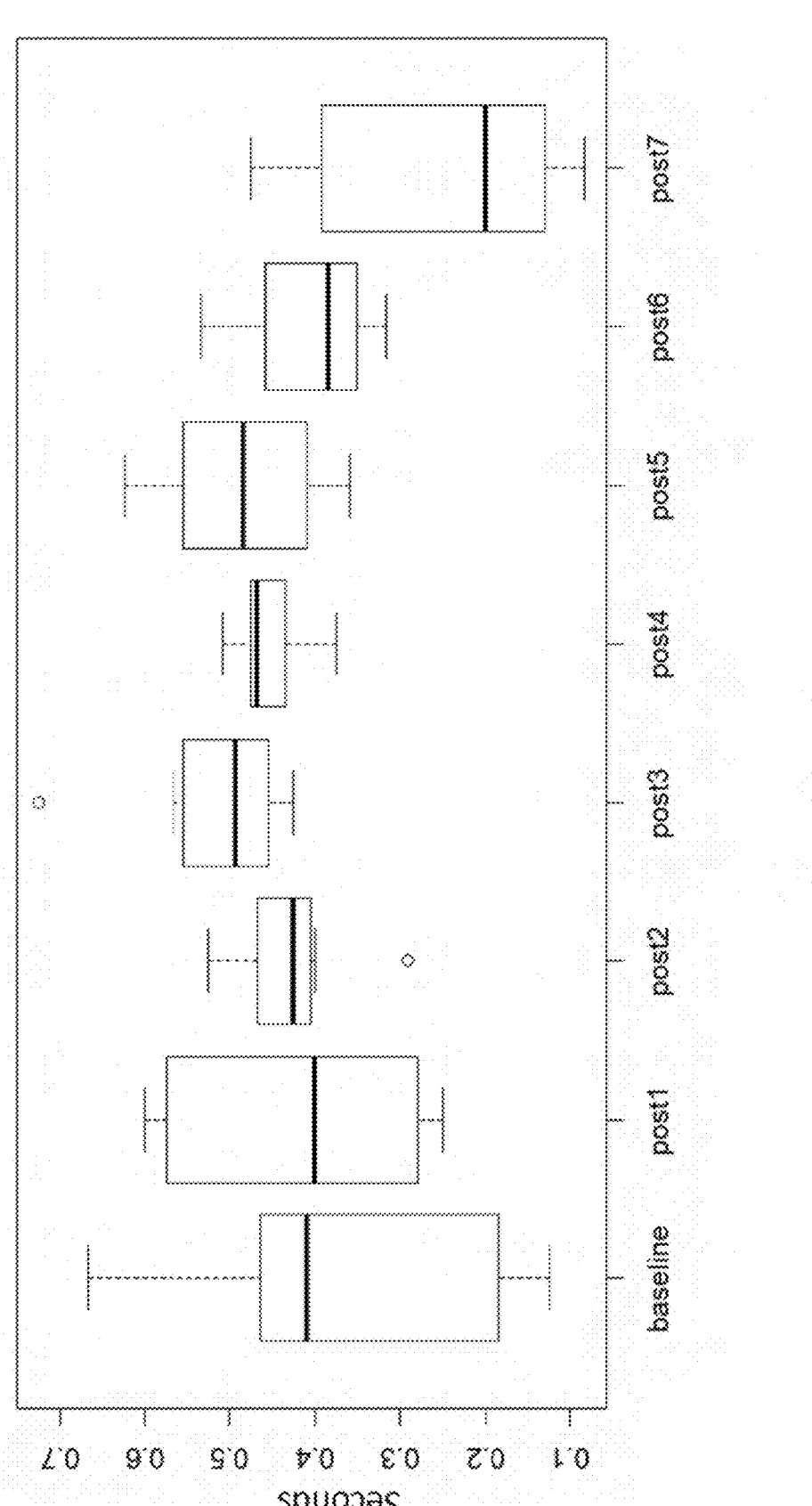

With reference to the boxplot of FIG. 60 showing the distribution for accuracy times, the median accuracy time steadily increased from the baseline, peaked at Post3, and then steadily decreased to Post7, with Post7 having the fastest median accuracy time. The variability in accuracy time was lowest for Post2-Post6, which indicates that time to accuracy was slow throughout the test. Moreover, there is evidence that test subject B memorized the location of the target. This is shown by the fastest reaction and accuracy times occurring at Post7, and with reference to FIG. 58, the almost instant reaction time occurring at Post4 around 20 seconds into the test. The effects of memorization by test subjects can be countered by configuring the VR headset to randomize target placement.

Some further embodiments are described below.

Some embodiments comprise a set of metrics as shown in FIGS. 2-5 and discussed above for determining impairment from drugs or alcohol using data obtained during an equal pupil test implemented by a VR headset as shown in FIG. 1 and discussed above.

Some embodiments comprise a set of metrics as shown in FIGS. 6-11 and discussed above for determining impairment from drugs or alcohol using data obtained during a horizontal gaze nystagmus (HGN) test implemented by a VR headset as shown in FIG. 1 and discussed above.

Some embodiments comprise a set of metrics as shown in FIGS. 12-18 and discussed above for determining impairment from drugs or alcohol using data obtained during a pupil rebound test implemented by a VR headset as shown in FIG. 1 and discussed above.

Some embodiments comprise a set of metrics as shown in FIGS. 19-21B and discussed above for determining impairment from drugs or alcohol using data obtained during an HGN45 test implemented by a VR headset as shown in FIG. 1 and discussed above.

Some embodiments comprise a set of metrics as shown in FIGS. 22A-28B and discussed above for determining impairment from drugs or alcohol using data obtained during an LOC test implemented by a VR headset as shown in FIG. 1 and discussed above.

Some embodiments comprise a set of metrics as shown in FIG. 29 and discussed above for determining impairment from drugs or alcohol using data obtained during a Modified Romberg test implemented by a VR headset as shown in FIG. 1 and discussed above.

Some embodiments comprise a set of metrics as shown in FIGS. 30-48 and discussed above for determining impairment from drugs or alcohol using data obtained from a pupil size during HGN test implemented by a VR headset as shown in FIG. 1 and discussed above.

Some embodiments comprise a set of metrics as shown in FIGS. 49-54 and discussed above for determining impairment from drugs or alcohol using data obtained from an HGN during HGN45 test implemented by a VR headset as shown in FIG. 1 and discussed above.

Some embodiments comprise a set of metrics as shown in FIG. 55-60 and discussed above for determining impairment from drugs or alcohol using data obtained during a targeting test implemented by a VR headset as shown in FIG. 1 and discussed above.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

To aid the Patent Office and any readers of this application and any resulting patent in interpreting the claims appended hereto, applicants do not intend any of the appended claims or claim elements to invoke 35 U.S.C. § 112(f) unless the words "means for" or "step for" are explicitly used in the particular claim.

The invention claimed is:

1. An impairment assessment device comprising:
a virtual reality (VR) headset configured to be worn by a test subject;
an eye tracker included with the VR headset;
an external display; and
at least one electronic processor programmed to perform an impairment assessment test by operations including:
controlling the VR headset to display a virtual scene;
measuring a change in one or more features of the test subject's eyes to obtain eye-tracking data, the eye-tracking data including pupil size and gaze direction, in response to the display of the virtual scene using the eye tracker;
determining a median reaction time, a variability in reaction time, a median accuracy time, and a variability in accuracy time of the test subject's gaze acquisition on a first displayed object in the virtual scene, which are calculated by processing the eye-tracking data and removing artifacts;
tracking changes in pupil size in the eye-tracking data in response to changes in light intensity in the virtual scene, applying a segmented regression analysis to identify a transition point at which a pupil response stabilizes, and calculating a pupil rebound speed based on a slope of the change in pupil size;
computing impairment indicator information from (i) the measured change in the one or more features of the test subject's eyes, (ii) the median reaction time, (iii) the variability in reaction time, (iv) the median accuracy time, (v) the variability in accuracy time, and (vi) the pupil rebound speed, wherein the impairment indicator information is indicative of impairment of the test subject; and
presenting a representation of the impairment indicator information on the external display or the VR headset.

2. The impairment assessment device of claim 1 wherein the at least one electronic processor is further programmed to:
cyclically move a second displayed object towards and away from an edge of the test subject's vision during the display of the virtual scene;
measure an angle of the test subject's eye as a function of time during the movement of the second displayed object; and
identify nystagmus in the measured angle of the test subject's eye as a function of time during the computation of impairment indicator information.

3. The impairment assessment device of claim 2 wherein the at least one electronic processor is further configured to identify nystagmus by operations including fitting a line through the angle of the test subject's eye as a function of time to produce a fitted line and computing deviations between the fitted line and the angle of the test subject's eye as a function of time.

4. The impairment assessment device of claim 3 wherein the computing further includes, prior to fitting the line, smoothing the angle of the test subject's eye as a function of time using a Loess smoothing window.

5. The impairment assessment device of claim 4 wherein the at least one electronic processor is further configured to compute impairment indicator information by identifying an onset angle of the nystagmus in the measured angle of the test subject's eye as a function of time.

6. The impairment assessment device of claim 1 wherein the at least one electronic processor is further programmed to:

move a third displayed object on a cyclic trajectory towards and away from a bridge of a nose of the test subject during the display of the virtual scene;

measure a difference between a left eye angle and a right eye angle at one or more time windows during the movement of the third displayed object; and determine the difference between the left eye angle and the right eye angle in the one or more time windows during which the third displayed object is closest to the bridge of the nose of the test subject during the computation of impairment indicator information.

7. The impairment assessment device of claim 1 wherein the at least one electronic processor is further programmed to:

cyclically move a fourth displayed object towards and away from an edge of the test subject's vision during the display of the virtual scene;

measure the pupil size as a function of time during the movement of the object; and compute the impairment indicator information based on the measured pupil size as a function of time during the movement of the object.

8. The impairment assessment device of claim 7 wherein the at least one electronic processor is further configured to compute the impairment indicator information by identifying peaks and valleys of the pupil size as a function of time during the movement of the fourth displayed object and computing a ratio of the pupil size at the peaks versus the pupil size at the valleys.

9. The impairment assessment device of claim 8 wherein the peaks and valleys of the pupil size as a function of time during the movement of the fourth displayed object are identified using persistent homology.

10. The impairment assessment device of claim 1, wherein the at least one electronic processor is further programmed to perform operations including:

generating an impairment prediction based on the impairment indicator information wherein the impairment prediction is indicative of at least one of a degree of impairment and a probability of impairment;

wherein the representation of the impairment indicator information comprises the impairment prediction.

11. The impairment assessment device of claim 1, wherein the determined reaction time is a time when a gaze angle of the test subject's eyes is within a first predetermined threshold of the display of the virtual scene.

12. The impairment assessment device of claim 11, wherein the determined accuracy time is a time when a gaze angle of the test subject's eyes is within a second predetermined threshold of the display of the virtual scene, the second predetermined threshold being smaller than the first predetermined threshold.

13. An impairment assessment method comprising:

controlling a virtual reality (VR) headset to display a virtual scene;

measuring a change in one or more features of the test subject's eyes to obtain eye-tracking data, the eye-tracking data including pupil size and gaze direction, in response to the display of the virtual scene using an eye tracker;

measuring a median reaction time, a variability in reaction time, a median accuracy time, and a variability in accuracy time of the test subject's gaze acquisition on a first displayed object, which are calculated by processing the eye-tracking data and removing artifacts from the eye-tracking data;

tracking changes in pupil size in the eye-tracking data in response to changes in light intensity in the virtual scene, applying a segmented regression analysis to identify a transition point at which the pupil stabilizes;

calculating a pupil rebound speed based on a rate of change in pupil size;

computing impairment indicator information from (i) the measured change in the one or more features of the test subject's eyes, (ii) the median reaction time, (iii) the variability in reaction time, (iv) the median accuracy time, (v) the variability in accuracy time, and (vi) the pupil rebound speed, using an electronic processor wherein the impairment indicator information is indicative of impairment of the test subject; and displaying, on an external display of a host computer, a cannabis impairment assessment determined based on the impairment indicator information.

14. The impairment assessment method of claim 13 wherein:

the display of the virtual scene includes cyclically moving a second displayed object towards and away from an edge of the test subject's vision;

the measuring includes measuring an angle of the test subject's eye as a function of time during the moving; and the computing of impairment indicator information includes fitting a line through the angle of the test subject's eye as a function of time to produce a fitted line and computing deviations between the fitted line and the angle of the test subject's eye as a function of time.

15. The impairment assessment method of claim 13 wherein:

the display of the virtual scene includes cyclically moving a third displayed object towards and away from an edge of the test subject's vision;

the measuring includes measuring an angle of the test subject's eye as a function of time during the moving; and the computing of impairment indicator information includes identifying nystagmus in the measured angle of the test subject's eye as a function of time and identifying an onset angle of the nystagmus.

16. The impairment assessment method of claim 13 wherein:

the display of the virtual scene includes moving a fourth displayed object on a cyclic trajectory towards and away from a bridge of a nose of the test subject;

the measuring includes measuring a difference between a left eye angle and a right eye angle at one or more time windows during the moving; and the computing of the impairment indicator information includes determining the difference between the left eye angle and the right eye angle in the one or more time windows during which the fourth displayed object is closest to the bridge of the nose of the test subject.

17. The impairment assessment method of claim 13 wherein:

the display of the virtual scene includes cyclically moving a fifth displayed object towards and away from an edge of the test subject's vision;

the measuring includes measuring the pupil size as a function of time during the moving; and the computing of the impairment indicator information includes identifying peaks and valleys of the pupil size as a function of time during the moving and computing a ratio of the pupil size at the peaks versus the pupil size at the valleys.

18. The impairment assessment method of claim 17 wherein the peaks and valleys of the pupil size as a function of time during the moving are identified using persistent homology.

19. The impairment assessment method of claim 13, wherein the determined reaction time is a time when a gaze angle of the test subject's eyes is within a first predetermined threshold of the display of the virtual scene.

20. The impairment assessment method of claim 19, further including:

measuring an accuracy time of the test subject's gaze acquisition on a first displayed object, wherein wherein the determined accuracy time is a time when a gaze angle of the test subject's eyes is within a second predetermined threshold of the display of the virtual scene, the second predetermined threshold being smaller than the first predetermined threshold.

\* \* \* \* \*